(12) United States Patent
Jewett et al.

(10) Patent No.: US 12,421,537 B2
(45) Date of Patent: Sep. 23, 2025

(54) RIBOSOME VARIANTS FOR SEQUENCE DEFINED POLYMER SYNTHESIS

(71) Applicant: Northwestern University, Evanston, IL (US)

(72) Inventors: Michael Christopher Jewett, Evanston, IL (US); Anne E. d'Aquino, Evanston, IL (US)

(73) Assignee: Northwestern University, Evanston, IL (US)

( * ) Notice: Subject to any disclaimer, the term of this patent is extended or adjusted under 35 U.S.C. 154(b) by 1009 days.

(21) Appl. No.: 17/258,377

(22) PCT Filed: Jul. 8, 2019

(86) PCT No.: PCT/US2019/040860
§ 371 (c)(1),
(2) Date: Jan. 6, 2021

(87) PCT Pub. No.: WO2020/010356
PCT Pub. Date: Jan. 9, 2020

(65) Prior Publication Data
US 2022/0177941 A1    Jun. 9, 2022

Related U.S. Application Data

(60) Provisional application No. 62/694,553, filed on Jul. 6, 2018.

(51) Int. Cl.
*C12P 21/02* (2006.01)
*C12N 1/20* (2006.01)
(Continued)

(52) U.S. Cl.
CPC ............... *C12P 21/02* (2013.01); *C12N 1/20* (2013.01); *C12N 9/104* (2013.01);
(Continued)

(58) Field of Classification Search
CPC .......... C12P 21/02; C12N 1/20; C12N 9/104; C12N 15/1058; C12N 15/113; C12N 2310/128; C12Y 203/02012
See application file for complete search history.

(56) References Cited

U.S. PATENT DOCUMENTS 4,458,066 A    7/1984 Caruthers
4,683,195 A    7/1987 Mullis
(Continued)

FOREIGN PATENT DOCUMENTS

WO    2015184283 A1    12/2015

OTHER PUBLICATIONS

Hayashi JM, Morita YS. Mycobacterial Membrane Domain, or a Primordial Organelle? Yale J Biol Med. Sep. 20, 2019;92(3):549-556. PMID: 31543716; PMCID: PMC6747930. (Year: 2019).*

(Continued)

*Primary Examiner* — Louise W Humphrey
*Assistant Examiner* — Candice Lee Swift
(74) *Attorney, Agent, or Firm* — Quarles & Brady LLP

(57) ABSTRACT

Disclosed are engineered or modified *E. coli* ribosomes and methods, components, compositions, and kits for preparing and identifying engineered or modified *E. coli* ribosomes. The engineered or modified *E. coli* ribosomes may be prepared and identified under a set of defined conditions, such as in the presences of a engineered or modified tRNA comprising a non-natural, non-α-amino acid monomer (NNA), in order to obtain an engineered or modified ribosome that utilizes the engineered or modified tRNA as a substrate for synthesizing a polymer comprising the NNA.

8 Claims, 37 Drawing Sheets

Specification includes a Sequence Listing.

(51) Int. Cl.
    *C12N 9/10*                (2006.01)
    *C12N 15/10*             (2006.01)
    *C12N 15/113*           (2010.01)
(52) U.S. Cl.
    CPC ........ *C12N 15/1058* (2013.01); *C12N 15/113* (2013.01); *C12Y 203/02012* (2013.01); *C12N 2310/128* (2013.01)

(56) References Cited

U.S. PATENT DOCUMENTS

| | | |
|---|---|---|
| 4,683,202 A | 7/1987 | Mullis |
| 5,478,730 A | 12/1995 | Alakhov |
| 5,494,810 A | 2/1996 | Barany |
| 5,556,769 A | 9/1996 | Wu |
| 5,665,563 A | 9/1997 | Beckler |
| 6,168,931 B1 | 1/2001 | Swartz |
| 6,518,058 B1 | 2/2003 | Biryukov et al. |
| 6,548,276 B2 | 4/2003 | Swartz |
| 6,783,957 B1 | 8/2004 | Biryukov et al. |
| 6,869,774 B2 | 3/2005 | Endo |
| 6,994,986 B2 | 2/2006 | Swartz |
| 7,008,651 B2 | 3/2006 | Ambuel |
| 7,118,883 B2 | 10/2006 | Inoue |
| 7,186,525 B2 | 3/2007 | Sakanyan |
| 7,189,528 B2 | 3/2007 | Higashide |
| 7,235,382 B2 | 6/2007 | Endo |
| 7,273,615 B2 | 9/2007 | Endo |
| 7,312,049 B2 | 12/2007 | Calhoun |
| 7,338,789 B2 | 3/2008 | Swartz |
| 7,387,884 B2 | 6/2008 | Suzuki |
| 7,399,610 B2 | 7/2008 | Shikata |
| 7,776,535 B2 | 8/2010 | Mehl |
| 7,817,794 B2 | 10/2010 | Galvin |
| 8,298,759 B2 | 10/2012 | Voloshin |
| 8,357,529 B2 | 1/2013 | Swartz |
| 8,715,958 B2 | 5/2014 | Goerke |
| 8,734,856 B2 | 5/2014 | Endo |
| 9,005,920 B2 | 4/2015 | Kusumegi |
| 9,410,170 B2 | 8/2016 | Calhoun |
| 9,528,137 B2 | 12/2016 | Jewett |
| 9,943,360 B2 | 4/2018 | Miller |
| 10,017,728 B2 | 7/2018 | Jewett |
| 10,118,950 B2 | 11/2018 | Jewett |
| 10,457,932 B2 | 10/2019 | Jewett |
| 10,465,221 B2 | 11/2019 | Jewett |
| 10,577,632 B2 | 3/2020 | Jewett |
| 10,590,456 B2 | 3/2020 | Jewett |
| 10,829,795 B2 | 11/2020 | Jewett |
| 2007/0154983 A1 | 7/2007 | Calhoun |
| 2008/0138857 A1 | 6/2008 | Swartz |
| 2012/0171720 A1 | 7/2012 | Church |
| 2014/0045267 A1 | 2/2014 | Lajoie |
| 2014/0295492 A1 | 10/2014 | Jewett |
| 2014/0349353 A1 | 11/2014 | Nomura |
| 2015/0259757 A1 | 9/2015 | Jewett |
| 2016/0060301 A1 | 3/2016 | Jewett |
| 2016/0083688 A1 | 3/2016 | Jewett |
| 2016/0362708 A1 | 12/2016 | Jewett |
| 2017/0073381 A1 | 3/2017 | Jewett |
| 2017/0306320 A1 | 10/2017 | Jewett |
| 2017/0349928 A1 | 12/2017 | Jewett |
| 2018/0016612 A1 | 1/2018 | Jewett |
| 2018/0016614 A1 | 1/2018 | Jewett |
| 2018/0298416 A1 | 10/2018 | Jewett |
| 2019/0284600 A1 | 9/2019 | Jewett |
| 2020/0063122 A1 | 2/2020 | Jewett |
| 2020/0270665 A1 | 8/2020 | Jewett |
| 2020/0291445 A1 | 9/2020 | Jewett |
| 2021/0139940 A1 | 5/2021 | Jewett |
| 2021/0147894 A1 | 5/2021 | Jewett |
| 2021/0163947 A1 | 6/2021 | Silverman |
| 2021/0163969 A1 | 6/2021 | Jewett |
| 2021/0164059 A1 | 6/2021 | Jewett |
| 2021/0171584 A1 | 6/2021 | Jewett |

OTHER PUBLICATIONS

Griswold, A. (2008) Genome packaging in prokaryotes: the circular chromosome of *E. coli*. Nature Education 1(1):57 (Year: 2008).*
Scitable; https://www.nature.com/scitable/content/proteins-are-long-polymers-made-of-amino-14463000/; accessed Dec. 7, 2023 (Year: 2014).*
Translation: DNA to mRNA to Protein. Nature Education (2008) 1(1): 101 (Year: 2008).*
Gregory, Steven T., and Albert E. Dahlberg. "Mutations in the conserved P loop perturb the conformation of two structural elements in the peptidyl transferase center of 23 S ribosomal RNA." Journal of molecular biology 285.4 (1999): 1475-1483. (Year: 1999).*
Hohsaka, Takahiro, and Masahiko Sisido. "Incorporation of non-natural amino acids into proteins." Current opinion in chemical biology 6.6 (2002): 809-815. (Year: 2002).*
Melo Czekstert ; J Am Chem Soc. Apr. 27, 2016; 138(16): 51945197 (Year: 2016).*
Maini, Rumit, et al. "Incorporation of β-amino acids into dihydrofolate reductase by ribosomes having modifications in the peptidyltransferase center." Bioorganic & medicinal chemistry 21.5 (2013): 1088-1096. (Year: 2013).*
Wu, Yueming, et al. "Host defense peptide mimicking antimicrobial amino acid polymers and beyond: design, synthesis and biomedical applications." Progress in Polymer Science (2023): 101679. (Year: 2023).*
Yang, Rui, Luis R. Cruz-Vera, and Charles Yanofsky. "23S rRNA nucleotides in the peptidyl transferase center are essential for tryptophanase operon induction." Journal of bacteriology 191.11 (2009): 3445-3450. (Year: 2009).*
Maini, Rumit. Study of Ribosomes having Modifications in the Peptidyltransferase Center Using Non-α-L-Amino Acids and Synthesis and Biological Evaluation of Topopyrones. Arizona State University, 2013. (Year: 2012).*
Xu, Jianhua, et al. "Protected nucleotide G2608 in 23S rRNA confers resistance to oxazolidinones in *E. coli*." Biochemical and biophysical research communications 328.2 (2005): 471-476. (Year: 2005).*
Maini, Rumit. Study of ribosomes having modifications in the peptidyltransferase center using non-alpha-L-amino acids and synthesis and biological evaluation of topopyrones. Arizona State University, 2013. (Year: 2013).*
RrID; https://www.ncbi.nlm.nih.gov/nuccore/NC_002695.2?report=genbank&from=4159014&to=4161913&strand=true; accessed Dec. 13, 2024 (Year: 2000).*
RIIA; https://www.ncbi.nlm.nih.gov/nuccore/NC_002695.2?report=genbank&from=4833771&to=4836672; accessed Dec. 13, 2024 (Year: 1999).*
Johns Hopkins; https://www.hopkinsmedicine.org/health/conditions-and-diseases/escherichia-coli-o157-h7; accessed Dec. 13, 2024 (Year: 2024).*
EcoCyc; https://biocyc.org/gene?orgid=ECOLI&id=RRLA-RRNA; accessed Dec. 13, 2024 (Year: 2024).*
Blaha, Gregor, et al. "Mutations outside the anisomycin-binding site can make ribosomes drug-resistant." Journal of molecular biology 379.3 (2008): 505-519. (Year: 2008).*
Toh, Seok-Ming. Target site modifications in the ribosome as antibiotic resistance mechanisms. University of Illinois at Chicago, Health Sciences Center, 2008. (Year: 2008).*
Vázquez-Laslop et al. (Proceedings of the National Academy of Sciences 108.26 (2011): 10496-10501 (Year: 2011).*
Sothiselvam, Shanmugapriya. Functional Interactions Between Ribosome and Nascent Peptide Mediated By Small Molecules. Diss. University of Illinois at Chicago, 2016. (Year: 2016).*
Dedkova, Larisa M., et al. "β-Puromycin selection of modified ribosomes for in vitro incorporation of β-amino acids." Biochemistry 51.1 (2012): 401-415. (Year: 2012).*
Brosius J, Dull TJ, Noller HF. Complete nucleotide sequence of a 23S ribosomal RNA gene from *Escherichia coli*. Proc Natl Acad Sci U S A. Jan. 1980;77(1):201-4. (Year: 1980).*
Martínez, Allyson K., et al. "Interactions of the TnaC nascent peptide with rRNA in the exit tunnel enable the ribosome to respond

(56) References Cited

OTHER PUBLICATIONS to free tryptophan." Nucleic acids research 42.2 (2013): 1245-1256. (Year: 2018).*
Vester, Birte, and Roger A. Garrett. "The importance of highly conserved nucleotides in the binding region of chloramphenicol at the peptidyl transfer centre of *Escherichia coli* 23S ribosomal RNA." The EMBO Journal 7.11 (1988): 3577-3587. (Year: 1988).*
Forster, Kevin A. Determination of the Fitness, Macrolide and Chloramphenicol Resistance of *E. coli* 23S Ribosomal RNA Mutants. Diss. Kalamazoo College, 2010) (Year: 2010).*
Aleksashin, N.A., et al. (2019) Assembly and functionality of the ribosome with tethered subunits. Nat Commun, 10, 930.
Arenz, S., et al. "Drug sensing by the ribosome induces translational arrest via active site perturbation." Molecular cell 56.3 (2014): 446-452.
Arenz, S., et al. (2014) Molecular basis for erythromycin-dependent ribosome stalling during translation of the ErmBL leader peptide. Nat Commun, 5, 3501.
Beaucage, S. L., et al. "Deoxynucleoside phosphoramidites—a new class of key intermediates for deoxypolynucleotide synthesis." Tetrahedron letters 22.20 (1981): 1859-1862.
Beringer, M. et al. (2007) Importance of tRNA interactions with 23S rRNA for peptide bond formation on the ribosome: studies with substrate analogs. Biol Chem, 388, 687-691.
Beringer, M. et al. (2007) The Ribosomal Peptidyl Transferase. Molecular Cell, 26, 311-321.
Blaha, G., et al. "Mutations outside the anisomycin-binding site can make ribosomes drug-resistant." Journal of molecular biology 379.3 (2008): 505-519.
Bobkova, E. V., et al. "Catalytic properties of mutant 23 S ribosomes resistant to oxazolidinones." Journal of Biological Chemistry 278.11 (2003): 9802-9807.
Bocchetta, M., et al. (1998) 23S rRNA positions essential for tRNA binding in ribosomal functional sites. Proceedings of the National Academy of Sciences, 95, 3525.
Boumghar-Bourtchai, L., et al. "Influence of recombination on development of mutational resistance to linezolid in Enterococcus faecalis JH2-2." Antimicrobial agents and chemotherapy 53.9 (2009): 4007-4009.
Bourgeois-Nicolaos, N., et al. "Dose dependence of emergence of resistance to linezolid in Enterococcus faecalis in vivo." The Journal of infectious diseases 195.10 (2007): 1480-1488.
Bremer, H., et al. (1996) In Neidhart, e. a. (ed.), *Escherichia coli* and *Salmonella typhirium*: Cellular and Molecular Biology, 2nd ed., pp. 1559.
Brown, E. L., et al. "[8] Chemical synthesis and cloning of a tyrosine tRNA gene." Methods in Enzymology. vol. 68. Academic Press, 1979. 109-151.
Brunelle, J.L., et al. (2006) The interaction between C75 of tRNA and the A loop of the ribosome stimulates peptidyl transferase activity. RNA, 12, 33-39.
Camps, M., et al. "An rRNA mutation identifies the apicoplast as the target for clindamycin in Toxoplasma gondii." Molecular microbiology 43.5 (2002): 1309-1318.
Canu, A., et al. "Diversity of ribosomal mutations conferring resistance to macrolides, clindamycin, streptogramin, and telithromycin in *Streptococcus pneumoniae*." Antimicrobial Agents and Chemotherapy 46.1 (2002): 125-131.
Carlson, E.D., et al. (2012) Cell-free protein synthesis: Applications come of age. Biotechnology Advances, 30, 1185-1194.
Clementi, N., et al. (2010) Atomic mutagenesis reveals A2660 of 23S ribosomal RNA as key to EF-G GTPase activation. Nat Chem Biol, 6, 344-351.
Cochella, L. et al. "Isolation of antibiotic resistance mutations in the rRNA by using an in vitro selection system." Proceedings of the National Academy of Sciences 101.11 (2004): 3786-3791.
D'Aquino, A.E., et al. (2018) Engineered Ribosomes for Basic Science and Synthetic Biology. Annual Review of Chemical and Biomolecular Engineering, 9, 311-340.
Dedkova, L.M. et al. (2012) beta-Puromycin selection of modified ribosomes for in vitro incorporation of beta-amino acids. Biochemistry, 51, 401-415.
Dedkova, L.M. et al. (2019) Expanding the Scope of Protein Synthesis Using Modified Ribosomes. Journal of the American Chemical Society, 141, 6430-6447.
Depardieu, F. et al. "Mutation in 23S rRNA responsible for resistance to 16-membered macrolides and streptogramins in *Streptococcus pneumoniae*." Antimicrobial Agents and Chemotherapy 45.1 (2001): 319-323.
Erlacher, M.D., et al. (2011) Generation of chemically engineered ribosomes for atomic mutagenesis studies on protein biosynthesis. Nat. Protocols, 6, 580-592.
Ettayebi, M. et al. "Chloramphenicol-erythromycin resistance mutations in a 23S rRNA gene of *Escherichia coli*." Journal of Bacteriology 162.2 (1985): 551-557.
Fried, S.D., et al. (2015) Ribosome Subunit Stapling for Orthogonal Translation in *E. coli*. Angewandte Chemie (International Ed. in English), 54, 12791-12794.
Fritz et al., "Biology by design: from top to bottom and back," J Biomed Biotechnol. 2010;2010:232016.
Fritz, B.R. et al. "The impact of transcriptional tuning on in vitro integrated rRNA transcription and ribosome construction," Nucl. Acids Res. Jun. 2014;42(10):6774-85.
Fritz, B.R., et al. (2015) Implications of macromolecular crowding and reducing conditions for in vitro ribosome construction. Nucleic Acids Res. 43(9), 4774.
Fulle, S., et al. "Complex long-distance effects of mutations that confer linezolid resistance in the large ribosomal subunit." Nucleic acids research 43.16 (2015): 7731-7743.
Furneri, P. M., et al. "Two new point mutations at A2062 associated with resistance to 16-membered macrolide antibiotics in mutant strains of Mycoplasma hominis." Antimicrobial agents and chemotherapy 45.10 (2001): 2958-2960.
Gagnon, M. G., et al. "Structures of proline-rich peptides bound to the ribosome reveal a common mechanism of protein synthesis inhibition." Nucleic acids research 44.5 (2016): 2439-2450.
Goodchild, J. "Conjugates of oligonucleotides and modified oligonucleotides: a review of their synthesis and properties." Bioconjugate Chemistry 1.3 (1990): 165-187.
Green, R., et al. (1999) Reconstitution of Functional 50S Ribosomes from in Vitro Transcripts of Bacillus stearothermophilus 23S rRNA. Biochemistry, 38, 1772-1779.
Green, R., et al. (1997) Mutations at nucleotides G2251 and U2585 of 23 S rRNA perturb the peptidyl transferase center of the ribosome 1 1 Edited by P. E. Wright. Journal of Molecular Biology, 266, 40-50.
Green, R., et al. (1998) Ribosome-catalyzed peptide-bond formation with an A-site substrate covalently linked to 23S ribosomal RNA. Science, 280, 286-289.
Gregory, S. T., et al. "Mutational analysis of 16S and 23S rRNA genes of Thermus thermophilus." Journal of bacteriology 187.14 (2005): 4804-4812.
Gregory, S.T., et al. (1994) Mutations in the peptidyl transferase region of *E.coli* 23S rRNA affecting translational accuracy. Nucleic Acids Research, 22, 279-284.
Gumbart, J., et al. (2012) Mechanisms of SecM-Mediated Stalling in the Ribosome. Biophysical Journal, 103, 331-341.
Hesslein, A.E., et al. (2004) Exploration of the conserved A+C wobble pair within the ribosomal peptidyl transferase center using affinity purified mutant ribosomes. Nucleic Acids Research, 32, 3760-3770.
Huang, A., et al. (2018) BioBitsTM Explorer: A modular synthetic biology education kit. Science Advances, 4, eaat5105.
International Searching Authority. International Search Report and Written Opinion for application PCT/US2019/040860. Mailed on Oct. 24, 2019. 8 pages.
Jaroentomeechai, T., et al. (2018) Single-pot glycoprotein biosynthesis using a cell-free transcription-translation system enriched with glycosylation machinery. Nat Commun, 9, 2686.
Jewett, M.C., et al. (2013) In vitro integration of ribosomal RNA synthesis, ribosome assembly, and translation. Mol Syst Biol, 9, 678.

(56) References Cited

OTHER PUBLICATIONS

Kaczanowska, M. et al. (2007) Ribosome biogenesis and the translation process in *Escherichia coli*. Microbiology and Molecular Biology Reviews, 71, 477-494.

Kightlinger, W., et al. (2018) Design of glycosylation sites by rapid synthesis and analysis of glycosyltransferases. Nat Chem Biol, 14, 627-635.

Kim, D.F. et al. (1999) Base-pairing between 23S rRNA and tRNA in the ribosomal A site. Mol Cell, 4, 859-864.

Kloss, P., et al. "Resistance mutations in 23 S rRNA identify the site of action of the protein synthesis inhibitor inezolid in the ribosomal peptidyl transferase center." Journal of molecular biology 294.1 (1999): 93-101.

Li, B.-B., et al. "Mutations in 23S rRNA gene associated with decreased susceptibility to tiamulin and valnemulin in Mycoplasma gallisepticum." FEMS microbiology letters 308.2 (2010): 144-149.

Li, B.-B., et al. "Single and dual mutations at positions 2058, 2503 and 2504 of 23S rRNA and their relationship to resistance to antibiotics that target the large ribosomal subunit." Journal of antimicrobial chemotherapy 66.9 (2011): 1983-1986.

Thompson, J., et al. (2001) Analysis of mutations at residues A2451 and G2447 of 23S rRNA in the peptidyltransferase active site of the 50S ribosomal subunit. Proceedings of the National Academy of Sciences of the United States of America, 98, 9002-9007.

Vazquez-Laslop, N., et al. "Role of antibiotic ligand in nascent peptide-dependent ribosome stalling." Proceedings of the National Academy of Sciences 108.26 (2011): 10496-10501.

Vester, B. et al. "The importance of highly conserved nucleotides in the binding region of chloramphenicol at the peptidyl transfer centre of *Escherichia coli* 23S ribosomal RNA." The EMBO Journal 7.11 (1988): 3577-3587.

Wang, L. et al. Insights into the Molecular determinants of EF-G Catalyzed Translocation. RNA. 2011. vol 17, No. 12, pp. 2189-2200.

Wang, L., et al. (2006) Expanding the genetic code. Annu. Rev. Biophys. Biomol. Struct., 35, 225-249.

Wetmur, J. G. "DNA probes: applications of the principles of nucleic acid hybridization." Critical reviews in biochemistry and molecular biology 26.3-4 (1991): 227-259.

Willi, J., et al. (2018) Oxidative stress damages rRNA inside the ribosome and differentially affects the catalytic center. Nucleic Acids Res, 46, 1945-1957.

Xie, J. et al. (2006) A chemical toolkit for proteins—an expanded genetic code. Nat Rev Mol Cell Biol, 7, 775-782.

Xiong, L. et al. "Binding site of the bridged macrolides in the *Escherichia coli* ribosome." Antimicrobial agents and chemotherapy 49.1 (2005): 281-288.

Xiong, L., et al. "Oxazolidinone resistance mutations in 23S rRNA of *Escherichia coli* reveal the central region of domain V as the primary site of drug action." Journal of bacteriology 182.19 (2000): 5325-5331.

Xu, J., et al. "Protected nucleotide G2608 in 23S rRNA confers resistance to oxazolidinones in *E. coli*." Biochemical and biophysical research communications 328.2 (2005): 471-476.

Yarza, P., et al. (2010) Update of the All-Species Living Tree Project based on 16S and 23S rRNA sequence analyses. Systematic and Applied Microbiology, 33, 291-299.

Yassin, A. et al. (2007) Potential new antibiotic sites in the ribosome revealed by deleterious mutations in RNA of the large ribosomal subunit. J Biol Chem, 282, 24329-24342.

Youngman, E. M., et al. "The active site of the ribosome is composed of two layers of conserved nucleotides with distinct roles in peptide bond formation and peptide release." Cell 117.5 (2004): 589-599.

Lieberman, K.R. et al. (1994) The importance of conserved nucleotides of 23 S ribosomal RNA and transfer RNA in ribosome catalyzed peptide bond formation. J Biol Chem, 269, 16163-16169.

Liu, C.C., et al. (2018) Toward an orthogonal central dogma. Nature Chemical Biology, 14, 103.

Liu, Y., et al. (2014) Characterizing and Alleviating Substrate Limitations for Improved in vitro Ribosome Construction. ACS Synth Biol.

Liu, Y., et al. (2017) Repurposing ribosomes for synthetic biology. Current Opinion in Chemical Biology, 40, 87-94.

Long, K. S., et al. "Mutations in 23S rRNA at the peptidyl transferase center and their relationship to linezolid binding and cross-resistance." Antimicrobial agents and chemotherapy 54.11 (2010): 4705-4713.

Long, K. S., et al. "Single 23S rRNA mutations at the ribosomal peptidyl transferase centre confer resistance to valnemulin and other antibiotics in Mycobacterium smegmatis by perturbation of the drug binding pocket." Molecular microbiology 71.5 (2009): 1218-1227.

Maini, R., et al. (2013) Incorporation of beta-amino acids into dihydrofolate reductase by ribosomes having modifications in the peptidyltransferase center. Bioorg Med Chem, 21, 1088-1096.

Maini, R., et al. (2015) Protein Synthesis with Ribosomes Selected for the Incorporation of $\beta$-Amino Acids. Biochemistry.

Maivali, U., et al. "Mutations in the *Escherichia coli* 23S rRNA increase the rate of peptidyl-tRNA dissociation from the ribosome." Molekuliarnaia biologiia 35.4 (2001): 666-671.

Maki, J.A. and Culver, G.M. (2005) Recent developments in factor-facilitated ribosome assembly. Methods, 36, 313-320.

Marks, J., et al. (2016) Context-specific inhibition of translation by ribosomal antibiotics targeting the peptidyl transferase center. Proceedings of the National Academy of Sciences, 113, 12150-12155.

Martin, R.W., et al. (2018) Cell-free protein synthesis from genomically recoded bacteria enables multisite Incorporation of noncanonical amino acids. Nat Commun, 9, 1203.

Melo Czekster, C., et al. (2016) In Vivo Biosynthesis of a $\beta$-Amino Acid-Containing Protein. Journal of the American Chemical Society, 138, 5194-5197.

Metelev, M., et al. "Klebsazolicin inhibits 70S ribosome by obstructing the peptide exit tunnel." Nature chemical biology 13.10 (2017): 1129-1136.

Moine, H. et al. (1994) Mutations in helix 34 of *Escherichia coli* 16 S ribosomal RNA have multiple effects on ribosome function and synthesis. J Mol Biol, 243, 402-412.

Narang, S. A., et al. "[6] Improved phosphotriester method for the synthesis of gene fragments." Methods in Enzymology. vol. 68. Academic Press, 1979. 90-98.

Nierhaus, K.H. et al. (1974) Total Reconstitution of Functionally Active 50S Ribosomal Subunits from *Escherichia coli*. Proceedings of the National Academy of Sciences of the United States of America, 71, 4713-4717.

Nissen, P., et al. (2000) The Structural Basis of Ribosome Activity in Peptide Bond Synthesis. Science, 289, 920-930.

Noeske, J., et al. (2015) High-resolution structure of the *Escherichia coli* ribosome. Nat Struct Mol Biol, 22, 336-341.

O'Connor, M et al. (1993) Functional tRNAs with altered 3' ends. Embo j, 12, 2559-2566.

O'Connor, M. et al. (1993) Mutations at U2555, a tRNA-protected base in 23S rRNA, affect translational fidelity. Proceedings of the National Academy of Sciences, 90, 9214-9218.

O'Connor, M et al. (1997) Decoding fidelity at the ribosomal A and P sites: influence of mutations in three different regions of the decoding domain in 16S rRNA. Nucleic Acids Research, 25, 1185-1193.

O'Connor, M., et al. (2001) Mutagenesis of the peptidyltransferase center of 23S rRNA: the invariant U2449 is dispensable. Nucleic Acids Research, 29, 710-715.

Ogle, J.M., et al. (2003) Insights into the decoding mechanism from recent ribosome structures. Trends Biochem Sci, 28, 259-266.

Orelle, C., et al. (2015) Protein synthesis by ribosomes with tethered subunits. Nature, 524, 119-124.

Osterman, I.A., et al. (2017) Madumycin II inhibits peptide bond formation by forcing the peptidyl transferase center Into an inactive state. Nucleic Acids Res.

Owczarzy, R., et al. "Predicting stability of DNA duplexes in solutions containing magnesium and monovalent cations." Biochemistry 47.19 (2008): 5336-5353.

(56) References Cited

OTHER PUBLICATIONS

Paier, A., et al. "The effects of disruptions in ribosomal active sites and in intersubunit contacts on ribosomal degradation in *Escherichia coli*." Scientific reports 5.1 (2015): 1-8.

Pang, Y., et al. "The antiprion compound 6-aminophenanthridine inhibits the protein folding activity of the ribosome by direct competition." Journal of Biological Chemistry 288.26 (2013): 19081-19089.

Pape, T., et al. (1998) Complete kinetic mechanism of elongation factor Tu-dependent binding of aminoacyl-tRNA to the A site of the *E.coli* ribosome. The EMBO Journal, 17, 7490-7497.

Pfister, P., et al. "23S rRNA base pair 2057-2611 determines ketolide susceptibility and fitness cost of the macrolide resistance mutation 2058A G." Proceedings of the National Academy of Sciences 102.14 (2005): 5180-5185.

Poehlsgaard, J., et al. "Molecular mechanisms by which rRNA mutations confer resistance to clindamycin." Antimicrobial agents and chemotherapy 49.4 (2005): 1553-1555.

Polacek, N. (2011) The ribosome meets synthetic biology. Chembiochem, 12, 2122-2124.

Polacek, N. et al. (2005) The ribosomal peptidyl transferase center: structure, function, evolution, inhibition. Crit Rev Biochem Mol Biol, 40, 285-311.

Polacek, N., et al. "The critical role of the universally conserved A2602 of 23S ribosomal RNA in the release of the nascent peptide during translation termination." Molecular cell 11.1 (2003): 103-112.

Polacek, N., et al. (2001) Ribosomal peptidyl transferase can withstand mutations at the putative catalytic nucleotide. Nature, 411, 498-501.

Polikanov, Y.S., et al. (2014) A proton wire to couple aminoacyl-tRNA accommodation and peptide-bond formation on the ribosome. Nature structural & molecular biology, 21, 787-793.

Porse, B. T., et al. "Mapping important nucleotides in the peptidyl transferase centre of 23 S rRNA using a random mutagenesis approach." Journal of molecular biology 249.1 (1995): 1-10.

Porse, B.T., et al. (1996) The Donor Substrate Site within the Peptidyl Transferase Loop of 23 S rRNA and its Putative Interactions with the CCA-end of N-blocked Aminoacyl-tRNAPhe. Journal of Molecular Biology, 264, 472-483.

Prunier, A.-L., et al. "Clinical isolates of *Staphylococcus aureus* with ribosomal mutations conferring resistance to macrolides." Antimicrobial agents and chemotherapy 46.9 (2002): 3054-3056.

Saarma, U. et al. "Novel mutants of 23S RNA: characterization of functional properties." Nucleic acids research 20.12 (1992): 3147-3152.

Saarma, U., et al. "Mutational analysis of the donor substrate binding site of the ribosomal peptidyltransferase center." RNA 4.2 (1998): 189-194.

Samaha, R.R., et al. (1995) A base pair between tRNA and 23S rRNA in the peptidyl transferase centre of the ibosome. Nature, 377, 309-314.

Schmied, W.H., et al. (2018) Controlling orthogonal ribosome subunit interactions enables evolution of new function. Nature, 564, 444-448.

Semrad, K. et al. (2002) Osmolytes stimulate the reconstitution of functional 50S ribosomes from in vitro transcripts of *Escherichia coli* 23S rRNA. Rna, 8, 401-411.

Spahn, CMT, et al. "Mutational analysis of two highly conserved UGG sequences of 23 S rRNA from *Escherichia coli*." Journal of Biological Chemistry 271.51 (1996): 32849-32856.

Stark, J.C., et al. (2018) BioBitsTM Bright: A fluorescent synthetic biology education kit. Science Advances, 4, eaat5107.

Sulyok, K. M., et al. "Mutations associated with decreased susceptibility to seven antimicrobial families in field and laboratory-derived Mycoplasma bovis strains." Antimicrobial agents and chemotherapy 61.2 (2017): e01983-16.

Swartz, J.R., et al. (2004) Cell-free protein synthesis with prokaryotic combined transcription-translation. Methods Mol Biol, 267, 169-182.

Tait-Kamradt, A., et al. "Mutations in 23S rRNA and ribosomal protein L4 account for resistance in pneumococcal strains selected in vitro by macrolide passage." Antimicrobial agents and chemotherapy 44.8 (2000): 2118-2125.

\* cited by examiner

C

| Ribosomes | Relative ratio of Subunits:70s+Polysomes | Relative ratio of 70S:Polysomes |
|---|---|---|
| WT | 2.2 | 5.2 |
| A2062U | 1.8 | 3.0 |
| G2057U | 2.5 | 4.8 |
| C2496G | 2.4 | 13.8 |
| A2451C | 2.3 | 9.0 |
| U2585G | 1.8 | 3.9 |
| A2451U | 1.8 | 8.4 |
| G2455A | 3.9 | 4.0 |
| C2452G | 2.5 | 28.0 |

Figure 5 (continued)

RIBOSOME VARIANTS FOR SEQUENCE DEFINED POLYMER SYNTHESIS

CROSS-REFERENCE TO RELATED PATENT APPLICATIONS

The present application represents the U.S. national stage entry of International Application PCT/US2019/040860, filed Jul. 8, 2019, which claims the benefit of priority under 35 U.S.C. § 119(e) to U.S. Provisional Application 62/694,553, filed on Jul. 6, 2018, the content of which is incorporated herein by reference in their entireties.

STATEMENT REGARDING FEDERALLY SPONSORED RESEARCH OR DEVELOPMENT

This invention was made with government support under W911NF-16-1-0372 and S911NF-18-1-0181 awarded by the Army Research Office of the Department of Defense; and MCB-1716766 awarded by the National Science Foundation. The government has certain rights in the invention.

SEQUENCE LISTING

A Sequence Listing accompanies this application and is submitted as an ASCII text file of the sequence listing named "70258101877_ST25.txt" which is 4,261 bytes in size and was created on Apr. 17, 2025. The sequence listing is electronically submitted via Patent Center with the application and is incorporated herein by reference in its entirety.

Applicant also submits a CRF of the ST25.txt form of the sequence listing. The sequence listing and amendment to the specification add no new matter, and entry thereof is respectfully requested.

BACKGROUND

The present invention generally relates to ribosomes and ribosome variants for use in performing sequence defined polymer synthesis. More specifically, the present invention discloses mutational characterization and mapping of the active site of a ribosome, resulting in identification of permissible mutants that can be used to engineer the ribosome for the production of sequence defined polymers.

*Escherichia coli* ribosomes are capable of polymerizing amino acids into complex polypeptides with diverse functions. To engineer or modify ribosomes, we have previously reported on the integrated synthesis, assembly, and translation (iSAT) system, in which ribosomal RNA (rRNA) can be in vitro transcribed and assembled into functional ribosomes. (See U.S. Published Application No. 2016/0083688, the content so which is incorporated herein by reference in its entirety). We also previously reported the coupling of the iSAT system with ribosome display, a method for stalling ribosomes, to create the ribosome synthesis and evolution (RISE) method. RISE uses mutated DNA to build a library of ribosomes that can then be screened for functionality under different conditions. (See U.S. Published Application No. 2017/0306320, the content of which is incorporated herein by reference in its entirety). With our optimized protocols, we observe >1,000-fold specificity for functional ribosomes, which allows for rapid screening of large libraries of rRNA mutations. As a demonstration, we used RISE to explore mutations of the ribosomal peptidyl transferase center, and found RISE rapidly converged libraries of 4,096 and $1.7 \times 10^7$ sequences back to the wild type sequence. Additionally, we evolved resistance to the antibiotic clindamycin and uncovered novel resistant combinations of base mutations. Moving forward, RISE will serve as a powerful new approach for exploring the effects of rRNA mutations on ribosome function and to ultimately isolate ribosomal variants with altered functionalities.

Methods of ribosome engineering are of great interest to the fields of biotechnology, chemistry, and material science. The development of an in vitro ribosome biogenesis technology expands the possibilities of ribosome engineering and modification. Ribosomes may be engineered and/or modified to incorporate unnatural amino acids for expanded protein functionality or to perform new chemistry for the production of non-protein polymers. The disclosed methods modify iSAT technology to identify permissible mutant ribosomes.

Here, utilizing our iSAT technology, we have created a comprehensive set of mutants in the peptidyl transferase center of ribosomal RNA (rRNA) and assessed biological activity of the mutants in various assays. The identified ribosomes may be able to synthesize sequence-controlled polymers such as polyolefin polymers, aramid polymers, polyurethane polymers, polyketide polymers, conjugated polymers, D-amino acid polymers, β-amino acid polymers, γ-amino acid polymers, δ-amino acid polymers, ε-amino acid polymers, ζ-amino acid polymers polycarbonate polymers, and benzoic acid polymers. This achievement will ultimately allow the template-guided biosynthesis and evolution of sequence-controlled peptide mimetics, polyketides, fatty acids, and ever more complex molecules that combine these disparate functional units. Further, it will allow the manufacture of polymers based on alternative poly-condensation chemistries (i.e., non amide bonds). The identified ribosomes also may be analysis of antibiotic resistance and identification of new antibiotics.

SUMMARY

Presently disclosed are engineered or modified *E. coli* ribosomes and methods, components, compositions, and kits for preparing, identifying, engineering, and utilizing modified *E. coli* ribosomes. The engineered or modified *E. coli* ribosomes may be prepared and identified under a set of defined conditions and the identified ribosomes may be utilized in methods for sequence defined polymer synthesis. The engineered or modified *E. coli* ribosomes in particular may include one or more mutations in ribosomal RNA (rRNA), including but not limited to the peptidyl transferase center of rRNA.

The disclosed methods include methods of identifying an engineered and/or modified *E. coli* ribosome having functional activity under a defined condition. The methods may include: (a) performing an integrated ribosome synthesis assembly and translation (iSAT) reaction with a library of mutated rRNA templates and a ribosome display reporter template; and (b) selecting and/or identifying mutated rRNA templates with desirable activities. The disclosed methods may include methods of identifying an engineered and/or modified *E. coli* ribosome having functional activity in the presence of a modified tRNA and/or an antibiotic. As such, engineered and/or modified *E. coli* ribosomes also are contemplated herein.

Also disclosed are kits. The disclosed kits may include one or more components for performing any of the disclosed methods including kits for preparing, identifying, engineering, and utilizing modified *E. coli* ribosomes. The disclosed kits also may include one or more components for utilizing the disclosed engineered or modified *E. coli* ribosomes in in vitro methods, such as in vitro methods for performing sequence defined polymer synthesis utilizing the disclosed engineered or modified E. coli ribosomes.

DETAILED DESCRIPTION

Definitions and Terminology

Figure 1:
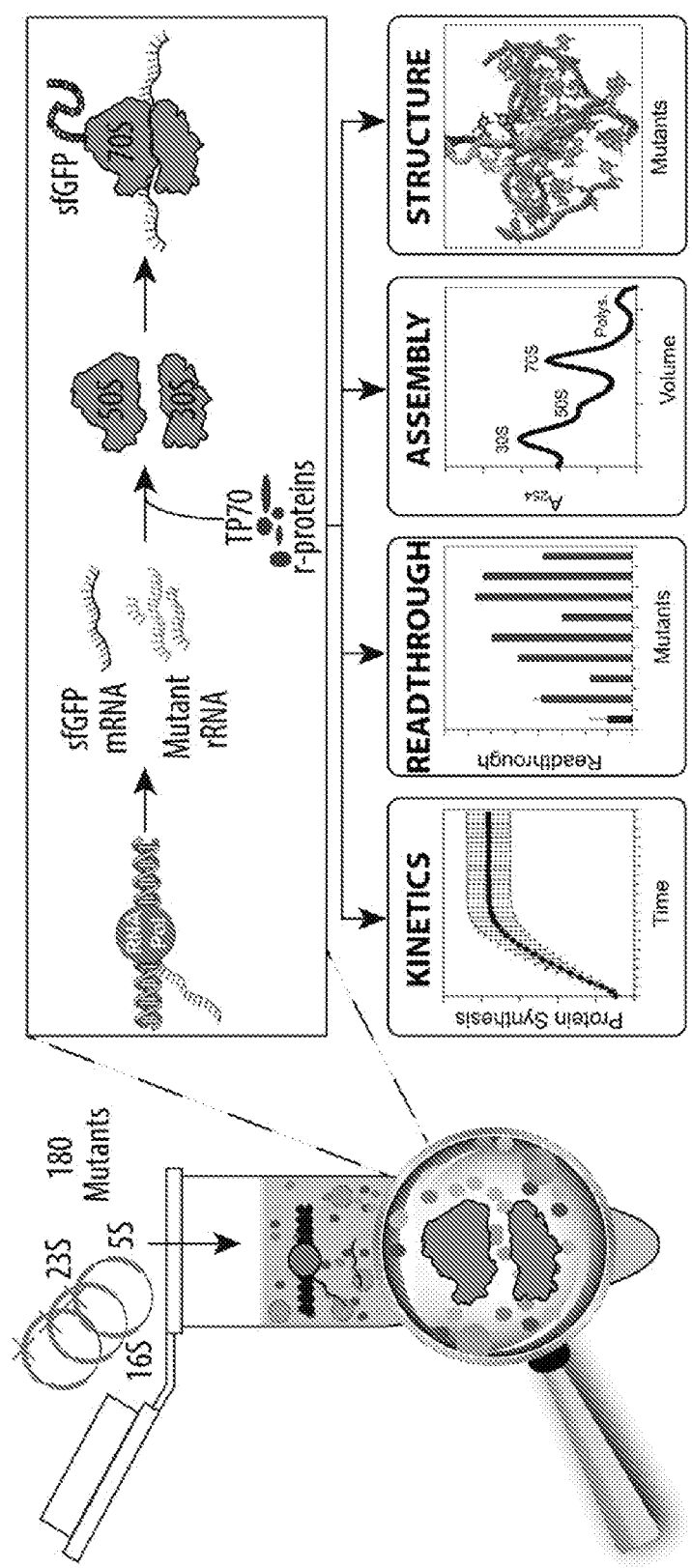
FIG. 1. Graphical abstract. Studying ribosome active site mutants using an in vitro platform. Peptidyl transferase center (PTC) mutant plasmids were introduced into in vitro integrated synthesis, assembly, and translation (iSAT) reactions along with cell-free iSAT reagents. Once iSAT reactions are initiated, T7 RNA polymerase transcribes sfGFP mRNA as well as rRNA. The rRNA coassembles with ribosomal proteins (TP70) to form iSAT ribosomes. These ribosomes can then translate the reporter protein mRNA (sfGFP). Upon completion of an iSAT reaction, kinetics, structure, fidelity, and assembly analyses can be carried out to characterize ribosomes in vitro.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the terms "an rRNA" and "a tRNA" should be interpreted to mean "one or more rRNAs" and "one or more tRNAs" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry,* 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro ribosomal assembly, transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited to, a p-acetyl-L-phenylalanine, a p-iodo-L-phenylalanine, an O-methyl-L-tyrosine, a p-propargyloxyphenylalanine, a p-propargylphenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenyl-alanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 19ufa19hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The disclosed platforms may be utilized to evolve ribosomes that can be used to mediate polymerization of amino acid monomers and/or non-amino acid monomers. Non-amino acid monomers that may be subjected to ribosome-mediated polymerization include, but are not limited to: polyester monomers, polyaramid monomers, polyurethane monomers, polyketide monomers, polyolefin monomers, polycarbonate monomers, polyethylene monomers, polypropylene monomers, coumarin monomers, phenylene monomers, and vinylene monomers among others. Preferably, the disclosed evolved ribosomes may be utilized to mediate polymerization of a range of "A|B"-type monomers which form complementary nucleophilic and electrophilic monomer pairs for polymerization.

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Ribosome Synthesis

Methods for making ribosomes have been disclosed in published U.S. patent applications, e.g., U.S. Published Application No. 2012-017120, the content of which is incorporated herein by reference in its entirety. Methods for making ribosomes have been described in scientific publications, e.g., Fritz et al., "Implications of macromolecular crowding and reducing conditions for in vitro ribosome construction," Nucl. Acids. Res. 2015 May 19; 43(9):4774-84; Liu et al., "Characterizing and alleviating substrate limitations for improved in vitro ribosome construction," ACS Synth. Biol. 2015 Apr. 17; 4(4):454-62; Fritz and Jewett, "The impact of transcriptional tuning on in vitro integrated rRNA transcription and ribosome construction," Nucl. Acids Res. 2014 June; 42(10):6774-85; and Jewett et al., "In vitro integration of ribosomal RNA synthesis, ribosome assembly, and translation," Mol. Syst. Biol. 2013 Jun. 25; 9:678; the contents of which are incorporated herein by reference in their entireties.

The methods disclosed herein include methods of reconstituting a functional translation unit. In certain aspects, the reconstituted ribosomes described herein can synthesize a reporter. Furthermore, active *E. coli* ribosomes can be reconstituted in a one-step incubation procedure at 37° C. under conditions that mimic the cytoplasm. In vitro transcribed 16S rRNA and 23S rRNA, may be combined with native ribosomal proteins and native 5S rRNA in order to self-assemble functional synthetic ribosomes.

In some embodiments, compositions for rRNA synthesis, ribosome assembly and protein synthesis in one vessel are provided. The reconstitution methods described herein facilitate the in vitro analysis of ribosomal mutations for understanding the molecular details of ribosome function. The reconstitution methods described herein enable cell-free synthetic biology as a platform for evolving ribosomes for the production of protein therapeutics and peptide drugs that are difficult to make in vivo.

In some embodiments, methods for making an in vitro assembled ribosomal subunit and/or ribosome are provided. In certain aspects, a modular, step-wise approach is provided in which in vivo purified portions of ribosomes and/or in vitro produced purified portions of ribosomes can be used to make natural ribosomes or ribosomal subunits, semi-synthetic ribosomes or ribosomal subunits (i.e., portions are in vivo purified and portions are in vitro produced (i.e., by in vitro transcription and/or in vitro translation)) as well as fully synthetic ribosomes or ribosomal subunits (i.e., the entire ribosome or ribosomal subunit is made up of portions that were in vitro produced (i.e., by in vitro transcription and/or in vitro translation)). As used herein, a portion of a ribosome refers to a polypeptide, a ribosomal subunit or an rRNA that can be used to produce a ribosome. Proteins and/or polypeptides produced by in vitro translation may be referred to as "synthetic proteins" and "synthetic polypeptides," respectively. In vitro transcribed rRNA is referred to herein as "synthetic rRNA."

In certain aspects, ribosomal subunit assembly and/or ribosome assembly and in vitro rRNA transcription are performed in the same vessel, optionally concomitantly. In other aspects, ribosomal subunit assembly and/or ribosome assembly and in vitro translation are performed in the same vessel optionally concomitantly. In still other aspects, ribosomal subunit assembly and/or ribosome assembly, in vitro rRNA transcription, and in vitro translation are performed in the same vessel optionally concomitantly.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, ribosomal subunit/ribosome assembly, and/or translation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for coupled ribosome assembly and translation, e.g., potassium glutamate, ammonium chloride and the like. Ribosomal subunits are reconstituted in physiological conditions (e.g., constant temperature and magnesium). Using cytoplasmic mimicry as a guide, salt conditions are provided as well as salts themselves in which ribosomal subunits are reconstituted. Physiological cytoplasmic salt conditions are well-known to those of skill in the art.

In certain exemplary embodiments, methods for the in vitro assembly of ribosomes and/or ribosomal subunits are provided. As used herein, the term assemble refers to the ability of portions of ribosomes to interact with one another. As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

In certain exemplary embodiments, one or more reporter polypeptides and/or proteins are utilized as a read-out to assay ribosomal subunit and/or ribosome activity (i.e., the ability of the ribosomal subunit and/or ribosome to mediate translation). In certain aspects, the polypeptide and/or protein contains a detectable label. In other aspects, the reporter polypeptide and/or protein provides a biological activity (e.g., an enzymatic activity, bioluminescence, fluorescence or the like) that serves as a detectable label.

Examples of fluorescent proteins include, but are not limited to, yellow fluorescent protein (YFP), green fluorescence protein (GFP), cyan fluorescent protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like.

Methods for In Vitro Ribosome Synthesis and Evolution

The present inventors have invented methods, components, compositions, and kits for preparing and identifying engineered and/or modified E. coli ribosomes. The E. coli ribosomes may be prepared and identified under a set of defined conditions.

In a first aspect, a method of identifying an engineered and/or modified E. coli ribosome having functional activity under a defined condition is described. The method may include the following steps: (a) performing an integrated ribosome synthesis assembly and translation (iSAT) reaction (e.g., as disclosed herein) with a library of mutated rRNA templates (e.g., as disclosed herein) and a ribosome display reporter template (e.g., as disclosed herein); and (b) partitioning a subpopulation of rRNAs in assembled mutated ribosomes having translational activity under the defined condition from a remainder population of mutated rRNAs present in the iSAT reaction; and (c) enriching the partitioned subpopulation of rRNAs in assembled mutated ribosomes having translational activity to identify the engineered and/or modified E. coli ribosome having functional activity under the defined condition. In the disclosed methods, the steps (a)-(c) may be executed in a reiterative manner.

Optionally, the method includes a step whereby a library of mutated rRNA templates is generated prior to performing the method. In some embodiments, the library of mutated rRNA templates is generated by a method that includes a step selected from the group consisting of DNA shuffling, error-prone DNA amplification, degenerate primer-based DNA amplification, and specific modifications based on crystal structure guided rational targeting. The library may include members representing one of four different nucleotides at one or more variable positions in the rRNA, wherein $4^N$ represents the theoretical number of different members in the library and N represents the number of variable positions.

The disclosed methods may utilize a ribosome display reporter template. The ribosome display reporter template may be transcribed from a plasmid vector such as the vectors described herein. The plasmid vector may include a reporter gene operably linked to a 5'-promoter element, a 3'-spacer element, and a 3'-self-cleaving ribozyme element. As such, from 5'→3', the vector may include 5'-promoter element→reporter gene→3'-spacer element→3'-self-cleaving ribozyme element.

The reporter gene utilized in the disclosed methods may encode a binding partner as disclosed herein, and the disclosed methods may include a partitioning step that utilizes the binding partner. In some embodiments, the partitioning step may include: (i) forming a ternary complex comprising a stalled ribosome on a mRNA terminated by a self-cleaving ribozyme in the presence of an anti-ssrA oligonucleotide; and (ii) selecting the ternary complex with a cognate binding partner to the binding partner encoded by the reporter gene to form a quaternary complex comprising the ternary complex associated with the cognate binding partner. The cognate binding partner to the binding partner encoded by the reporter gene may comprise a capture reagent. For example, the binding partner encoded by the reporter gene may comprise a peptide tag that is captured by the cognate binding partner. Optionally, the cognate binding partner may be conjugated to a solid support, such as a resin in a column, in order to capture the complex. Suitable tags may include, but are not limited to a FLAG-tag, a 3×FLAG-tag, a His-tag, a Strep-tag, and a glutathione S-transferase tag. After the complex is bound by the cognate binding partner (e.g., which optionally is bound to a solid support such as a column resin), the complex may be washed in order to purify the complex and identify the ribosome associated with the complex.

The disclosed methods typically include an enriching step. The enriching step may include (i) recovering a subpopulation of rRNAs in assembled mutated ribosomes having translational activity (e.g., as obtained through the aforementioned partitioning step); (ii) converting the subpopulation of rRNAs to form a plurality of rRNA templates; and (iii) amplifying the plurality of rRNA templates (e.g., via performing RT-PCR). The amplified plurality of rRNA templates may be utilized to generate a new library of mutated rRNA templates for the disclosed methods. The steps of the disclosed methods (i.e., steps (a)-(c) as aforementioned) may be executed in a reiterative manner, for example, to simulate evolution of the library of mutated rRNA templates and converge the mutated rRNA templates.

The disclosed methods may be performed under a defined condition. For example, the methods may be performed under a defined condition in order to select for ribosomes that are translationally active under the defined condition. Suitable defined conditions may include, but are not limited to, a defined temperature or temperature range, a defined pH or pH range, a redox environment, or the presence of one or more additives (e.g., one or more antibiotics, in order to identify ribosomes that are translationally active in the present of the antibiotic, and hence, resistant to the antibiotic).

In a second aspect, components and compositions are disclosed, for example, components and compositions for performing the disclosed methods. The disclosed components and compositions may include polynucleotides, such as polynucleotide vectors such as ribosome display vectors. In some embodiments, the ribosome display vectors include: (a) a reporter gene encoding at least the beginning of an open reading frame (i.e., at least the 5' end of an open reading frame); (b) a promoter element operably linked to the 5' end of the reporter gene and configured to transcribe mRNA encoding the reporter gene; (c) a spacer element operably linked to the 3' end of the reporter gene and lacking a stop codon in frame with the open reading frame of the reporter gene; and (d) a self-cleaving ribozyme element operably linked 3' to the spacer element and configured to generate a run-off transcript comprising the open reading frame of the reporter gene. As such, the ribosome display vector may include, reading from 5'→3', as follows: 5'-promoter element→reporter gene→3'-spacer element→3'-self-cleaving ribozyme element.

The 3' spacer element typically has a length that is sufficient to provide for a ribosome exit tunnel. For example, the 3'-spacer element may be at least 10, 15, 20, 25, 30, 35, 40, 45, 50 nucleotides or longer.

The 3'-self-cleaving ribozyme element typically cleaves the nascent RNA and generates a run-off transcript. In some embodiments, the self-cleaving ribozyme element comprises a hammerhead self-cleaving ribozyme.

The ribosome display vector typically includes a reporter gene encoding a reporter molecule. The reporter gene may encode at least a portion of a binding partner. For example, the reporter gene may encode at least a portion of a binding partner encoded in frame with the beginning of the open reading frame of the reporter gene. Suitable binding partners may include peptide tags (e.g., a FLAG-tag, a 3×FLAG-tag, a His-tag, a Strep-tag, and a glutathione S-transferase tag).

In a third aspect, methods for identifying an engineered and/or modified E. coli ribosome having functional activity in the presence of an antibiotic. The methods may include the following steps: (a) performing an integrated ribosome synthesis assembly and translation (iSAT) reaction (e.g., as disclosed herein) with a library of mutated rRNA templates (e.g., as disclosed herein) and a ribosome display reporter template (e.g., as disclosed herein) in the presence of an antibiotic; and (b) partitioning a subpopulation of rRNAs in assembled mutated ribosomes having translational activity in the presence of the antibiotic from a remainder population of mutated rRNAs present in the iSAT reaction; and (c) enriching the partitioned subpopulation of rRNAs in assembled mutated ribosomes having translational activity in the presence of the antibiotic to identify the engineered and/or modified E. coli ribosome having functional activity in the presence of the antibiotic. In the disclosed methods, the steps (a)-(c) may be executed in a reiterative manner. Suitable antibiotics for the disclosed methods may include any antibiotic that inhibits translation, and in particular, ribosomal activity associated required for translation. Suitable antibiotics may include, but are not limited to clindamycin.

In a fourth aspect, an antibiotic-resistant ribosome is described. The antibiotic-resistant ribosome includes a product produced by the aforementioned methods for identifying an engineered and/or modified E. coli ribosome having functional activity in the presence of an antibiotic.

In a fifth aspect, kits comprising one or more components for performing the aforementioned methods are disclosed. The kits may comprise one or more components for performing an iSAT reaction as disclosed herein. The kits may comprise one or more components for performing RISE reaction as disclosed herein. For example, the disclosed kits may comprising one ore more components including a ribosome display vector as disclosed herein.

The methods and/or compositions disclosed herein may be practiced and/or prepared by practicing and/or modifying methods and compositions in the art. (See, e.g., Fritz et al., "Implications of macromolecular crowding and reducing conditions for in vitro ribosome construction," Nucl. Acids Res. 2015 May 19; 43(9):4774-84; Liu et al., "Characterizing and alleviating substrate limitations for improved in vitro ribosome constructions," ACS Synth. Biol. 2015 Apr. 17; 4(4):454-62; Fritz et al., "The impact of transcriptional tuning on in vitro integrated rRNA transcription and ribosome construction," Nucl Acids Res. 2014 June; 42(10): 6774-85; Jewett et al., "In vitro integration of ribosomal RNA synthesis, ribosome assembly, and translation," Mol Syst Biol. 2013 Jun. 25; 9:678; and Fritz et al., "Biology by design: from top to bottom and back," J Biomed Biotechnol. 2010; 2010:232016; the contents of which are incorporated herein by reference in their entireties).

Cell-Free Protein Synthesis (CFPS)

The disclosed subject matter relates in part to methods, systems, components, and compositions for cell-free protein synthesis. Cell-free protein synthesis (CFPS) is known and has been described in the art. (See, e.g., U.S. Pat. Nos. 6,548,276; 7,186,525; 8,734,856; 7,235,382; 7,273,615; 7,008,651; 6,994,986 7,312,049; 7,776,535; 7,817,794; 8,298,759; 8,715,958; 9,005,920; U.S. Publication No. 2014/0349353, and U.S. Publication No. 2016/0060301, the contents of which are incorporated herein by reference in their entireties). A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Platforms for Preparing Sequence Defined Biopolymers

An aspect of the invention is a platform for preparing a sequence defined biopolymer of protein in vitro. The platform for preparing a sequence defined polymer or protein in vitro comprises a cellular extract from the GRO organism as described above. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in Application No. PCT/US2015/033221 to Michael C. Jewett et al., entitled TETHERED RIBOSOMES AND METHODS OF MAKING AND USING THEREOF, filed 29 May 2015, and now published as WO2015184283, and U.S. patent application Ser. No. 15/363,828, to Michael C. Jewett et al., entitled RIBOSOMES WITH TETHERED SUBUNITS, filed on Nov. 29, 2016, and now published as U.S. Patent Application Publication No. 2017/0073381, on Mar. 16, 2017, the contents of which are incorporated by reference. In certain embodiments, one or more orthogonal components may be prepare in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture).

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., form about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Methods for Preparing Proteins and Sequence Defined Biopolymers

An aspect of the invention is a method for cell-free protein synthesis of a sequence defined biopolymer or protein in vitro. The method comprises contacting a RNA template encoding a sequence defined biopolymer with a reaction mixture comprising a cellular extract from a GRO as described above. Methods for cell-free protein synthesis of a sequence defined biopolymers have been described [1, 18, 26].

In certain embodiments, a sequence-defined biopolymer or protein comprises a product prepared by the method or the platform that includes an amino acids. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. An unnatural amino acids may also be referred to as a non-standard amino acid (NSAA) or non-canonical amino acid. In certain embodiments, a sequence defined biopolymer or protein may comprise a plurality of unnatural amino acids. In certain specific embodiments, a sequence defined biopolymer or protein may comprise a plurality of the same unnatural amino acid. The sequence defined biopolymer or protein may comprise at least 5, at least 10, at least 15, at least 20, at least 25, at least 30, at least 35, or at least 40 or the same or different unnatural amino acids.

Examples of unnatural, non-canonical, and/or non-standard amino acids include, but are not limited to, a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenyl-alanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 24ufa24hor, phosphono, phos-phine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radio-active amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α,α disubstituted amino acid; a β-amino acid; a γ-amino acid, a cyclic amino acid other than proline or histidine, and an aromatic amino acid other than phenyl-alanine, tyrosine or tryptophan.

The methods described herein allow for the preparation of sequence defined polymers that comprise non-natural amino acids or non-amino acids as monomers. The methods described herein allow for preparation of polymers such as polyolefin polymers, aramid polymers, polyurethane polymers, polyketide polymers, conjugated polymers, D-amino acid polymers, β-amino acid polymers, γ-amino acid polymers, δ-amino acid polymers, ε-amino acid polymers, ζ-amino acid polymers polycarbonate polymers, and benzoic acid polymers.

The methods described herein allow for preparation of sequence defined biopolymers or proteins with high fidelity to a RNA template. In other words, the methods described herein allow for the correct incorporation of unnatural, non-canonical, and/or non-standard amino acids as encoded by an RNA template. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and a product prepared from the method includes at least 80%, at least 85%, at least 90%, at least 95%, or 100% of the encoded unnatural, non-canonical, and/or non-standard amino acids.

The methods described herein also allow for the preparation of a plurality of products prepared by the method. In certain embodiments, at least 80%, at least 85%, at least 90%, at least 95%, or at least 98% of a plurality of products prepared by the method are full length. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and at least 80%, at least 85%, at least 90%, at least 95%, or at least 98% of a plurality of products prepared by the method include 100% of the encoded unnatural, non-canonical, and/or non-standard amino acids.

In certain embodiments, the sequence defined biopolymer or the protein encodes a therapeutic product, a diagnostic product, a biomaterial product, an adhesive product, a biocomposite product, or an agricultural product.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Illustrative Embodiments

The following Embodiments are illustrative and are not intended to limit the scope of the claimed subject matter Embodiment 1. A comprehensive set of ribosome active site variants for use in ribosome engineering as described herein.

Embodiment 2. The ribosome active site variants of claim 1 comprising one or more mutations in the ribosomal RNA (rRNA) of the ribosome.

Embodiment 3. The ribosome active site variants of claim 1 comprising one or more mutations in the peptidyl transferase center (PTC) of 23 S rRNA.

Embodiment 4. A method of synthesizing sequence defined polypeptides and polymers using one or more of the ribosome active site variants as recited in claims 1-3 and/or as described herein.

Embodiment 5. A method of synthesizing sequence defined polypeptides and polymers comprising non-natural, non-α-amino acid monomers (NNAs), which may include, but are not limited to sequence-defined polyolefin polymers, aramid polymers, polyurethane polymers, polyketide polymers, conjugated polymers, D-amino acid polymers, β-amino acid polymers, γ-amino acid polymers, δ-amino acid polymers, ε-amino acid polymers, ζ-amino acid polymers polycarbonate polymers, and benzoic acid polymers, using one or more of the ribosome active site variants as recited in claims 1-3 and/or as described herein Embodiment 6. The method of claim 4 or 5 comprising using multi ribosome active site variants as recited in claims 1-3 and/or as described herein.

Embodiment 7. The method of any of claims 4-6 performed in vitro or in a cell-free system.

Embodiment 8. The method of any of claims 4-7 performed in vivo or in a cell.

Embodiment 9. A method of using an in vitro, or cell-free, ribosome synthesis and assembly platform to discover mutant ribosomes capable of making polymers containing non natural, non-α-amino acid monomers.

EXAMPLES

The following Examples are illustrative and are not intended to limit the scope of the claimed subject matter.

Example 1—In Vitro Discovery and Characterization of Functional E. coli 23S rRNA Nucleotide Mutations for Engineering the Ribosome Abstract As the catalytic workhorse of the bacterial cell, the Escherichia coli (E. coli) ribosome is a 2.4 MDa molecular machine that polymerizes α-amino acids into polypeptides using information encoded in messenger RNAs (mRNAs). This macromolecular machine is composed of two distinct subunits, the large (50S) subunit and the small (30S) subunit. The 50S subunit is composed of 33 r-proteins as well as a 23S rRNA and a 5S rRNA. This subunit is responsible for accommodating tRNA-amino acid monomers, catalyzing polypeptide synthesis, and excreting polypeptides. Importantly, the active site of the ribosome, or the peptidyl transferase center (PTC), resides in domain V of the 23S rRNA within the 50S subunit. The PTC is composed solely of conserved, catalytic rRNA nucleotides, making the ribosome an ancient ribozyme. Understanding the mutational flexibility of the ribosome's PTC has the potential to permit extensive engineering and evolution of these nucleotides for the processing of unique non-biological monomers. However, a comprehensive functional mutational analysis for every PTC nucleotide is still absent. This gap in knowledge is exacerbated by the highly-conserved nature and functional importance of many active site nucleotides. Characterization of mutations at these locations has proven difficult as nucleotide changes confer severe deleterious phenotypes. Thus, beyond insights gained from crystal structures and a limited set of biochemical mutation analyses, we currently lack direct mutational and functional knowledge for many key nucleotides in the ribosome's active site. Here, we have leveraged an integrated synthesis, assembly and translation (iSAT) platform to build and characterize every possible nucleotide mutation within the ribosome's active site (PTC-, A-, and P-loops). Using this system, we probed variant activity, kinetics, translation readthrough, assembly, and finally mapped activity onto structure. This work represents the first comprehensive mutational characterization and mapping of the 70S ribosome's active site and allowed us to identify permissible mutants that can be used to engineer the ribosome for the production of sequence defined polymers.

Applications

The applications for the disclosed technology include, but are not limited to: (i) probing and screening for new antibiotic resistant mutations in a ribosome (e.g., in the rRNA sequence or elsewhere in a ribosome); (ii) engineering and evolving new functionality in the active site of a ribosome; (iii) determining design rules for catalytic RNA; (iv) engineering minimal ribosomes; (v) understanding the most critical nucleotides (or alternatively, the dispensable nucleotides) within the active site of the ribosome.

Advantages

The advantages of the disclosed technology include, but are not limited to: (i) first comprehensive mutational map of the E. coli 70S ribosome active site (i.e., the peptidyltransferase center or "PTC"); (ii) Enablement of the identification of ribosomes with read-through errors as well as ribosomes with assembly defects; (iii) characterization of 180 different point mutations within the 70S rRNA active site, the majority of which have never before been characterized or studied; (iv) demonstration of the efficient design, synthesis, and characterization of ribosomal variants using a cell-free platform; (v) a standardized and high-throughput procedure for characterizing engineered ribosomal mutants with no wild type ribosome contamination; (vi) reduction in the time required to produce and purify ribosomal variants in a prokaryotic cell lysate from weeks to days, which could provide competitive advantage in commercialization of the technology; and (vii) identification of ribosomal variants that could be useful in future engineering efforts, antibiotic resistance studies, ribosome purification efforts and more.

Problems Addressed

While current ribosome peptidyl transferase center (PTC) studies present insight into active site nucleotide function, there still exist limitations and gaps in knowledge. First, current studies only examine a limited number of nucleotide mutations point mutations. Second, no PTC nucleotide mutation studies currently use highly active in vitro synthesized ribosomes that synthesize full-length proteins. Third, no PTC mutational studies have identified active site nucleotide changes that impact ribosome assembly and subunit association. And finally, no ribosomal mutational map exists to permit and facilitate the efficient engineering of the ribosome's active site for novel polymer synthesis.

A comprehensive mutational map of the ribosome's active site has the potential to address these limitations. Here, we demonstrate that using an in vitro *Escherichia coli* ribosome synthesis, assembly, and translation (iSAT) platform can be leveraged to build and test every possible single mutation within the PTC. This is carried out through coordinated in vitro transcription, ribosome assembly, and translation cell-free ribosome synthesis (iSAT) reactions lasting just 20 hours. Our mutational map has the potential to reduce process development and testing timelines for novel antibiotics that target the ribosome. Further, because we currently lack mutational data and information on most ribosomal active site nucleotides a comprehensive mutational map can be leveraged as a foundational resource for ribosome biochemists, cellular and molecular biologists, as well as engineers. Importantly, all the PTC nucleotide mutations in our mutational map have been studied using a standard set of biochemical assays, providing a homogenous set of data for every mutation. Additionally, because this comprehensive mutational map outlines mutational flexibility and characterizes its impact on peptide synthesis, this map could be used to prototype other engineered ribosomal multi-mutants. Specifically, computational efforts would greatly benefit from this map, as it may aid the efficient study of epigenetics within the ribosome's active site. Finally, this mutational map could be readily applied to ribosomal variants for the synthesis of various peptides, including precursors for therapeutic medicines and materials. This could be accomplished by identifying ribosomal mutants (single or multi-mutants) that are capable of accepting and processing diverse monomers more readily than the wild-type ribosome. Previous literature suggests that this map can be leveraged in this way, as multi-mutants used for beta-amino acid incorporation all exist in the ribosome's active site (work from the Hecht and Schepartz labs). This novel and comprehensive rRNA PTC mutational map has advantages for basic and synthetic/engineering biology.

No known comprehensive map of every functional *E. coli* 23 S rRNA active site mutation exists. There are previous studies that use biochemical strategies to address this problem, however, these studies focus on antibiotic resistance, and not overall activity. Additionally, the studies are limited to a very small set of nucleotides.

This novel comprehensive in vitro mutational map of the *E. coli* 70S active site has elucidated mutationally flexible and inflexible pockets of the active site, identified active site mutants that possess readthrough errors, and determined which active site mutants possess assembly issues. Using a cell-free ribosome synthesis assembly and translation (iSAT) system, we were able to address limitations of existing variant ribosome production, purification, and characterization, making it an attractive alternative or complementary strategy for engineering and evolving ribosomes in the future. In light of the growing interest to engineer translational machinery for the incorporation of abiological monomers, this comprehensive mutational map has the potential to be extremely valuable for research development, ribosome variant engineering, and ribosome evolution for efficient the synthesis of novel abiological proteins and polymers.

References

U.S. Pat. Nos. 5,478,730; 5,556,769; 5,665,563; 6,168,931; 6,518,058; 6,783,957; 6,869,774; 6,994,986; 7,118,883; 7,189,528; 7,338,789; 7,387,884; and 7,399,610; the contents of which are incorporated herein by reference in their entireties. U.S. Published Application Nos. 2012/0171720; 2016/0083688; 2017/0073381; and 2017/0306320; the contents of which are incorporated herein by reference in their entireties.

Example 2—Mutating the Ribosomal Peptidyl Transferase Center In Vitro

Title—Mutational Characterization and Mapping of the 70S Ribosome Active Site

Abstract

The synthetic capability of the *Escherichia coli* ribosome has attracted efforts to repurpose it for novel functions, such as the synthesis of polymers containing non-natural building blocks. However, efforts to repurpose ribosomes are limited by the lack of a complete peptidyl transferase center (PTC) active site mutational analyses to inform design. To address this limitation, we leverage an in vitro ribosome synthesis platform to build and test every possible single nucleotide mutation within the PTC-ring, A-loop and P-loop, 180 total point mutations. These mutant ribosomes were characterized by assessing bulk protein synthesis kinetics, fidelity, assembly, and structure mapping. Despite the highly-conserved nature of the PTC, we found that >85% of the PTC nucleotides possess mutational flexibility. Our work represents a comprehensive single-point mutant characterization and mapping of the 70S ribosome's active site. We anticipate that it will facilitate structure-function relationships within the ribosome and make possible new synthetic biology applications.

Introduction

Figure 2:
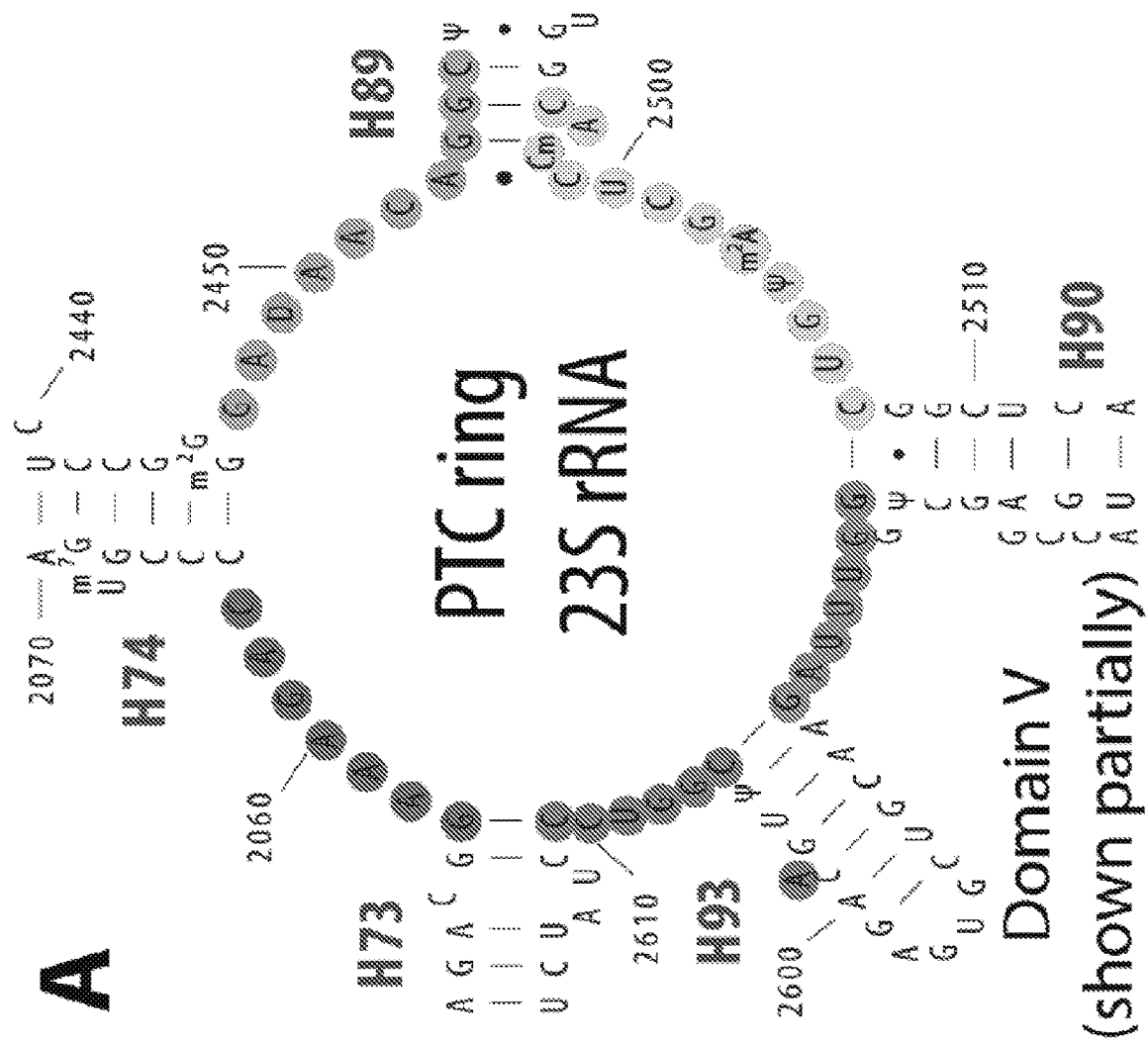
FIG. 2. The ribosome's peptidyl transferase center (PTC) is important for translation and can be studied in vitro. (A) Secondary structure and (B) crystal structure model of the PTC-ring nucleotides probed in this study. (C) Secondary structure and crystal structure model of the A- and P-loop nucleotides probed in this study.
Figure 2:
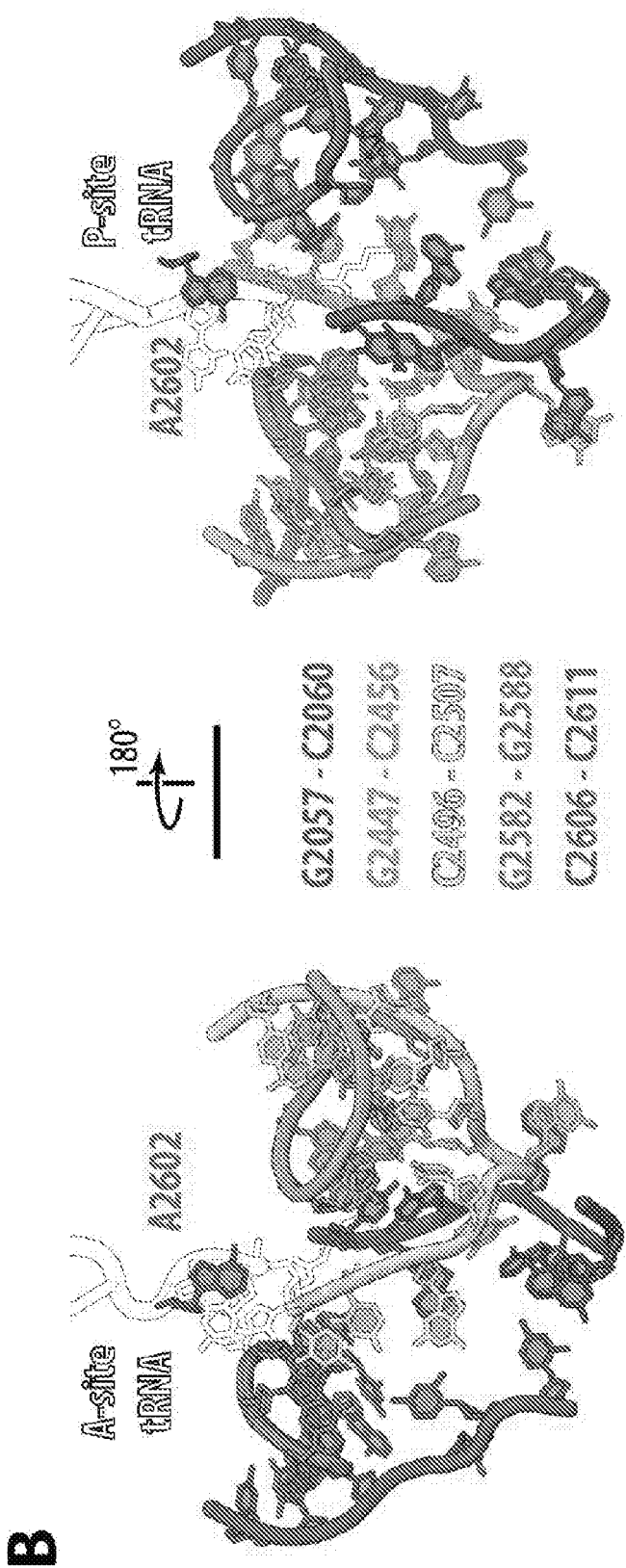
Figure 2:
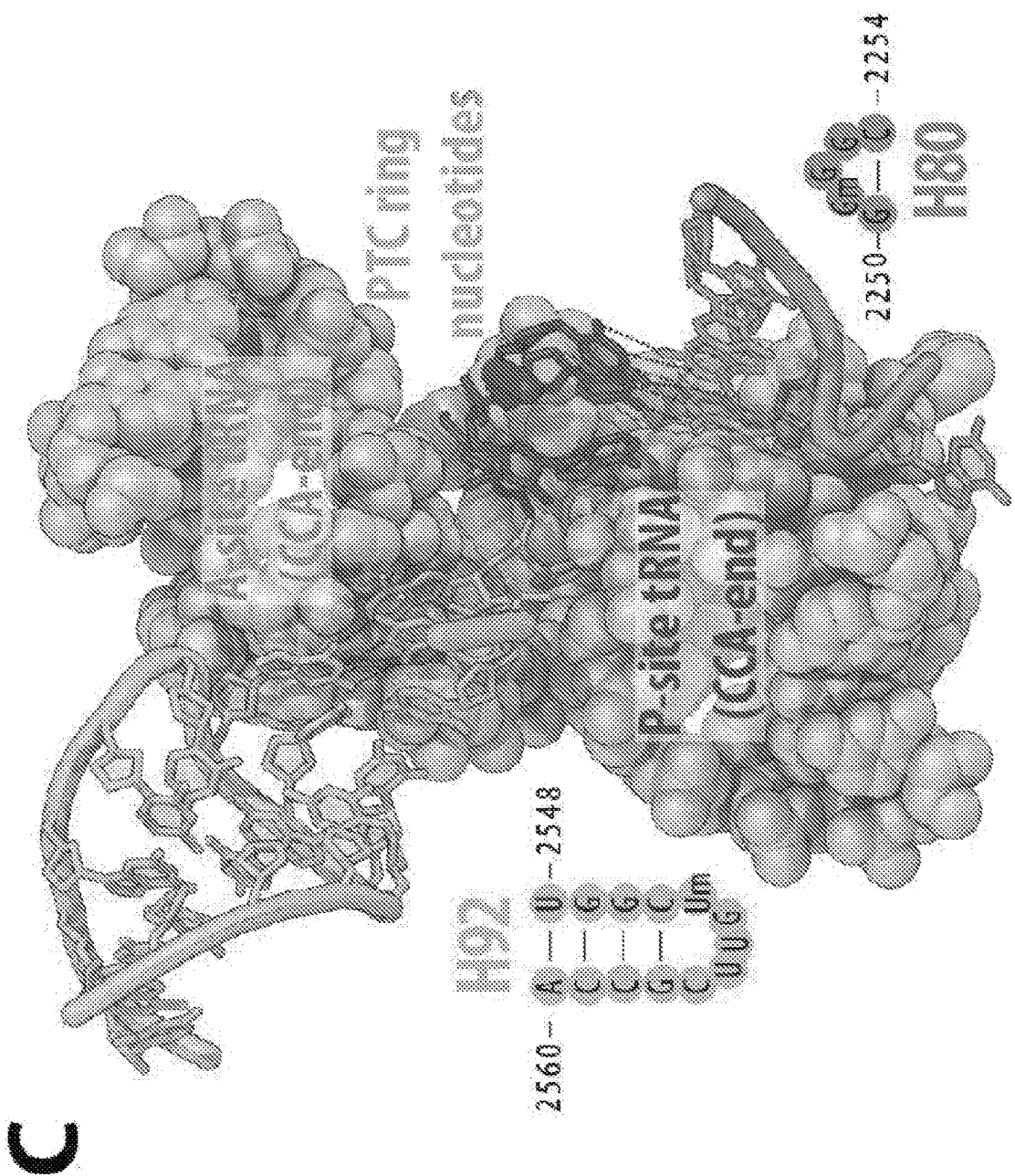

The *Escherichia coli* ribosome is the molecular machine that polymerizes α-amino acids into polypeptides using information encoded in messenger RNAs (mRNAs). This machine is composed of two distinct subunits: the large (50S) subunit, responsible for accommodating tRNA-amino acid monomers, catalyzing peptide bond formation, and excreting polypeptides, and the small (30S) subunit, primarily responsible for decoding the mRNA. The active site of the ribosome, or the peptidyl transferase center (PTC), residing in the 23S rRNA of the 50S subunit, is composed solely of conserved catalytic rRNA nucleotides, making the ribosome an ancient ribozyme (1). These rRNA nucleotides of the PTC play a key role in positioning the CCA ends of the aminoacyl (A)-site and peptidyl (P)-site tRNA monomers to catalyze peptide bond formation and facilitates peptide release (2). Sets of key rRNA nucleotides within the PTC are arranged as rings and loops, with the central PTC-ring, A-loop, and P-loop playing pivotal roles in translation (1,3,4) (FIG. 2). The central PTC-ring (defined in our study as G2057-C2063, G2447-C2456, C2496-C2507, G2582-G2588, A2602, and C2606-C2611) surrounds the A- and P-site tRNA monomers and has been implicated in antibiotic binding (5), tRNA positioning (6), and peptide stalling (7,8). As their names suggest, the A-loop (defined in our study as U2548-A2560) is essential in interacting with A-site tRNA during translation, while the P-loop (defined in our study as G2250-C2254) makes contacts with P-site tRNA (3,9-11). The A- and P-loops are co-located on either side of the central PTC-ring, above the peptide exit tunnel (FIG. 2).

Both in vivo and in vitro studies of the *E. coli* ribosome's active site have provided a foundational understanding of ribosome structure, function, and mechanism (12,13). However, we lack a comprehensive understanding of the PTC, in part, because a complete functional mutational analysis does not exist. This gap in knowledge is rooted in several challenges. One challenge, for example, includes insufficient high-throughput methods to synthesize and characterize a large number of ribosomal mutations. As a result, existing ribosomal mutation studies typically focus only on a few mutations at a time (i.e., one to six in depth characterizations per paper) (14,15), use characterization techniques that can be difficult to compare (spanning in vitro biochemistry, in vivo genetics, computational modelling, antibiotic resistance probing, and more), and sometimes examine different bacterial species. This has led to a segmented and heterogeneous image of the ribosome's mutational space (Table 2). Another challenge is the highly-conserved nature and functional importance of many active site nucleotides. Characterization of mutations at these locations has proven difficult as nucleotide changes confer deleterious phenotypes (16-18). Thus, beyond insights gained from crystal structures and a limited set of biochemical mutation analyses, we currently lack direct mutational and functional knowledge for many key nucleotides in the ribosome's active site. A comprehensive mutational map of the ribosome's active site would facilitate antibiotic resistance studies (16), active site and rRNA engineering efforts (19-21), and substantially build on our current understanding of structure-function relationships within the ribosome (19).

To circumvent cell-viability constraints (22), a cell-free (23-27), or in vitro, ribosome synthesis approach could be used for identifying structurally and functionally critical sites in the ribosome useful for both basic biology and future ribosome engineering advances (28). For example, the elegant "atomic mutagenesis" approach developed by Polacek and colleagues has helped unravel the detailed contributions of rRNA nucleotides in protein synthesis (29-31). In previous work, we developed and optimized a different approach for use with *Escherichia coli* ribosomes; the integrated synthesis, assembly, and translation (iSAT) platform for the in vitro construction and characterization of ribosomes (32-35). The iSAT platform leverages a ribosome-free S150 crude extract to enable the efficient transcription of template-derived rRNA. Importantly, iSAT co-activates the processes of rRNA synthesis and processing, ribosome assembly, and translation in a one-pot reaction, mimicking natural in vivo processes. The iSAT system therefore provides a unique and powerful approach for the interrogation and manipulation of *E. coli* ribosomes in a cell-like environment. This system contrasts with previous approaches for in vitro ribosome reconstitution, which have played important roles in elucidating our understanding of the ribosome (15), but are unable to incorporate synthetic in vitro transcribed 23S rRNA of the large subunit into highly active *E. coli* ribosomes (28,30,36-39). Key advantages of this platform include no wild-type ribosome contamination, facile and rapid mutant construction and testing, and a reaction environment that closely resembles the cell.

In this work, we use the in vitro iSAT platform to rapidly characterize ribosomal active site mutations. Specifically, we probed all nucleotides in the catalytically critical PTC-ring, A-loop, and P-loop by: i) constructing single point mutations at every possible rRNA position within these loops (180 total mutations); ii) testing their translational activity in vitro; iii) assaying translation read-through of a premature stop codon as a proxy for fidelity (14,40-42) and; iv) characterizing ribosomal assembly. A graphical abstract of the methods disclosed here is provided as FIG. 1. Finally, we analyzed our mutational activity data in the context of the three-dimensional ribosome structure by mapping our findings directly onto the crystal structure (FIG. 2). We report the first, to our knowledge, comprehensive molecular dissection of the ribosome's active site in the context of mutational flexibility, and the development of a high-throughput and standardized workflow for rapidly constructing and characterizing rRNA mutants. We envision these findings to be a stepping stone for both basic biologists and engineers to target, study, and engineer single or multiple ribosomal nucleotides.

Materials and Methods

Plasmid Construction. The 7,300-bp plasmid pT7rrnB carries an *Escherichia coli* rRNA operon, rrnB, under the control of the T7 promoter and the ampicillin resistance gene as a selective marker. All ribosomal mutant plasmids are derivatives of pT7rrnB carrying single point mutations in the 23S rRNA gene. Briefly, site-directed mutagenesis was used to construct each individual point mutant. Nucleotide point mutations were introduced into primers and amplified using pT7rrnB as a template for PCR amplification. PCR products were blunt end ligated, transformed into DH5a using electroporation, and plated onto LB-agar/ampicillin plates at 37° C. Plasmid was recovered from resulting clones and sequence confirmed.

Similarly, premature stop codon readthrough constructs were generated by introducing a premature stop sequence (UAG, UGA, of UAA) into primers, and amplified using pJL1-sfGFP as a template for PCR amplification. PCR products were blunt end ligated, transformed into DH5a using electroporation, and plated onto LB-agar/Kanamycin plates at 37° C. Readthrough controls were generated reporter constructs by introducing all possible stop codon permutations (UGA, UAA, and UAG) at various positions within the reporter (FIG. 4A). All constructs were verified by DNA sequencing.

Sequence alignment and analysis. A dataset consisting of 1,614 pre-aligned and phylogenetically arranged 23S sequences were downloaded from the All Species Living Tree Project (version 123, compiled using the SILVA reference database LSUref123) (43). This dataset included the *E. coli* sequence (AJ278710) that was used as a reference to find regions of interest in the full species alignment using custom scripts (available at https://github.com/adamhockenberry/23s-alignment-LTP). All species were used in visualizations, but entropy calculations included only analysis of ungapped sequences. Specifically, for each position in the alignment of a region of interest we first removed any sequence where that position was denoted by a '-' character. With the remaining sequences we calculated the entropy values (H) as:

$$H = -\Sigma_{i \in (A,U,G,C)} p_i \log(p_i)$$

where the probability of nucleotide i ($p_i$) comes from the counts of nucleotide i divided by the number of all non-gapped sequences at that position. In this formulation, H has a minimum of 0 when all sequences in an alignment column are one nucleotide and a maximum of ~1.386 when all nucleotides are equally likely (i.e. occurring with a probability of 0.25).

Figure 13:
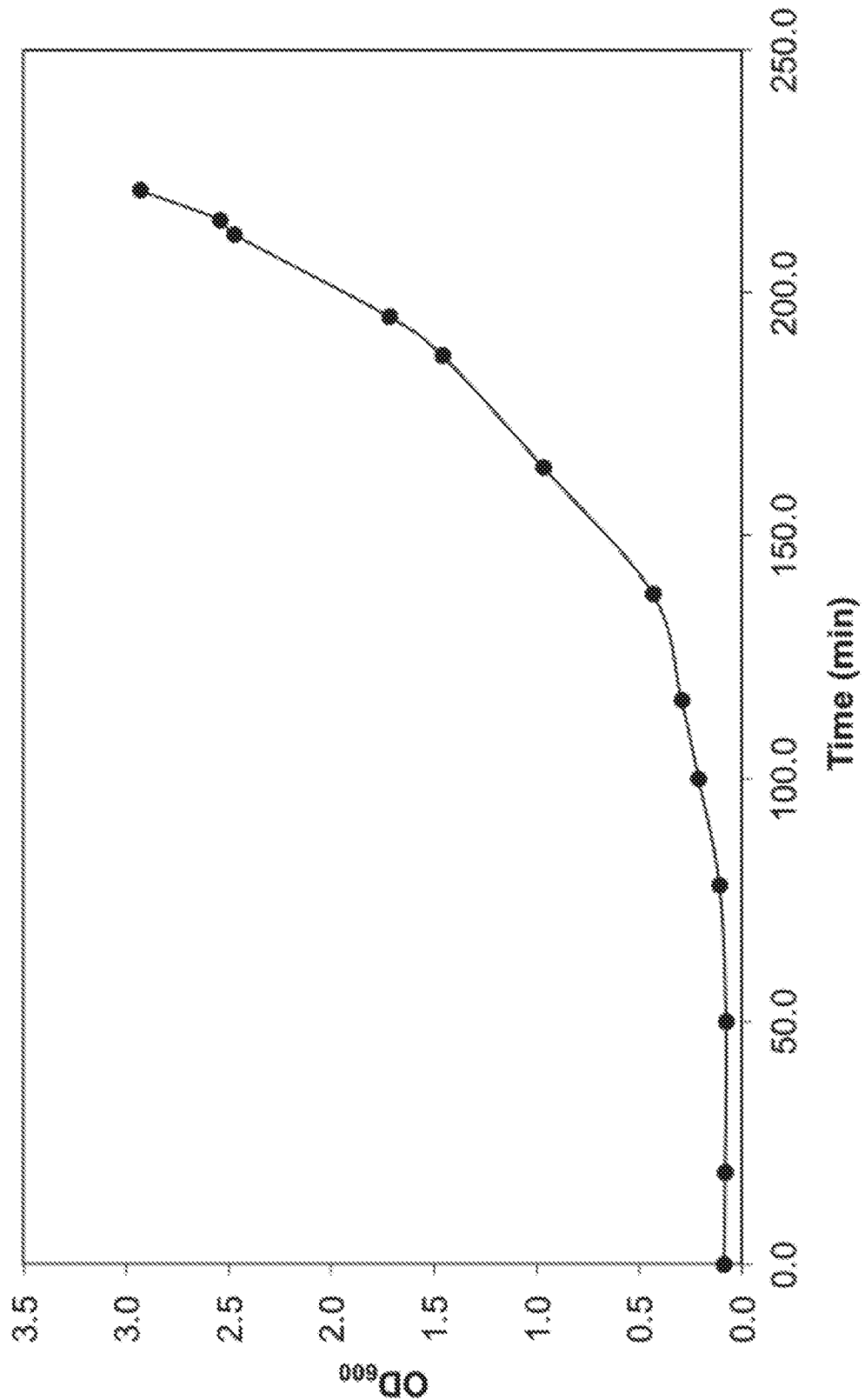
FIG. 13. Growth curve of E. coli MRE600 strain used in this study. Cells were grown in 10 L of 2×YTPG media and harvested from the fermenter at OD=2.9-3.1. Cells were grown at 37 C, as previously reported.

Strain culture and harvest. *E. coli* cells for S150 extract and TP70 preparation were grown in 10 L of 2×YPTG in a fermenter (Sartorius) (FIG. 13). MRE600 strain was grown at 37° C. Cells were harvested at $OD_{600}$=2.8-3.0, washed twice in S150 lysis buffer (20 mM Tris-chloride pH 7.2 at 4° C., 100 mM ammonium chloride, 10 mM magnesium chloride, 0.5 mM EDTA, 2 mM DTT), pelleted, and flash frozen at −80° C. using liquid nitrogen for storage. Buffer was added at a ratio of 5 mL of buffer per 1 g of cells. 200 µL of Halt Protease Inhibitor Cocktail (Thermo Fisher Scientific Inc.) and 75 µL RNase Inhibitor (Qiagen) were added for every 4 g of cells in the suspension. The cells were lysed at approximately 20,000 psi with an EmulsiFlex-C3 homogenizer (Avestin). An equivalent dose of RNase Inhibitor and 3 µL of 1M DTT per millilitre were added to the lysate prior to two clarification spins at 30,000 g and 4° C. for 30 min. Supernatant equivalent to S30 crude extract was recovered and gently layered into Ti45 ultracentrifuge tubes on top of an equivalent volume of sucrose cushion, buffer B (20 mM Tris-HCl (pH 7.2 at 4° C.), 100 mM $NH_4Cl$, 10 mM $MgCl_2$, 0.5 mM EDTA, 2 mM DTT, 37.7% sucrose). Samples were then centrifuged (at 35000 rpm in Ti70 rotor) and 4° C. for 20 h. Supernatant was recovered for S150 extract, and the remaining clear ribosome pellet was gently washed and resuspended in buffer C (10 mM Tris-OAc (pH 7.5 at 4° C.), 60 mM $NH_4Cl$, 7.5 mM $Mg(OAc)_2$, 0.5 mM EDTA, 2 mM DTT). Concentration of resuspended ribosomes was determined from A260 NanoDrop readings (1 A260 unit of 70S=24 pmol 70S (44)). Ribosomes were then aliquoted and flash-frozen for use as purified 70S ribosomes and for purification of native rRNA and r-proteins.

Figure 14:
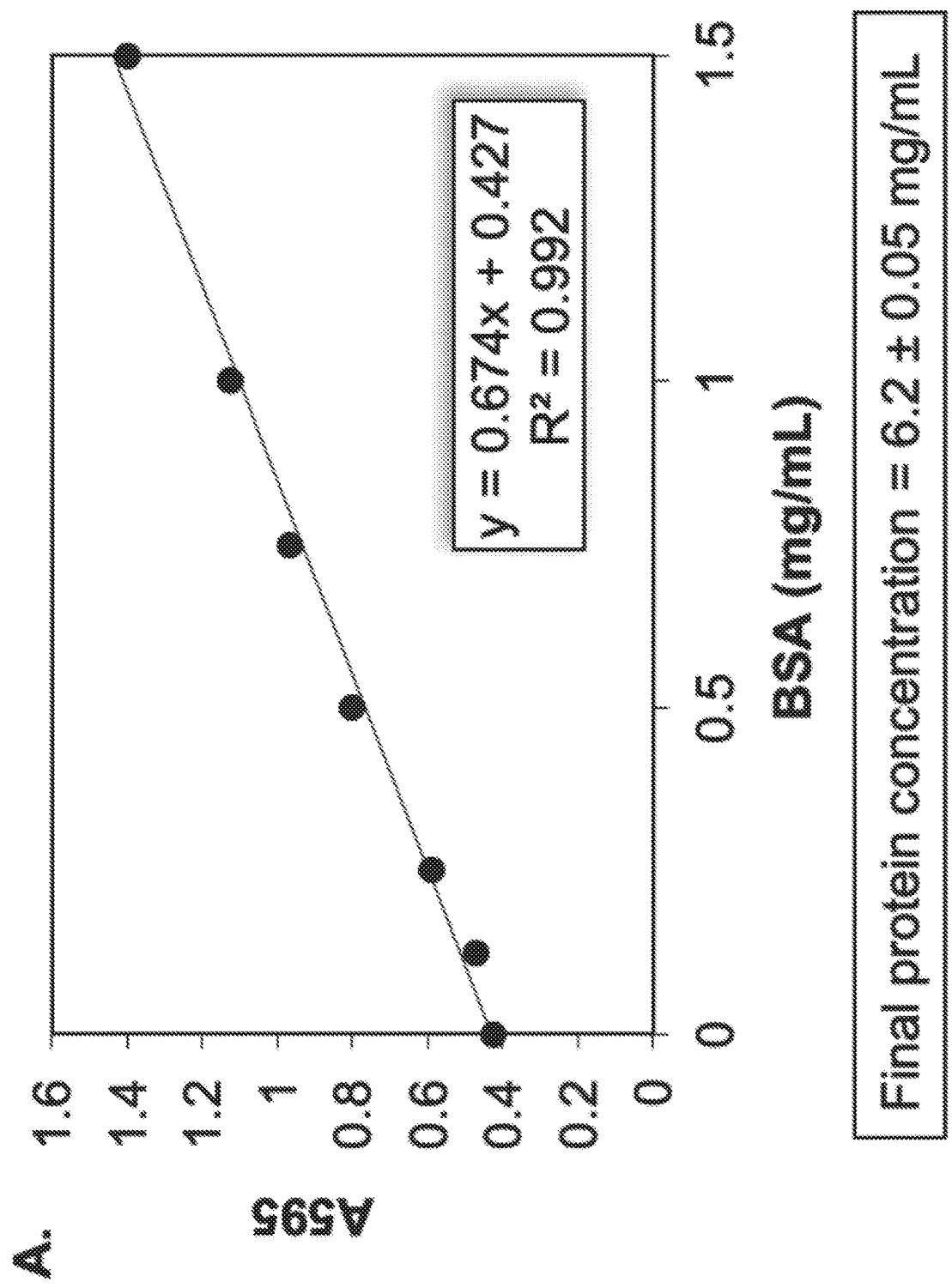
FIG. 14. Extract testing and optimization. (A) Protein concentration of S150 extract used in this paper. Values represent average concentrations as determined by Bradford assay with bovine serum albumin (BSA) as a standard. Error bars represent one standard deviation from the mean for triplicate measurements. (B) Magnesium optimization of S150 extract for reporter protein synthesis in iSAT reactions. Standard 15 μL batch reactions were performed at 37° C. for 20 h, with varying magnesium glutamate concentrations the S150 extract used. Total protein concentration of each S150 extract added to reactions was standardized at 3.6 mg mL-1. Synthesis of active wild-type (wt) sfGFP was measured after 20 h using fluorescence. Optimal magnesium glutamate concentrations for iSAT reactions was determined to be: 13 mM for MRE600. This concentration was then used for subsequent experiments. Values represent averages and error bars represent one standard deviation from the mean, with n≥3 for n number of independent reactions.
Figure 14:
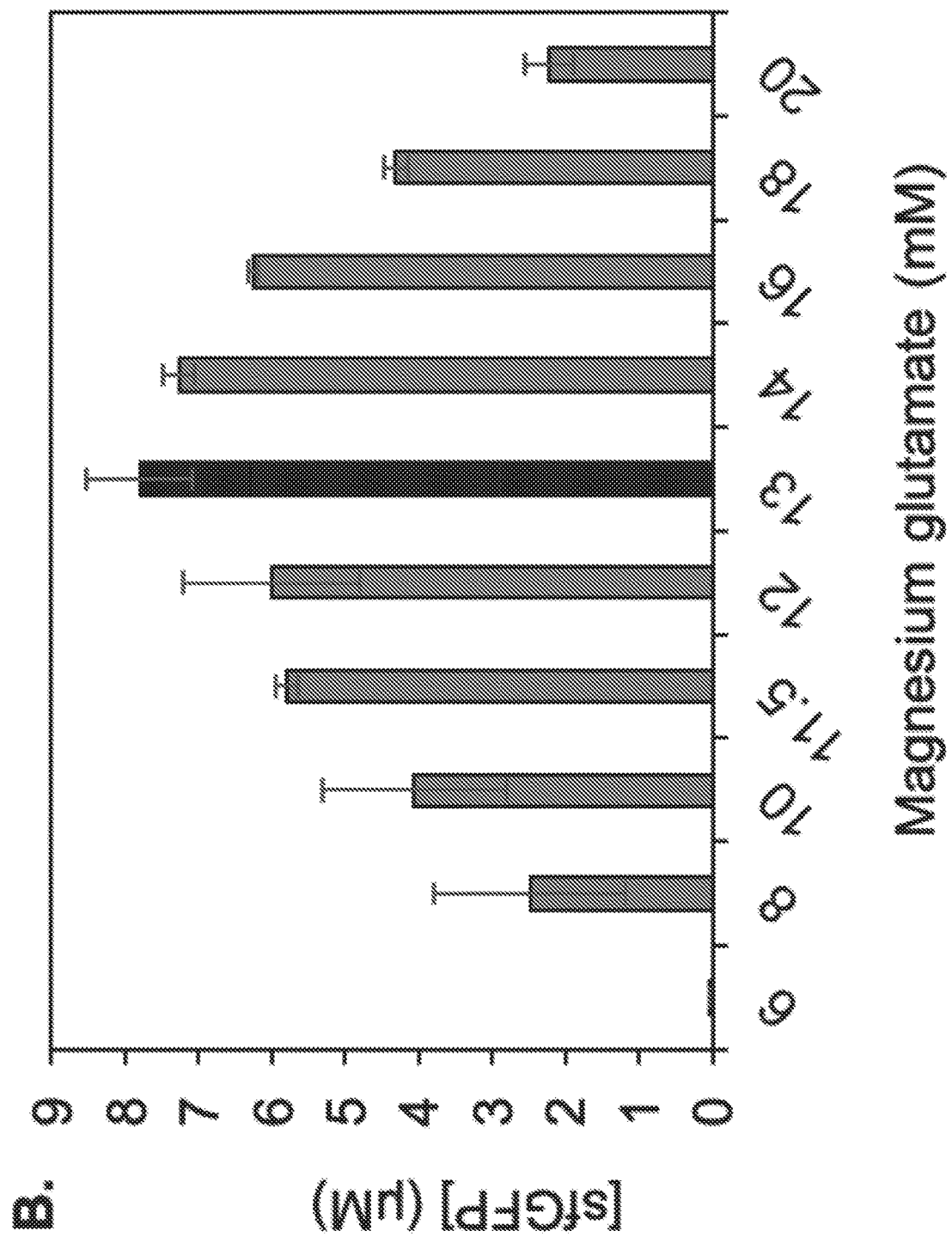

Component preparation. S150 crude cell-free extracts, *E. coli* 70S ribosomes, total protein of 70S ribosomes (TP70) and T7 RNA polymerase (RNAP) were prepared as previously reported (33,45). S150 and TP70 were prepared from MRE600 cells. Protein concentrations of each S150 extract were measured using Bradford assay with bovine serum albumin (BSA) as a standard.

iSAT reactions. iSAT reactions of 15 µL were set-up as previously described (33). Briefly, reactions were prepared in polymerase chain reaction tubes with optically clear flat caps and incubated at 37° C. in a CFX96 real-time thermal cycler (Bio-Rad). iSAT reactions contained reporter protein plasmids encoding superfolder GFP (sfGFP). Green fluorescence of sfGFP was monitored using the CFX96 real-time thermal cycler as (excitation: 450-490 nm, emission: 510-530 nm). Additives were included at the described final concentrations. Specifically, crowding agent (2% PEG-6000) and reducing agent (2 mM DTT) were added to each reaction. iSAT reactions for 5150 extracts were optimized for concentrations of magnesium glutamate to maximize reaction productivity and minimize consumption of parts (FIG. 14). sfGFP quantification was performed as previously reported (32), using measurements of relative fluorescence units (RFU) from CFX96 real-time thermal cycler (BioRad, Hercules, Calif.) and BioTek Synergy 2 plate reader (Winooski, Vt.). RFU values were converted to molar concentration using a linear standard curve made in-house by expressing $^{14}$C-leucine labelled sfGFP in *E. coli* PANOx CFPS reactions and relating RFUs to trichloracetic acid precipitable soluble protein yield.

Figure 15:
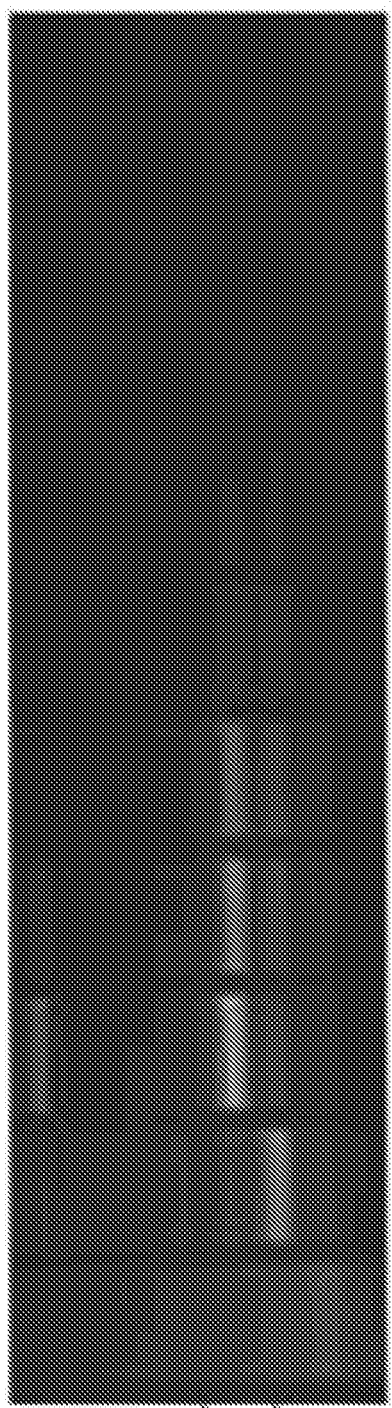
FIG. 15. Gel electrophoresis analysis of WT and mutant iSAT ribosome profiles following sucrose density centrifugation. A 120 μL iSAT reaction possessing a reporter plasmid was analyzed by ribosome profiling in a 10-40% sucrose gradient. The resulting 500 μL-1 mL fractions were run by electrophoresis on a 1% agarose gel (one fraction per well). The rRNA contained within each fraction was used to confirm the predominate peaks as containing 30S subunits, 50S subunits, or 70S ribosomes.
Figure 15:
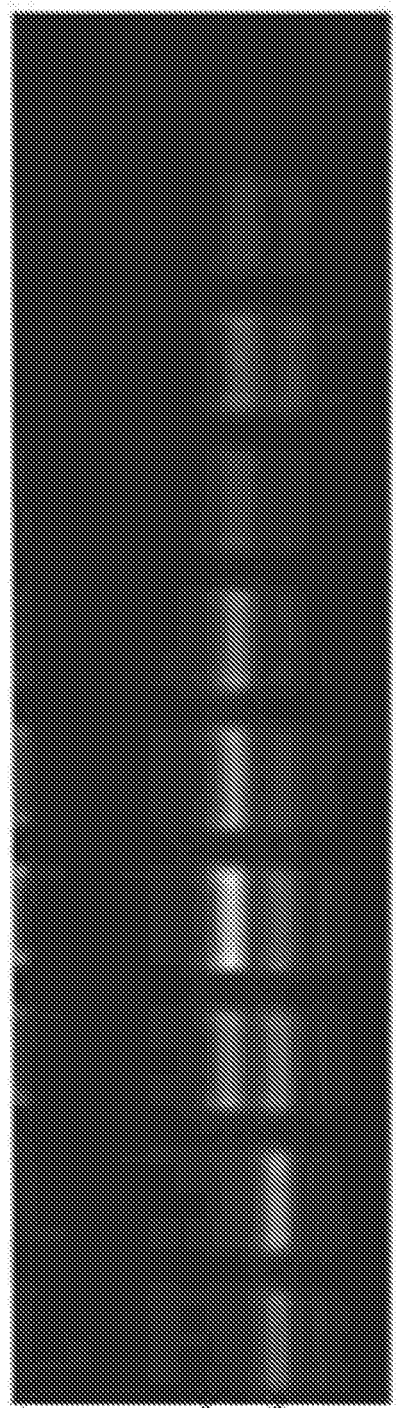
Figure 15:
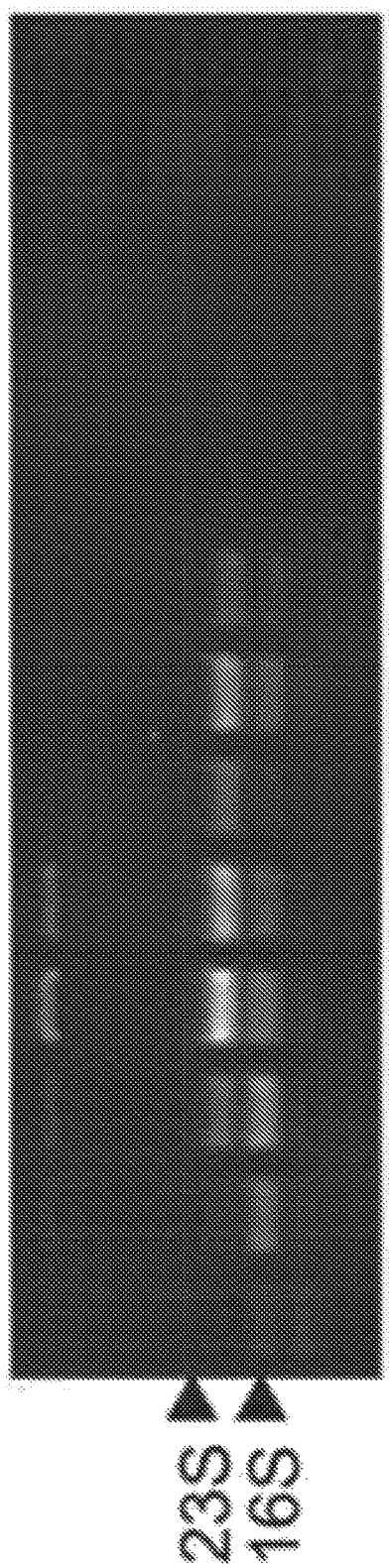
Figure 15:
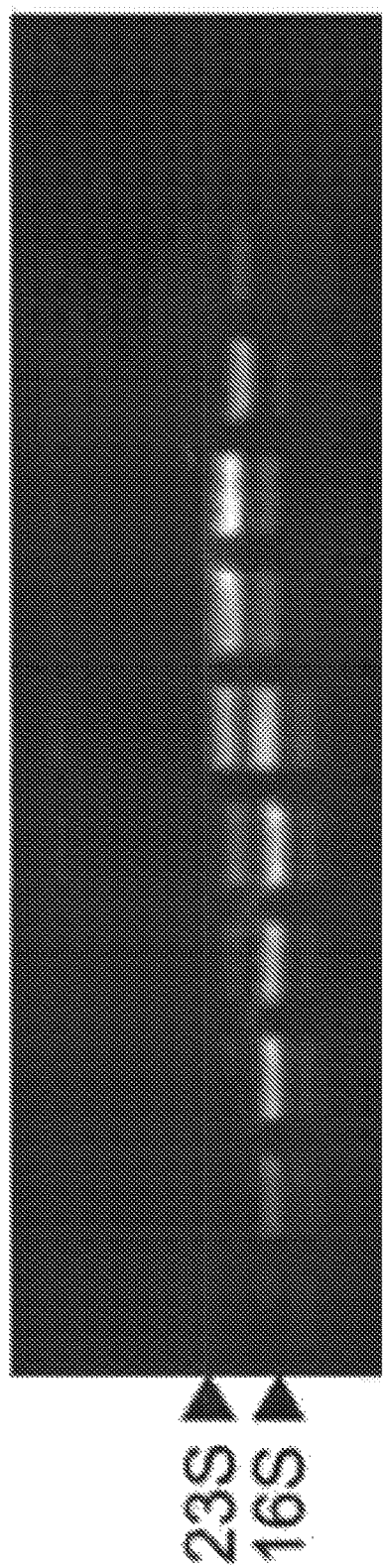
Figure 15:
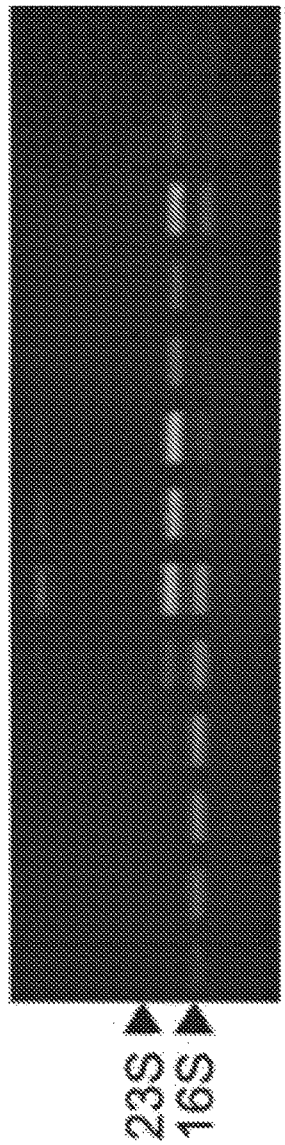
Figure 15:
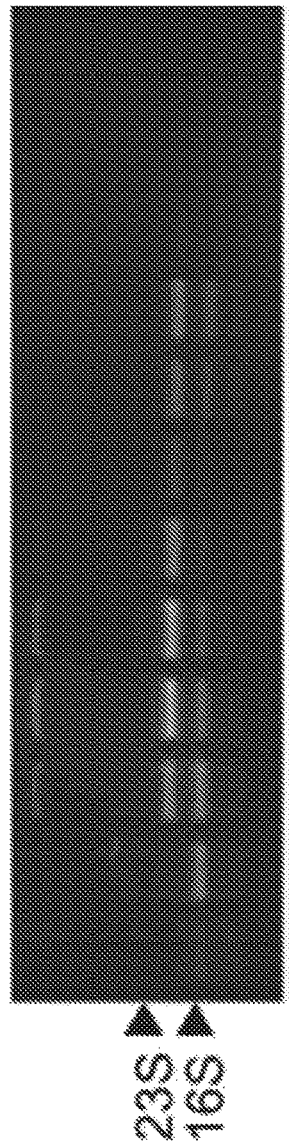
Figure 15:
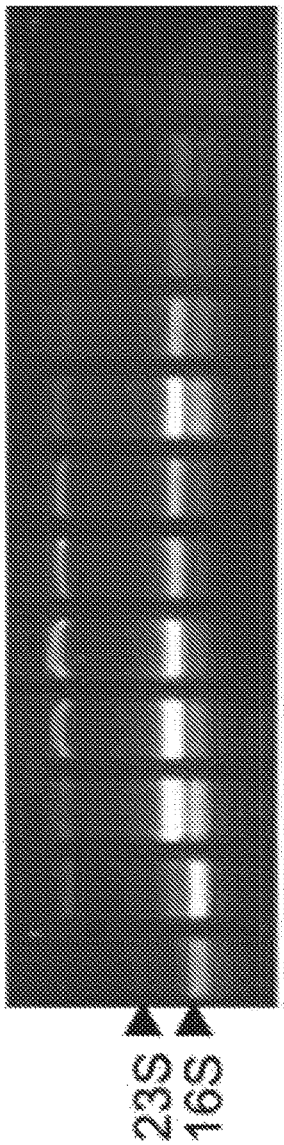

Ribosome sedimentation analysis. Sucrose gradients were prepared from Buffer C (10 mM Tris-OAc (pH=7.5 at 4° C.), 60 mM $NH_4Cl$, 7.5 mM $Mg(OAc)_2$, 0.5 mM EDTA, 2 mM DTT) with 10 and 40% sucrose in SW41 polycarbonate tubes using a Biocomp Gradient Master. Gradients were placed in SW41 buckets and chilled to 4° C. Meanwhile, approximately 7-8×15 µL iSAT reactions were prepared and incubated at 37° C., for 2 hours. Reactions were pooled and 90-120 µL of iSAT reactions were carefully loaded onto chilled gradients. The gradients were ultra-centrifuged to 22,500 rpm for 17 hours at 4° C., using an Optima L-80 XP ultracentrifuge (Beckman-Coulter) at medium acceleration and braking (setting of 5 for each). Gradients were analysed with a BR-188 Density Gradient Fractionation System (Brandel) by pushing 60% sucrose into the gradient at 0.75 ml/min (at normal speed). Traces of A254 readings versus elution volumes were obtained for each gradient, with readings adjusted to match baselines based on blank sucrose readings. iSAT reactions without the operon plasmid were performed to establish a background reading that was subtracted from experimental traces. Gradient fractions were collected and analyzed for rRNA content by gel electrophoresis in 1% agarose and imaged in a GelDoc Imager (Bio-Rad) (FIG. 15). Ribosome profile peaks were identified based on the rRNA content as representing 30S or 50S subunits, 70S ribosomes, or polysomes. To calculate the area under each curve, Riemann sums were taken with the 30S x-axis boundary ranging from 7 mL to 8.35 mL, the 50S x-axis boundary ranging from 8.5 to 9.5 mL, the 70S x-axis boundary ranging from 9.9 to 11.5 mL, and the polysomes x-axis boundary ranging from 11.725 to 13 mL. X-axis points were taken in 0.00625 mL intervals. Sums between each X-axis coordinate were taken, and totals were calculated for the given boundaries.

iSAT ribosome purification. Several (approximately 8) 15 µL iSAT reactions were prepared and incubated for 2 hours at 37° C., then pooled together. Purified 70S *E. coli* ribosomes were recovered as previously described (33), with pelleted iSAT ribosomes resuspended in iSAT buffer, aliquoted and flash-frozen.

Nucleotide distance calculations. Nucleotide distances were measured between the average center of each nucleotide to the average center of A76 of each respective tRNA and the attached amino acid residue of each the A-site and P-site tRNA molecules. Distances were calculated from the structure file of PDB ID: 4YBB, with tRNAs from PDB ID: 1VY4 (46) (Table 6 and Table 7).

Results

Examining mutational flexibility of PTC rRNA in vitro. The goal of this study was to use the iSAT platform to construct and characterize ribosomal active site mutants and generate a functional map of mutational flexibility. However, the ribosome's active site has evolved to accurately and efficiently process α-amino acid monomers using catalytic rRNA, that we would expect to exhibit high levels of conservation and would be less permissible, or flexible, to mutation. In fact, previous work has demonstrated in vivo that many nucleotide changes to highly-conserved nucleotides are detrimental (16), but the ribosome can still withstand some small changes at select positions (47) (Table 2). As a first step in characterizing the ribosome's active site, we quantitatively evaluated conservation at every nucleotide position within the PTC. Large subunit (LSU) sequences were taken from the Silva ribosomal-RNA database and aligned at PTC-nucleotide positions (43). Sequences were aligned for 1,614 species of bacteria and archaea (data not shown) and Shannon Entropy values were calculated (FIG. 3A). Shannon Entropy scores are akin to variance scores (though we caution that they ignore phylogenetic relatedness), with a Shannon Entropy of zero representing zero variance (100% conservation across the 1,614 species). Any values above zero indicate that evolutionary changes have occurred and result in multiple nucleotides within a given site in the alignment. As expected, the entire PTC active site (PTC-ring, A-loop, and P-loop) exhibited a high-level of conservation, with approximately 75% of the nucleotide positions possessing a Shannon Entropy value at or near zero.

Figure 7:
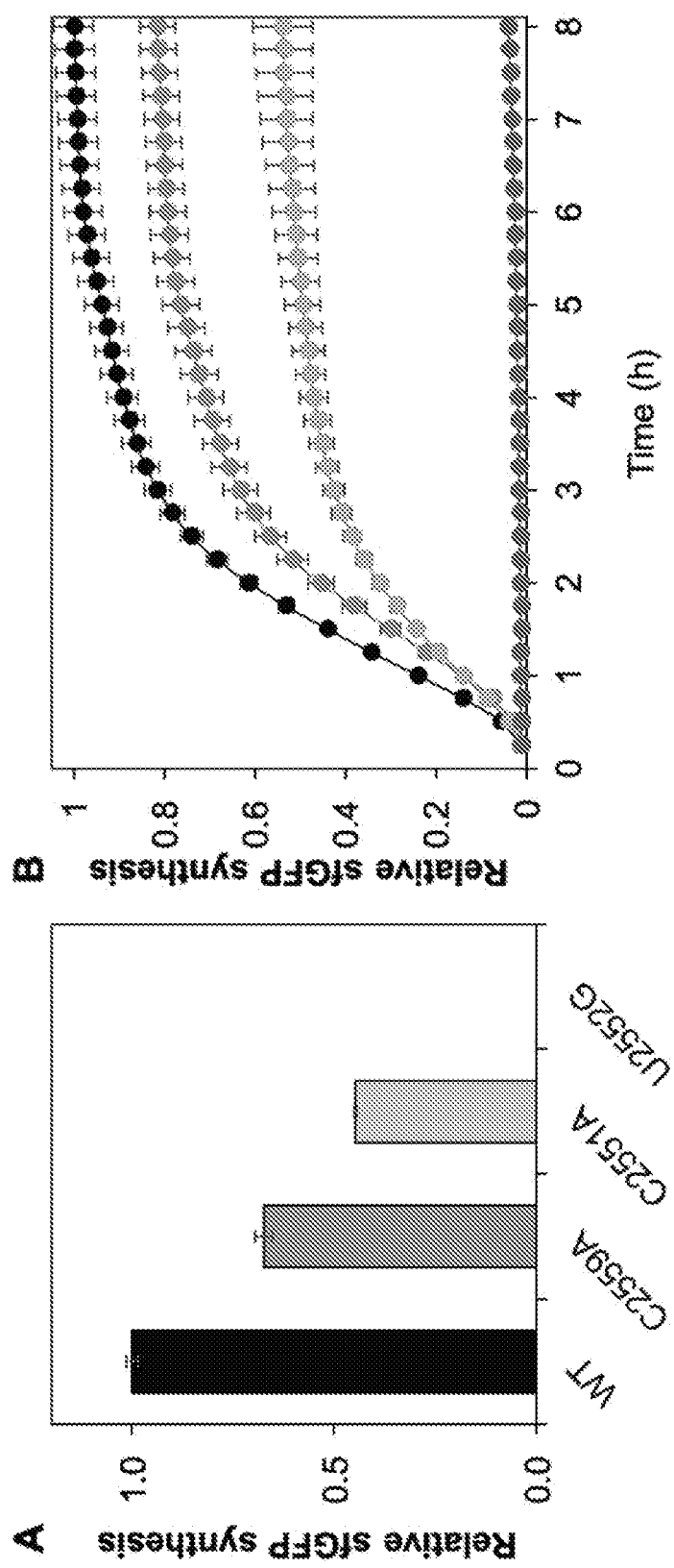
FIG. 7. Ribosomes with mutations in the A- and P-loops demonstrate decreased bulk protein synthesis rates. (A) Relative protein synthesis activity of A- and P-loop mutants tested in translation fidelity assays. (B) Protein synthesis kinetic time course curves from iSAT reactions for the following nucleotide mutations have been included in this graph: C2559A, C2551A, U2552G. Protein synthesis rates are proportional to relative protein synthesis titers. For simplicity and ease of visualization, not all nucleotide mutation kinetic curves are included on the graph. Values represent averages and error bars represent one standard deviation from the mean, with n≥3 for n number of independent reactions.

While the PTC active site exhibits high levels of nucleotide conservation, we can assess mutational flexibility at each rRNA nucleotide position by building rRNA mutants in the iSAT system. We constructed iSAT reactions, as previously described (32-35), possessing wild-type and all 180 mutant ribosomes, separately, and measured reporter protein biosynthesis yields via fluorescent activity over the course of 20 hours (FIGS. 3B and 3C). We used final protein biosynthesis yields as a proxy for overall activity because these yields mirror bulk protein synthesis rates in vitro (FIG. 3C, Table 1, FIG. 7, and Table 3). Relative activity was subsequently calculated to compare performance of each mutant by normalizing wild-type protein synthesis yields to one and mutant yields to the normalized wild-type yields. An overall mutational flexibility score was then determined for each nucleotide position by adding the relative activities of every possible point mutation. The highest mutational flexibility score of three indicates that all three nucleotide changes possess wild-type activity, while the lowest mutational flexibility score of zero indicates that all three nucleotide changes preclude any protein synthesis (Table 4).

Figure 3:
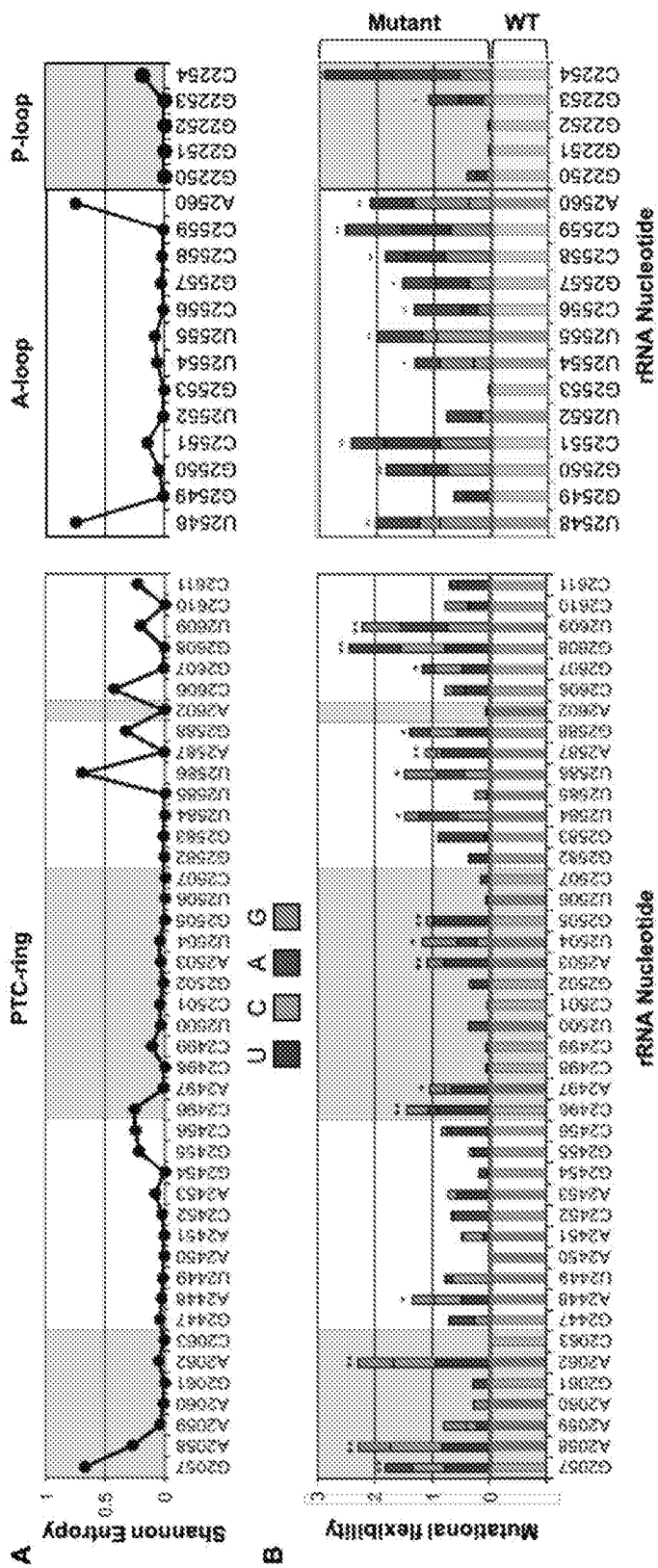
FIG. 3. The ribosome's peptidyl transferase center (PTC) is amenable to mutation, despite high sequence conservation. (A) Shannon entropy plot representing the conservation of PTC nucleotides across 1,614 of bacterial and archael species. All large subunit (LSU) sequences were taken from alignments found at the Silva database (43). Shannon entropy values of zero represent 100% conservation across all species. Despite the high conservation of the ribosome's PTC, there is high plasticity within its catalytic core. (B) Mutational flexibility of each PTC mutation relative to the activity of WT iSAT ribosomes. Nucleotides are color coded according to the legend. The original WT nucleotide activity is normalized to 1, and resides below the red line on the graph. Each possible nucleotide change at the corresponding position is color coded in the bars above the red line, with bar size representing relative activity. Single asterisks are placed above nucleotides wherein the sum of mutant activity (mutational flexibility) results in activity ≥1 (PTC-ring: G2057, A2058, A2062, A2448, C2496, A2497, A2503, U2504, G2505, U2584, U2586, A2587, G2588, G2607, G2608, and U2609; A- and P-loops: U2548, G2550, C2551, U2554, G2555, C2556, G2557, C2558, C2559, A2560, G2253, C2254). A second asterisk is placed above nucleotides wherein at least one nucleotide mutation results in activity ≥75% of WT activity (PTC-ring: G2057, A2058, A2062, C2496, A2503, G2505, A2587, G2608, and U2609; A- and P-loops: U2548, G2550, C2551, U2555, C2556, C2558, C2559, A2560, C2554). (C) Protein synthesis curves for representative nucleotide mutations have been included in this graph: wild type, high activity (A2062U and G0257U), medium activity (C2496G and A2451C), medium-low activity (U2585G and A2451U), and low activity (G2455A and C2452G) mutants were chosen. Translation rates for representative PTC mutants in this study are represented in Table 3. For simplicity and ease of visualization, only a subset of 180 nucleotide mutation kinetic curves are included on the graph.
Figure 3:
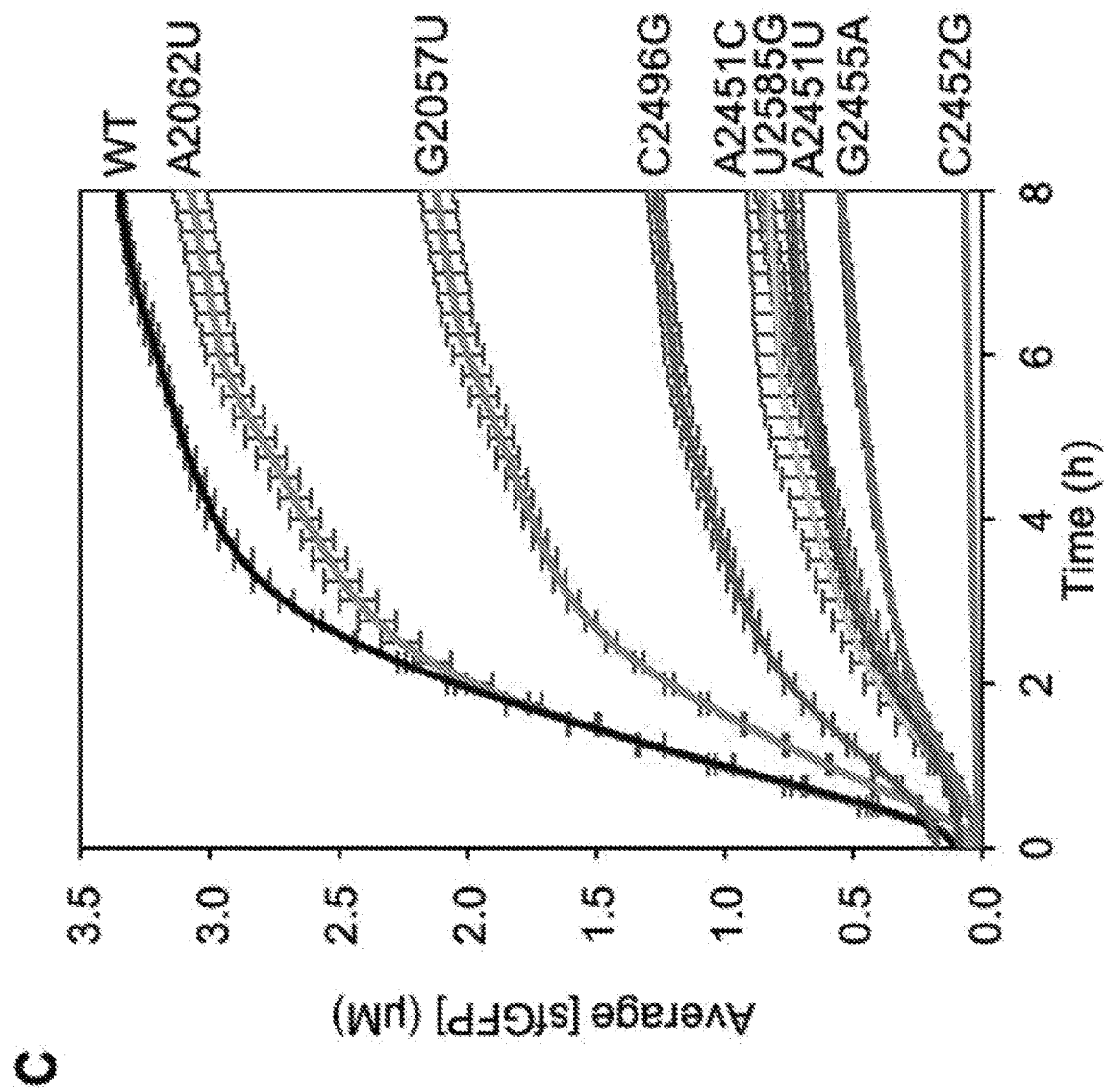

Despite the highly-conserved nature of the ribosome's active site, the majority (>85%) of the PTC-ring nucleotides possessed some degree of flexibility to mutational changes (one or more mutations at that position permitted full-length protein synthesis, determined by protein activity), as did 80% of A- and P-loop nucleotides (FIG. 3). Of the 43 PTC-ring nucleotides, 16 positions (G2057, A2058, A2062, A2448, C2496, A2497, A2503, U2504, G2505, U2584, U2586, A2587, G2588, G2607, G2608, and U2609) possessed a mutational flexibility score ≥1. And across the A- and P-loop nucleotides, 12 positions (U2548, G2550, C2551, U2554, U2555, C2556, G2557, C2558, C2559, A2560, G2253, C2254) resulted in a mutational flexibility score ≥1. Additionally, 9 PTC-ring nucleotides (G2057, A2058, A2062, C2496, A2503, G2505, A2587, G2608, and U2609) and 9 A- and P-loop nucleotides (U2548, G2550, C2551, U2555, C2556, C2558, C2559, A2560, C2554) possessed at least one nucleotide mutation that resulted in ≥75% of WT activity.

Figure 8:
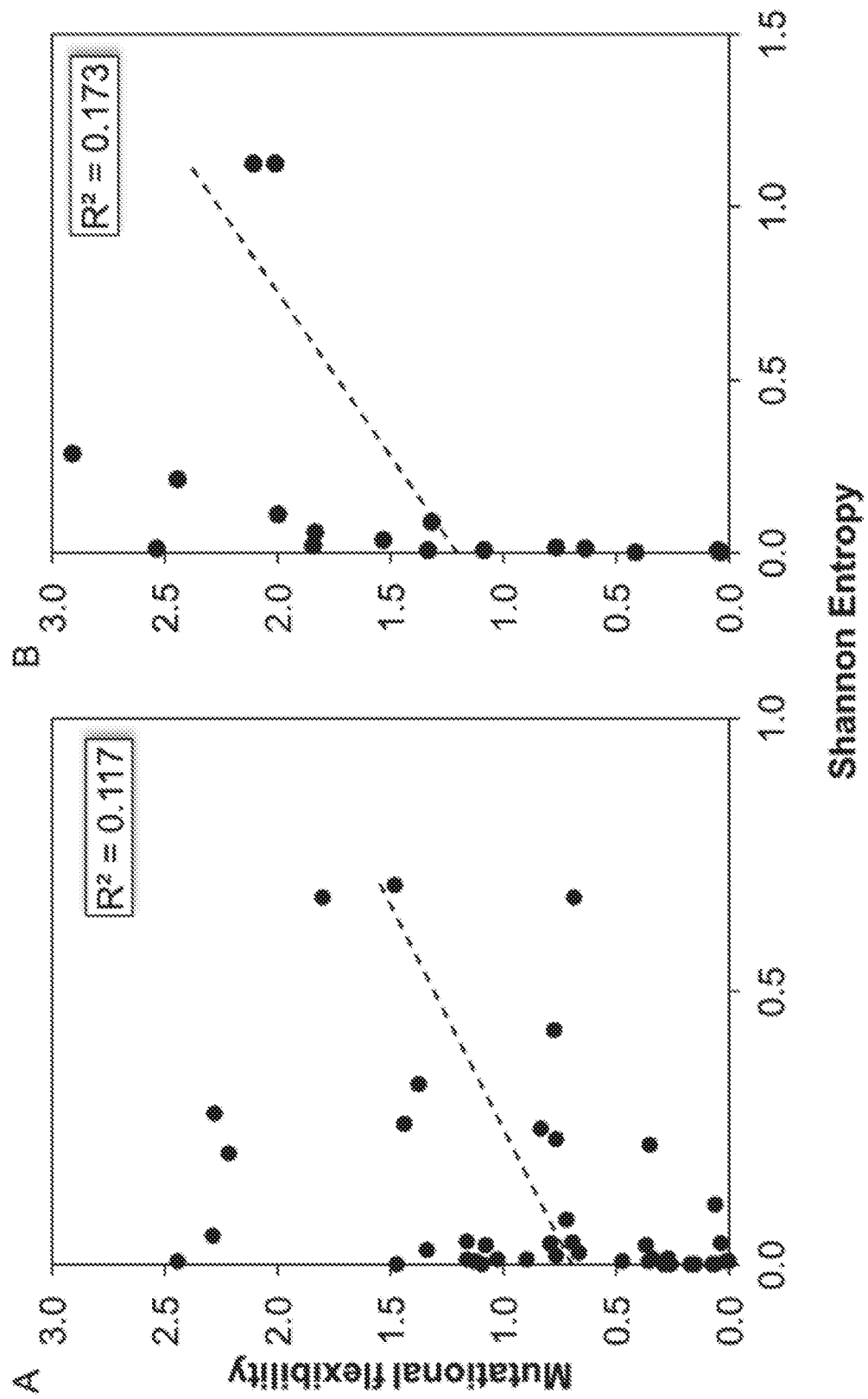
FIG. 8. Regression models of Shannon entropy (nucleotide conservation) against mutational flexibility (the sum of all nucleotide mutations' relative activity). (A) The regression plot for the PTC-ring possesses a low $R^2$ value ($R^2$=0.117, p=0.025) demonstrating difficulty in predicting mutational flexibility from nucleotide conservation. (B) The regression plot for the A- and P-loops also possesses a low $R^2$ value ($R^2$=0.173, p=0.086) demonstrating difficulty in predicting mutational flexibility from nucleotide conservation.

We then tested the degree to which our findings relate to natural sequence diversity of 23 S rRNA sequences by correlating mutational flexibility for individual sites with their Shannon Entropy values measured across the 1,614 species. For the PTC-ring, we found a significant (p=0.025) but weak ($R^2$=0.117) relationship, indicating that sequence diversity explains only a minor fraction of the observed variation in mutational flexibility (FIG. 8). For the A- and P-loops, we found a non-significant (p=0.086) and weak ($R^2$=0.173) relationship, indicating that the sequence diversity does not explain the observed variation in mutational flexibility. In total, these results illustrate a large degree of mutational flexibility that exists within the PTC and the difficulty in predicting mutational flexibility solely from nucleotide conservation.

Figure 4:
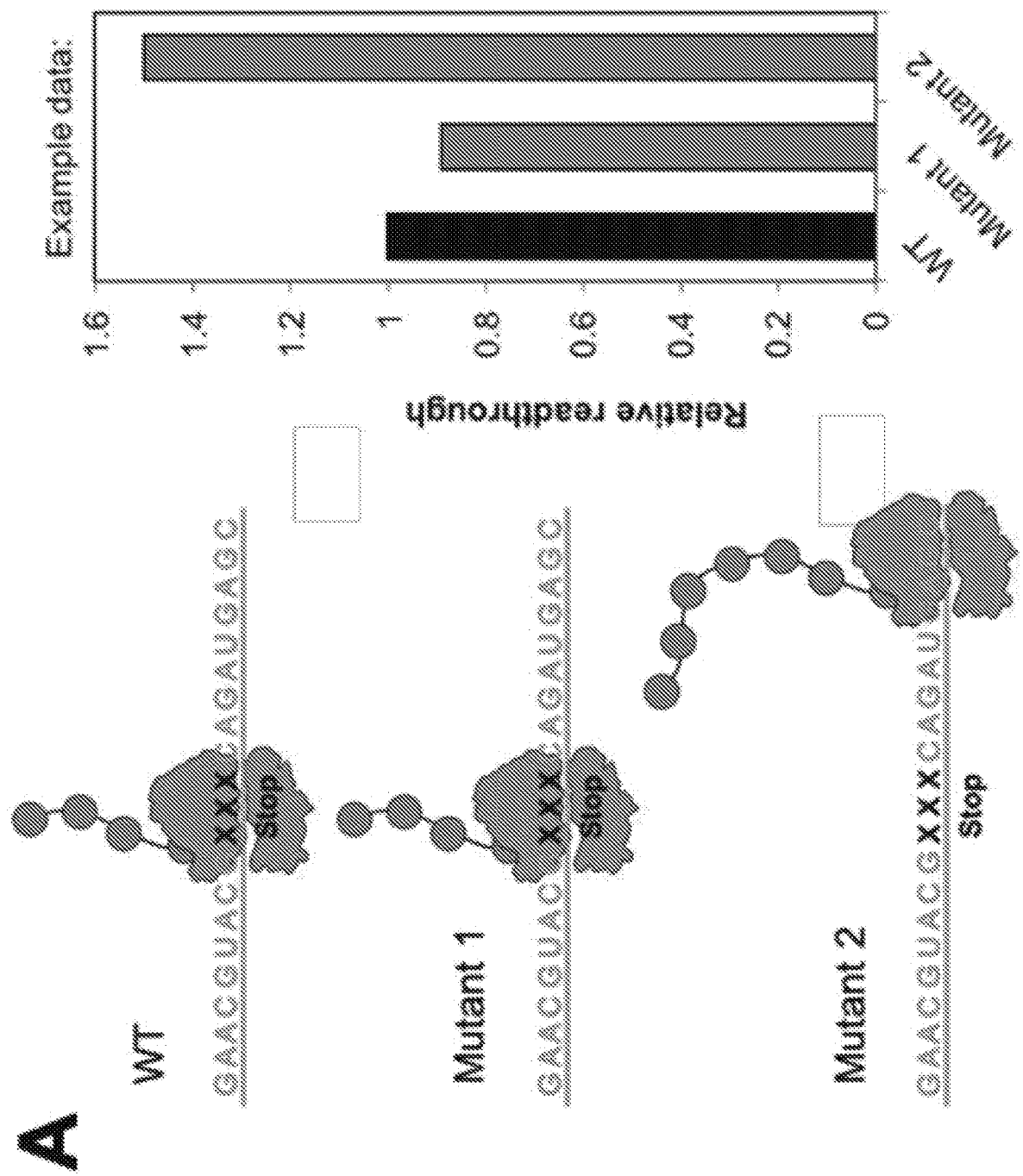
FIG. 4. Ribosomal PTC mutations increase stop-codon readthrough. (A) Schematic of translation fidelity assay using premature stop codon constructs. Assays were adapted from O'Connor et al. (37). Premature stop codon readthrough from wild type ribosomes was normalized to 1. Mutant ribosome premature stop codon readthrough was quantified through fluorescence and set relative to WT. Mutants with lower fidelity (higher readthrough of premature stop codons) produce higher relative sfGFP titers. (B) UAG stop codon readthrough at amino acid position 50, 100, 116, and 216. (C) UAG, UGA, and UAA stop codon readthrough at amino acid position 100. Relative activity in translation fidelity assays using premature stop codons was assessed using sfGFP fluorescence. The pJL1-sfGFP plasmid possessing a UAG stop codon at the specified locations were introduced into iSAT reactions as the reporter plasmid along with the mutant or wild-type rRNA plasmids. Values represent averages and error bars represent one standard deviation from the mean, with n≥3 for n number of independent reactions.
Figure 4:
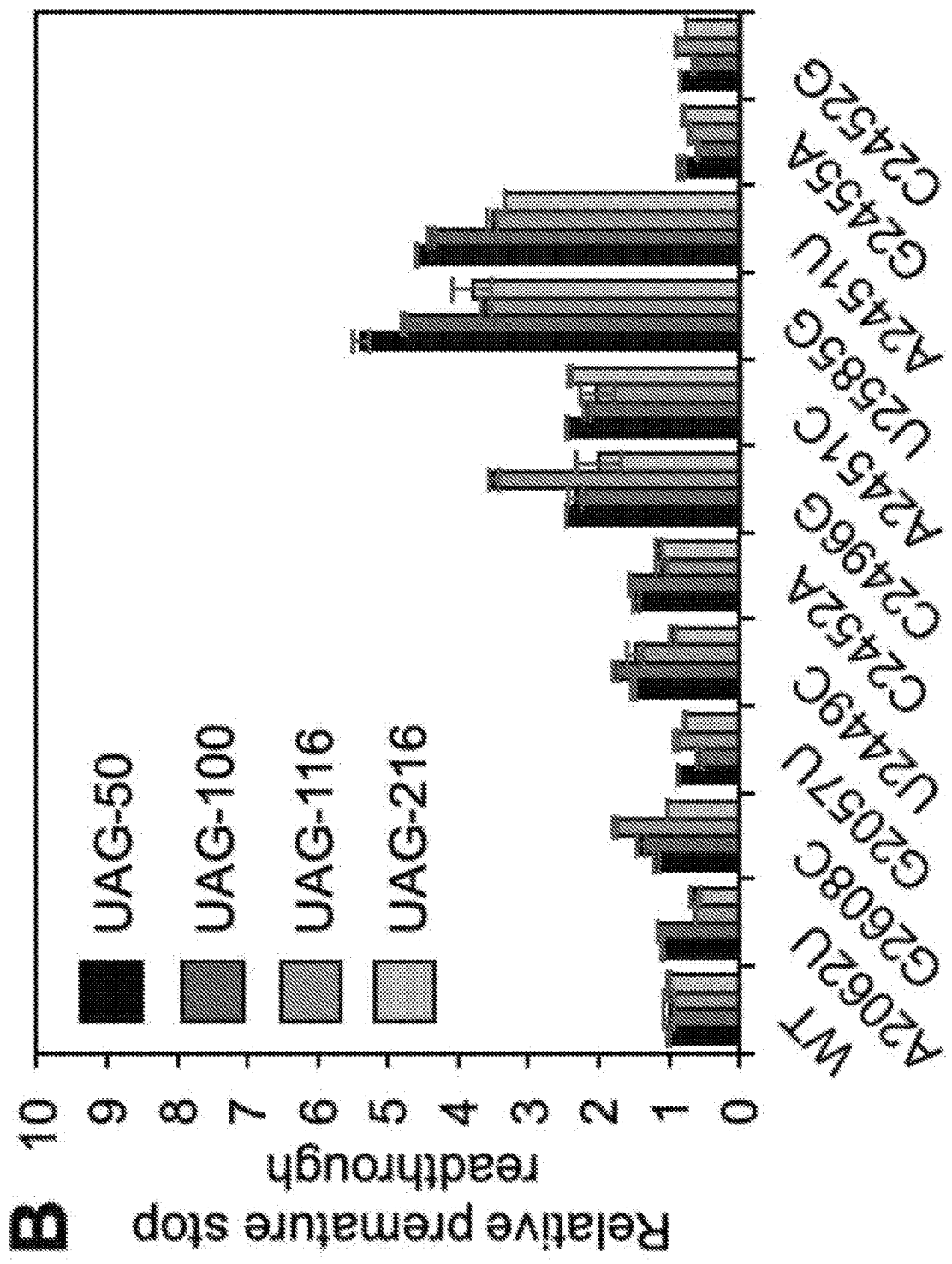
Figure 4:
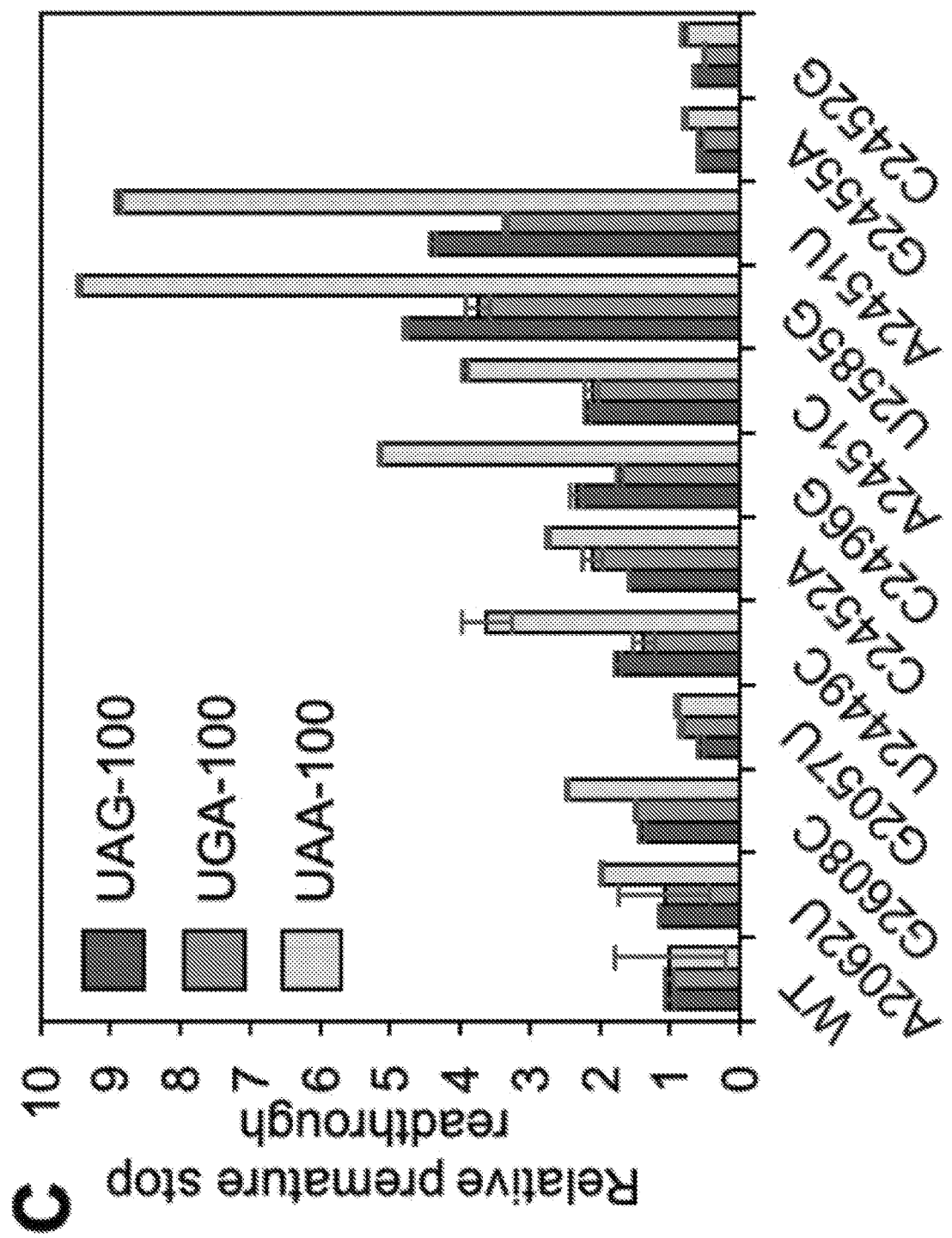
Figure 9:
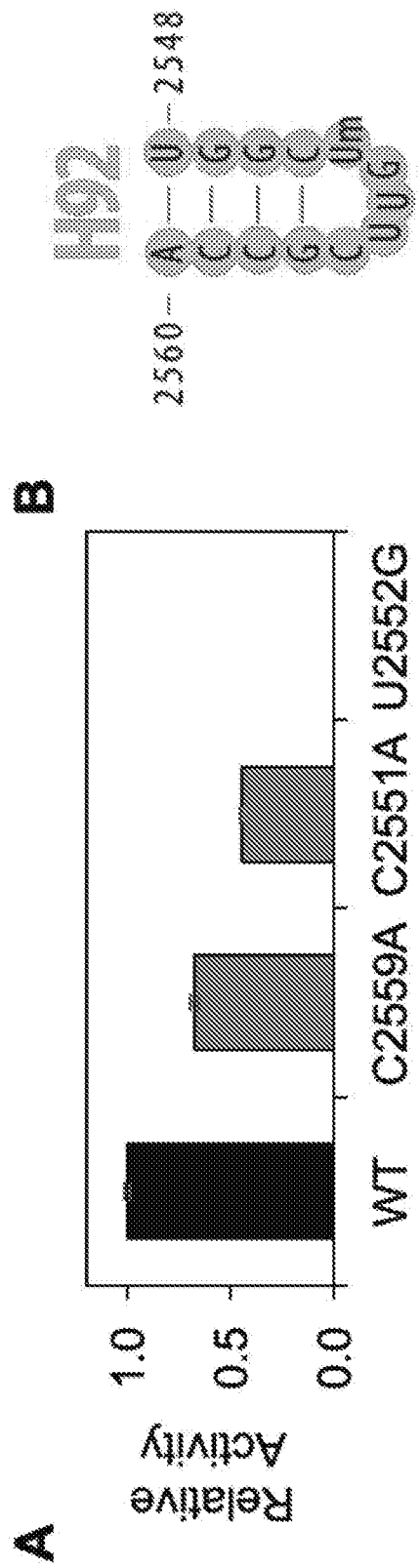
FIG. 9. Ribosomal A-loop mutations do not increase stop-codon readthrough. (A) Relative protein synthesis activity of A-loop mutants tested in translation fidelity assays. (B) A-loop secondary structure. (C) UAG stop codon readthrough at amino acid position 50, 100, 116, and 216 of sfGFP. (D) UAG, UGA, and UAA stop codon readthrough at amino acid position 100 of sfGFP. As described in the main text, the relative readthrough activity in translation fidelity assays using premature stop codons was assessed using sfGFP fluorescence. sfGFP levels obtained with wild-type rRNA plasmids are normalized to 1, and values obtained with each of the mutants were expressed relative to that obtained with the respective wild-type rRNA plasmid. To enable comparison with FIG. 4 from the main text, the y-axis values are extended to 10 in C and D. Values represent averages and error bars represent one standard deviation from the mean, with n≥3 for n number of independent reactions.
Figure 9:
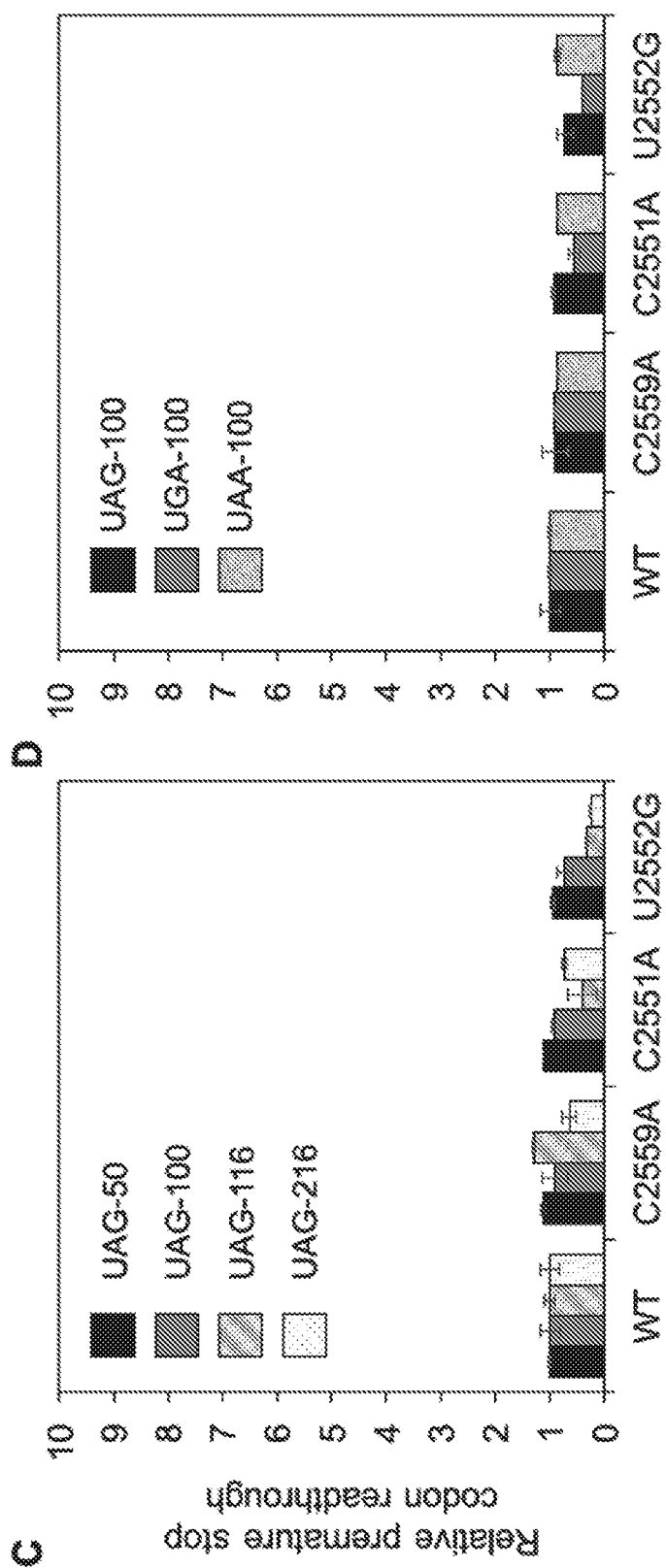
Figure 10:
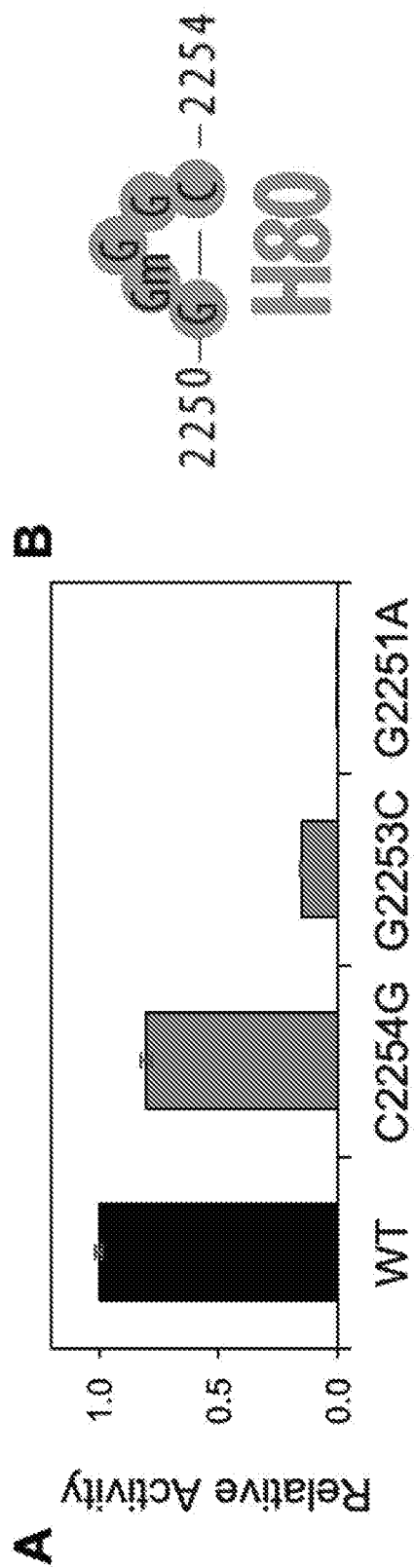
FIG. 10. Ribosomal P-loop mutations do not increase stop-codon readthrough. (A) Relative protein synthesis activity of P-loop mutants tested for fidelity. (B) P-loop secondary structure. (C) UAG stop codon readthrough at amino acid position 50, 100, 116, and 216 of sfGFP. (D) UAG, UGA, and UAA stop codon readthrough at amino acid position 100 of sfGFP. As described in the main text, the relative readthrough activity in translation fidelity assays using premature stop codons was assessed using sfGFP fluorescence. sfGFP levels obtained with wild-type rRNA plasmids are normalized to 1, and values obtained with each of the mutants were expressed relative to that obtained with the respective wild-type rRNA plasmid. To enable comparison with FIG. 4 from the main text, the y-axis values are extended to 10 in C and D. Values represent averages and error bars represent one standard deviation from the mean, with n≥3 for n number of independent reactions.
Figure 10:
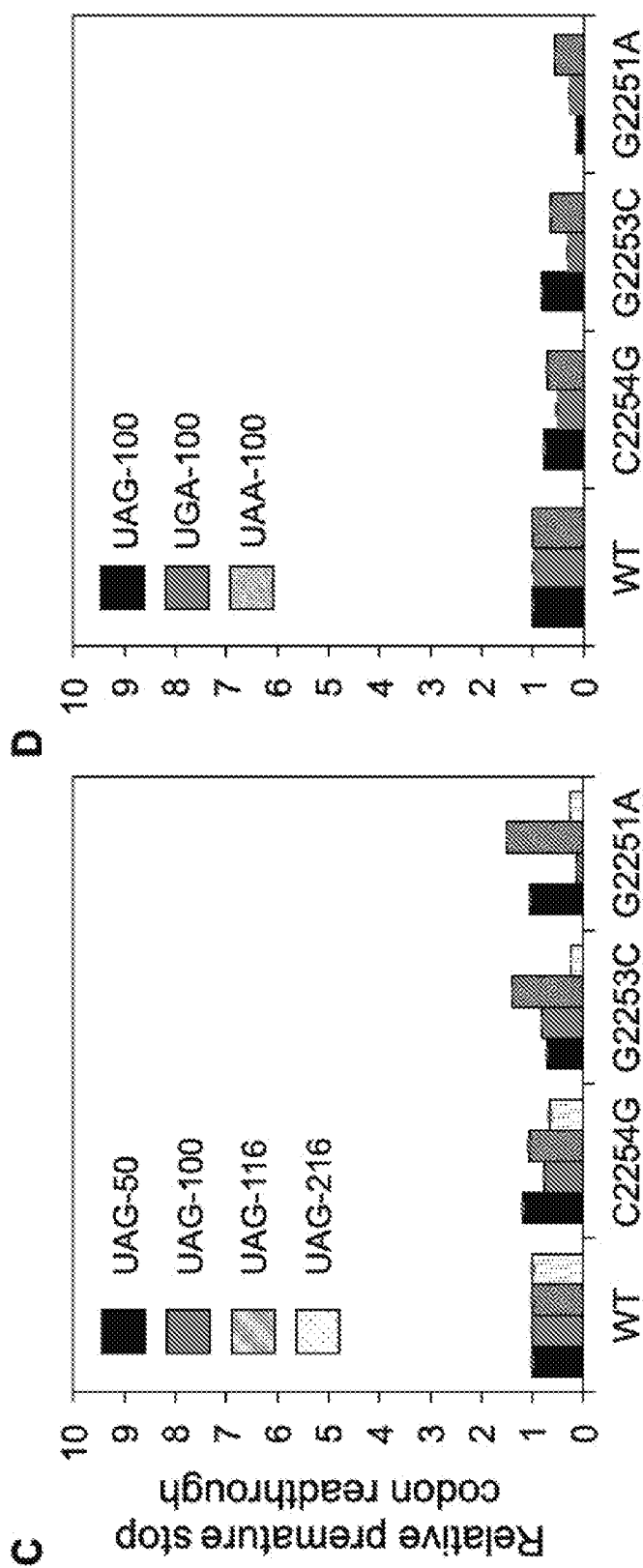

Characterizing PTC mutant ribosome translation readthrough. With the PTC exhibiting a high degree of mutational flexibility, we wondered if mutants of highly-conserved nucleotides that possessed observable translational activity were accurately translating protein. Previously, mutations in the active site of the E. coli ribosome were reported to have a negative impact on translation readthrough and fidelity (14,42,48), suggesting that our mutant ribosomes might have the same issues. To assess whether our rRNA mutants' functionality was being impacted by impaired translation readthrough and accuracy, we carried out a series of experiments involving premature stop codon readthrough adapted from previously-reported assays (14) (FIG. 4A). Specifically, the readthrough assay measures fluorescence output of iSAT reactions using sfGFP reporter constructs separately possessing UAG premature stop codons at amino acid positions 50, 100, 116, and 216 of sfGFP, and comparing three different stop codons (UAG, UGA, and UAA) all positioned at amino acid 100 of sfGFP. Readthrough efficiencies were determined by comparing relative, active sfGFP produced from iSAT reactions using each rRNA mutant construct to wild-type ribosome constructs for each reporter. We tested whether ribosomes with mutations possessing high, medium, and low activity (PTC-ring: A2062U, G2608C, G2057U, U2559C, C2452A, C2496G, A2451C, U2585G, A2451U, G2455A, C2452G; A-loop: C2559A, C2551A, U2552G; and P-loop: C2254G, G2253C, G2251A) could readthrough engineered stop codons in sfGFP mRNA (FIG. 4, FIG. 9, and FIG. 10). PTC-ring mutations C2496G, A2451C, U2585G, and A2451U exhibited a high-degree of stop codon readthrough (FIG. 4B-C), while the A- and P-loop mutations we probed maintained similar minimal readthrough to wild-type (FIG. 9, and FIG. 10). Our results corroborate previous studies (14) that have shown impaired readthrough of A2451C and A2451U mutants and identify C2496G and U2585G as mutants with similar impairment. While these are insightful findings, our assays alone are not capable of discriminating between translation fidelity and termination but rather characterize them together. Furthermore, efforts to identify the molecular mechanism by which mutations in the large subunit incur miscoding are not well-understood. Although the small subunit is largely recognized as the site of decoding, previous studies have identified decoding changes upon mutating the large subunit (40,42,48,49). It is hypothesized that the arrangement and geometry of the tRNAs in elongating ribosomes is perturbed by these active site mutations, thus decreasing the rate of peptidyl transfer and promoting errors in mRNA decoding (3,4,42,48,50). Although we cannot conclude a precise molecular mechanism, our results indicate that readthrough and decoding are indeed impacted by several mutations to the ribosome's PTC active site, adding to the growing number of nucleotides that play a key role in monomer positioning.

Figure 5:
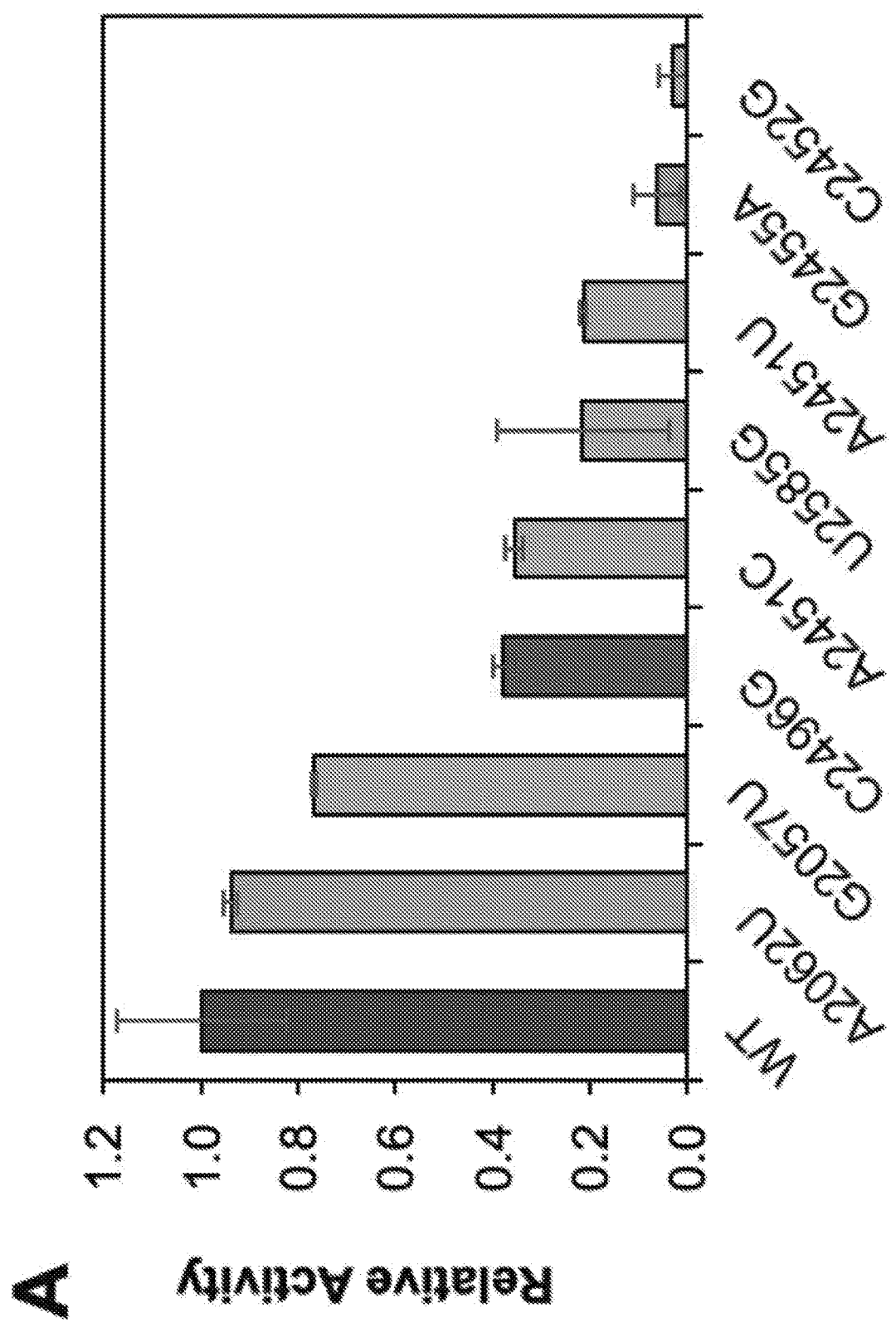
FIG. 5. Sucrose gradient fractionation identifies assembly problem with ribosomal PTC mutant G2455A. (A) The eight nucleotide mutations chosen for sucrose gradient fractionation based on their activity. Two high activity (A2062U and G2057U) mutants were chosen, two medium activity (A2451C and G2505A), and two low activity mutants (G2455A and C2452G) were assessed for assembly and compared to WT. (B) A wild type sucrose gradient fractionation trace (blue) is compared to 3 representative mutant traces (color coded based on nucleotide mutation activity graph). From bottom to top, the mutants are positioned in decreasing activity order. The bar graphs to the right indicate the fraction of 30S subunits, 50S subunits, 70S ribosomes, or polysome particles relative to the total species present. (C) Relative areas under sucrose gradient fractionation trace curves were used to calculate ratios of subunits to 70S and polysome particles as well as the ratio of 70S ribosomes to polysomes.
Figure 5:
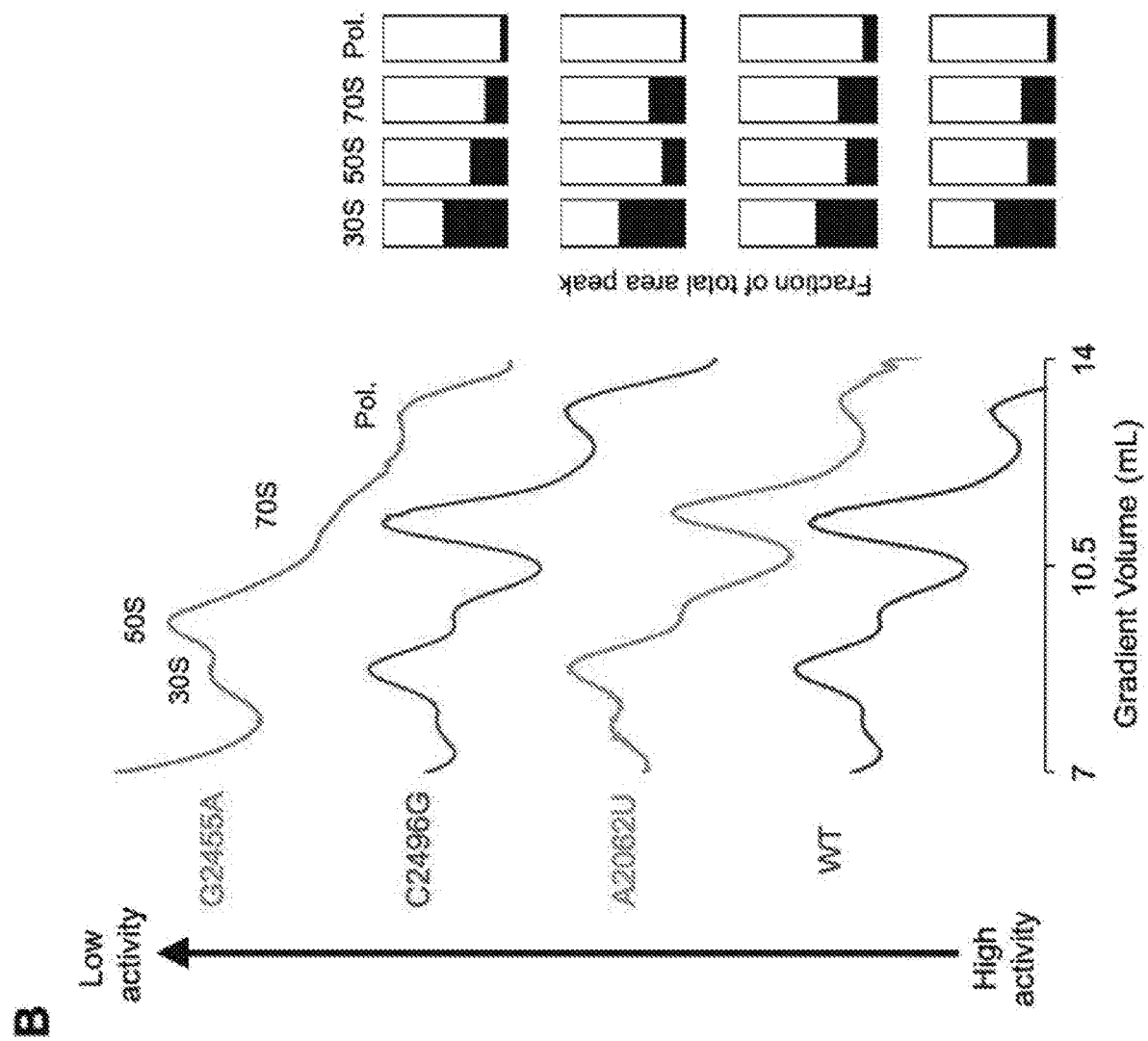
Figure 11:
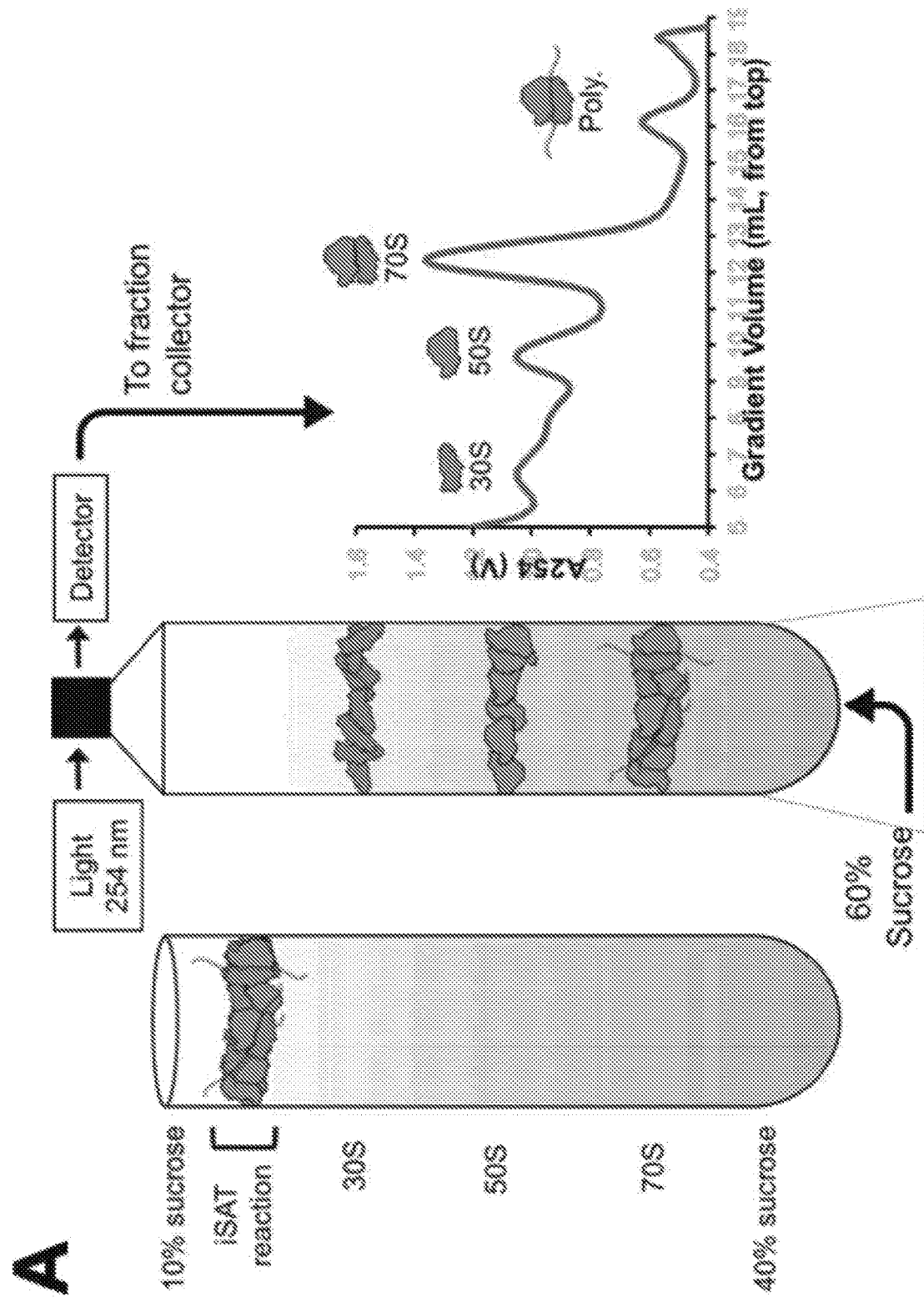
FIG. 11. Characterizing ribosomal assembly in vitro. (A) Schematic of the sucrose gradient fractionation experiment. (B) Representative nucleotide mutations were chosen for sucrose gradient fractionation based on their activity. Two high activity (A2062U and G2057U) mutants were chosen, three medium activity (C 2496G, A2451C, and U2585G), and three low activity mutants (A2451U, G2455A, and C2452G) were assessed for assembly and compared to WT. Additionally, two representative A- and P-loop nucleotides were also analyzed for assembly. (C) Comparison of PTC-ring sucrose gradient fractionation traces. Wild type sucrose gradient fractionation traces (black) are overlaid on top of mutant traces (color coded based on nucleotide mutation activity graph). (D) Comparison of representative A- and P-loop mutants' sucrose gradient fractionations.
Figure 11:
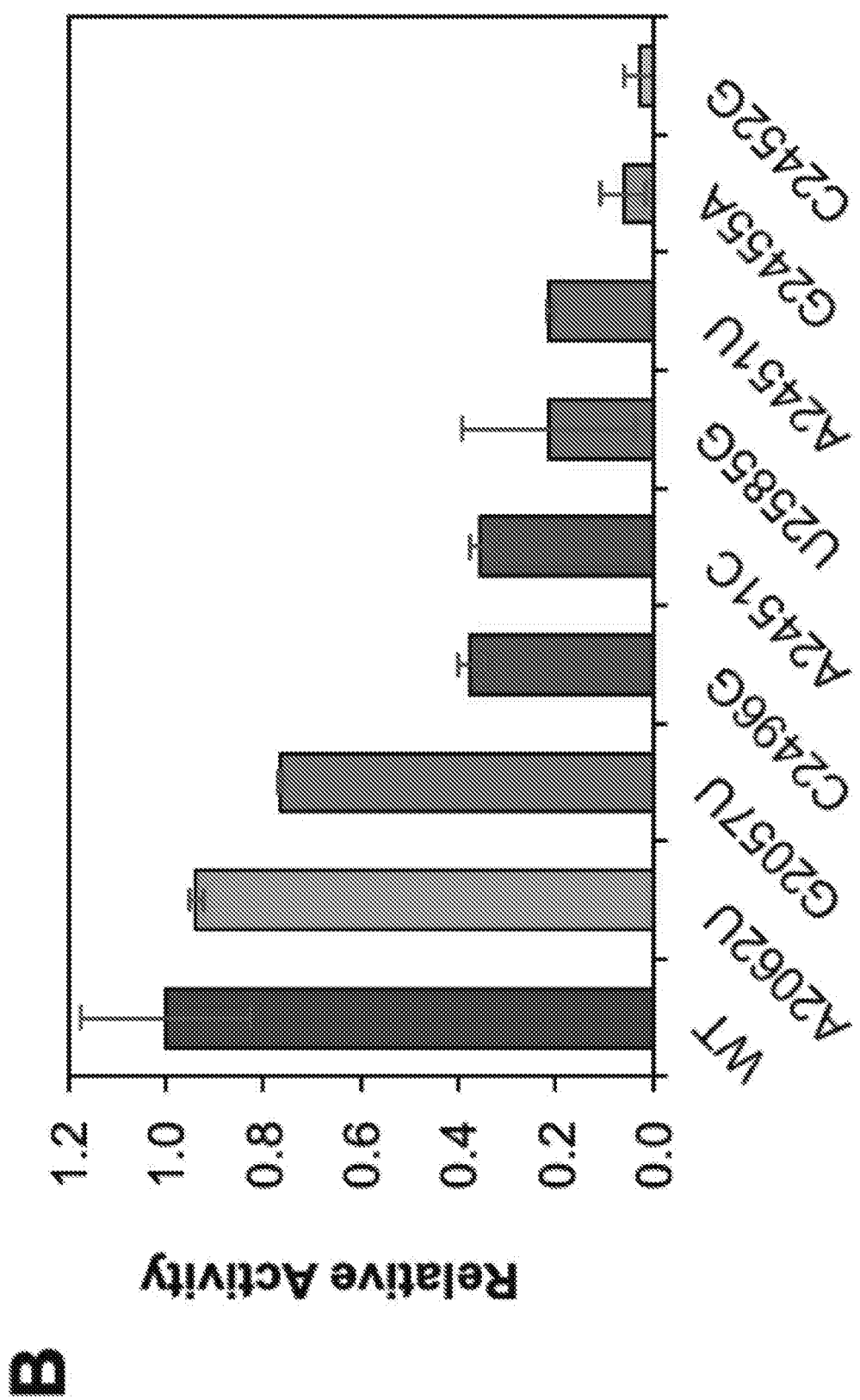
Figure 11:
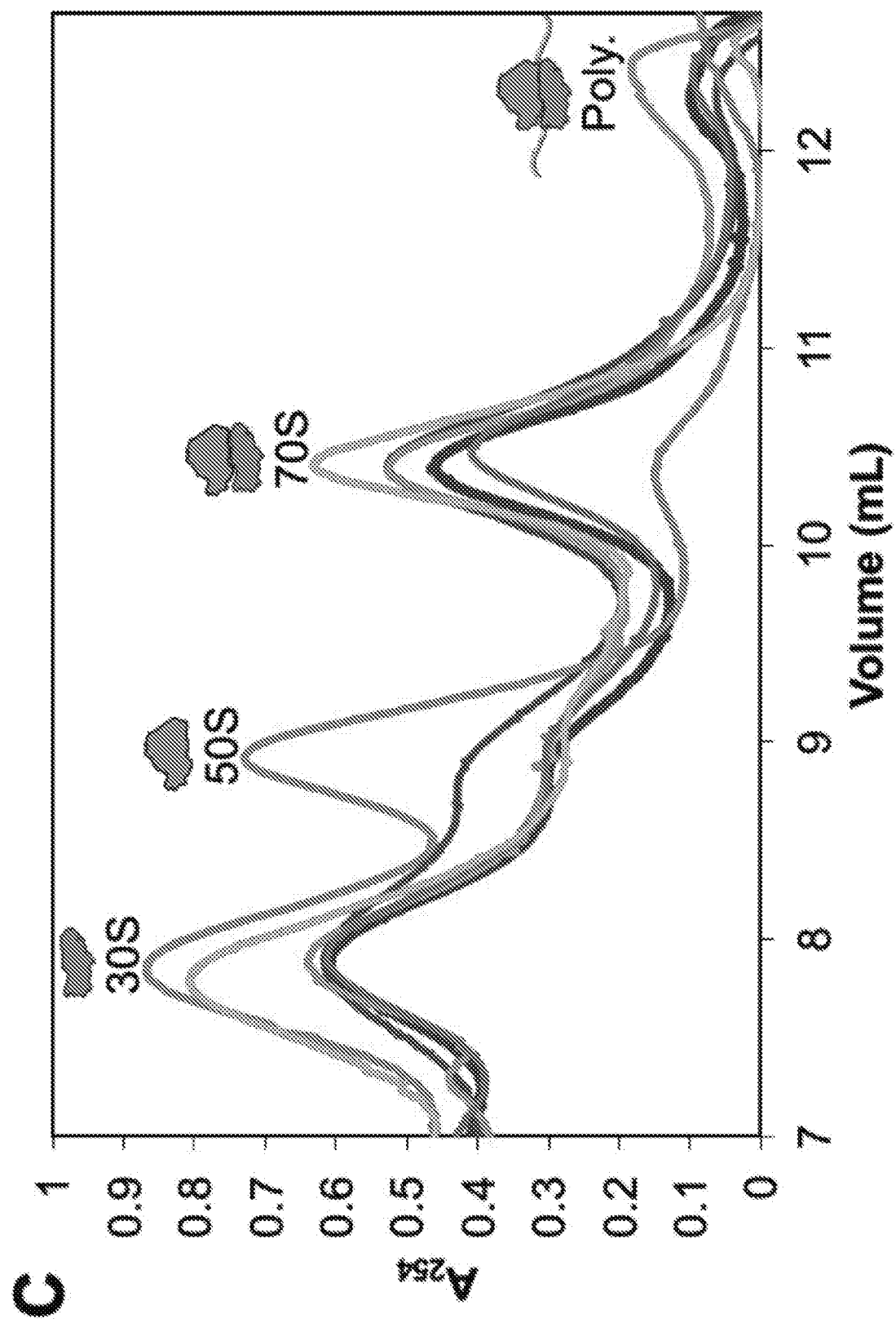
Figure 11:
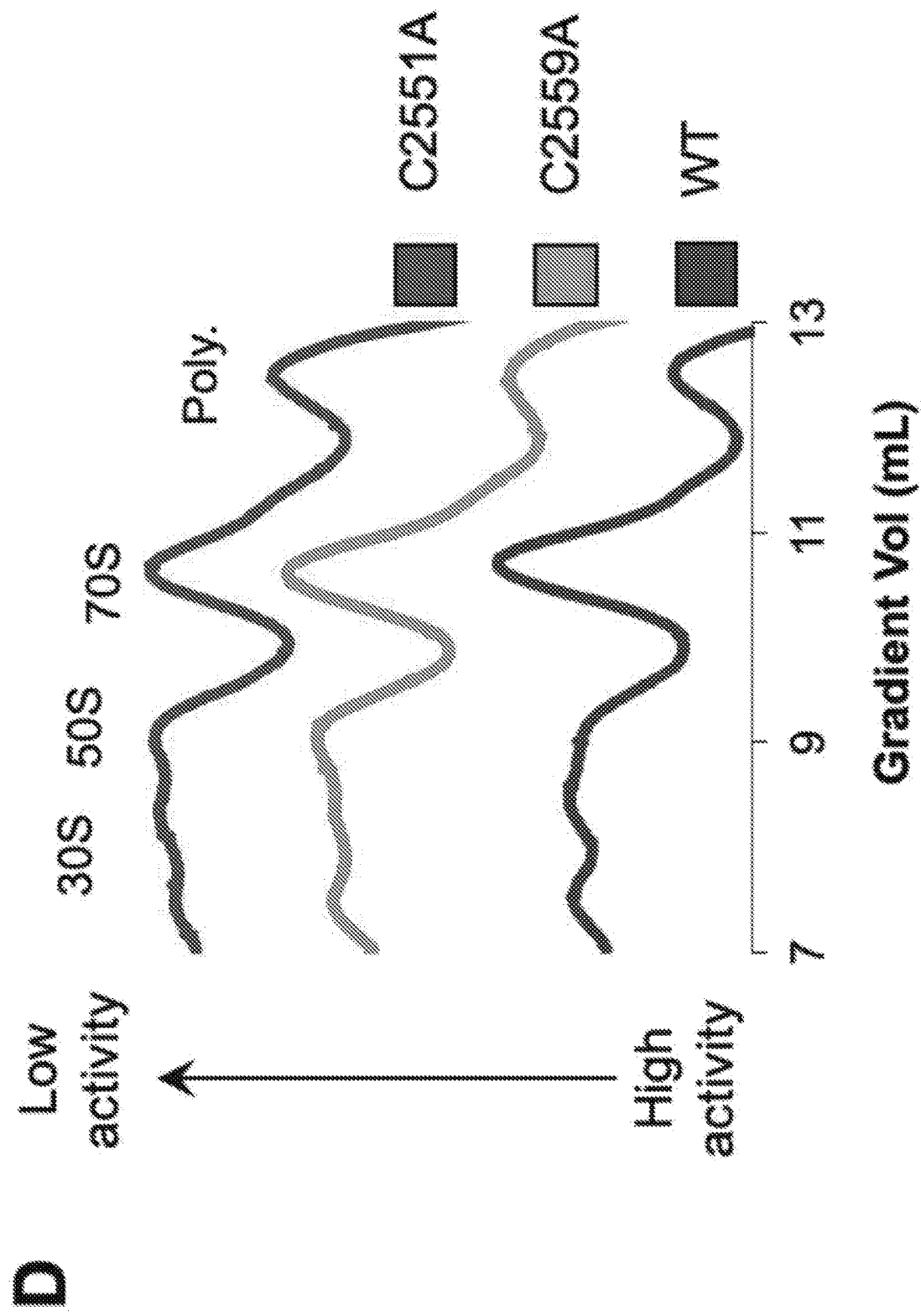

Incorporation of ribosomes with PTC active site mutations into functional polysomes. For all the PTC mutants, but especially those with low activity, we wondered if activity was related to the mutants' ability to assemble into functional 70S ribosomes and translate in polysomes. This is because iSAT combines ribosome assembly and translation in a single-pot reaction. It is possible that an rRNA mutation may impact assembly (as opposed to molecular function), resulting in reduced translation activity. To this point, we analyzed assembly of mutant ribosomes by observing the 30S subunit, 50S subunit, 70S particles, and polysomes using sucrose gradient fractionation as previously described (32) (FIG. 5 and FIG. 11). Using a sucrose gradient, iSAT reactions were centrifuged, fractionated, and trace peaks analyzed (Table 5). A set of high-, medium-, and low-activity mutants were chosen for analysis, with a few mutants also possessing compromised translation fidelity (C2496G, U2585G, and A2451U). In the PTC-ring, all mutants except for G2455A broadly possessed similar assembly profile traces to wild-type iSAT ribosomes (FIG. 5B), with approximately 44-50% 30S subunits, 20-23% 50S subunits, 24-28% 70S particles, and a decreasing percentage of polysomes (approximately matching decreasing activity) (Table 5). G2455A, exhibited a very different profile, accumulating more free subunits and a decreased amount of polysomes and 70S ribosomes (~50% 30S subunits, 29% 50S subunits, 16% 70S particles and 4% polysomes). After assessing assembly of mutants in the A- and P-loops, we found that the two mutations probed (C2559A and C2551A) both possessed assembly profiles similar to wild type (FIG. 11) (Table 5).

Notably, upon analyzing the relative abundance of species, we observed that compared to wild type—which has a relative ratio of subunits to 70S+polysomes value of ~2—G2455A has a relative ratio of approximately 4 (FIG. 5C). When comparing the relative ratio of 70S to polysomes, wild-type and mutants with highest activity (A2062U and G2057U) have similar ratios (70S:polysomes values of 3 to 5). As activity decreases, this ratio tends to increase roughly proportionately, suggesting that fewer 70S ribosomes are accumulating as polysomes. The mutant with the lowest activity, C2452G, has the largest 70S to polysome ratio, with a value of 28.

Figure 6:
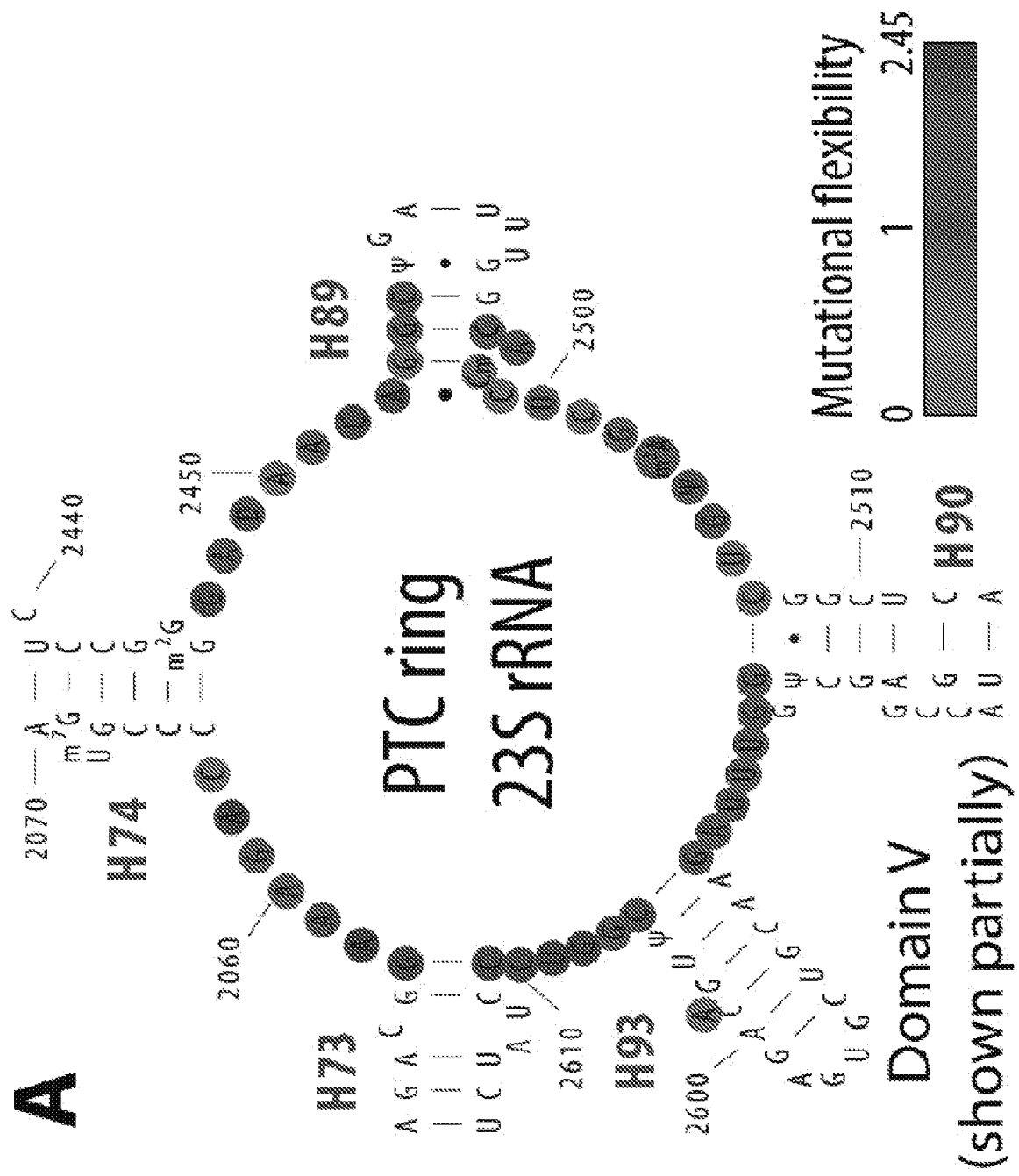
FIG. 6. A mutational map reveals that the ribosome's PTC is composed of functional pockets and shells. (A) Secondary structure and (B) crystal structure model of the PTC-ring nucleotides probed in this study (heat mapped), along with the A-site tRNA, and P-site tRNA. (C) Crystal structure and secondary structure models of the A- and P-loop nucleotides probed in this study (heat mapped), A-site tRNA (green), P-site tRNA (blue), and PTC ring nucleotides (grey). (D-J) Crystal structure model of the PTC-ring nucleotides possessing: (D) the lowest mutational flexibility (red and magenta), (E) medium/low mutational flexibility (red-violet), (F) medium/high mutational flexibility (violet), and (G) the highest mutational flexibility (violet-blue). (H) Crystal structure model of the A-loop nucleotides probed in this study (heat mapped), A-site tRNA (green). (I) Crystal structure model of the P-loop nucleotides probed in this study (heat mapped), P-site tRNA (blue). (J) Structure model highlighting the nucleotides with mutants possessing increased translation readthrough (C2496, U2585, and A2451), as well as assembly defects (G2455).
Figure 6:
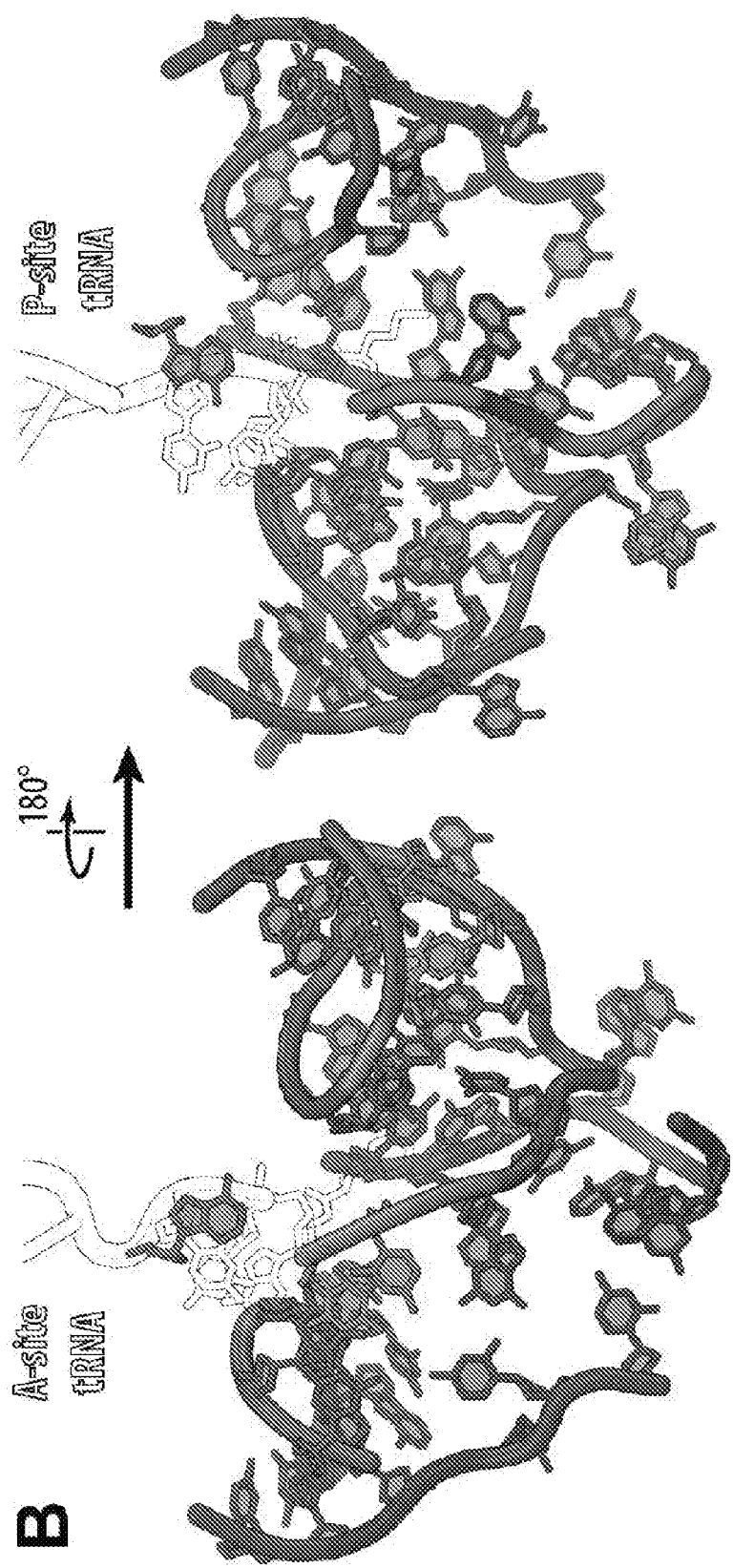
Figure 6:
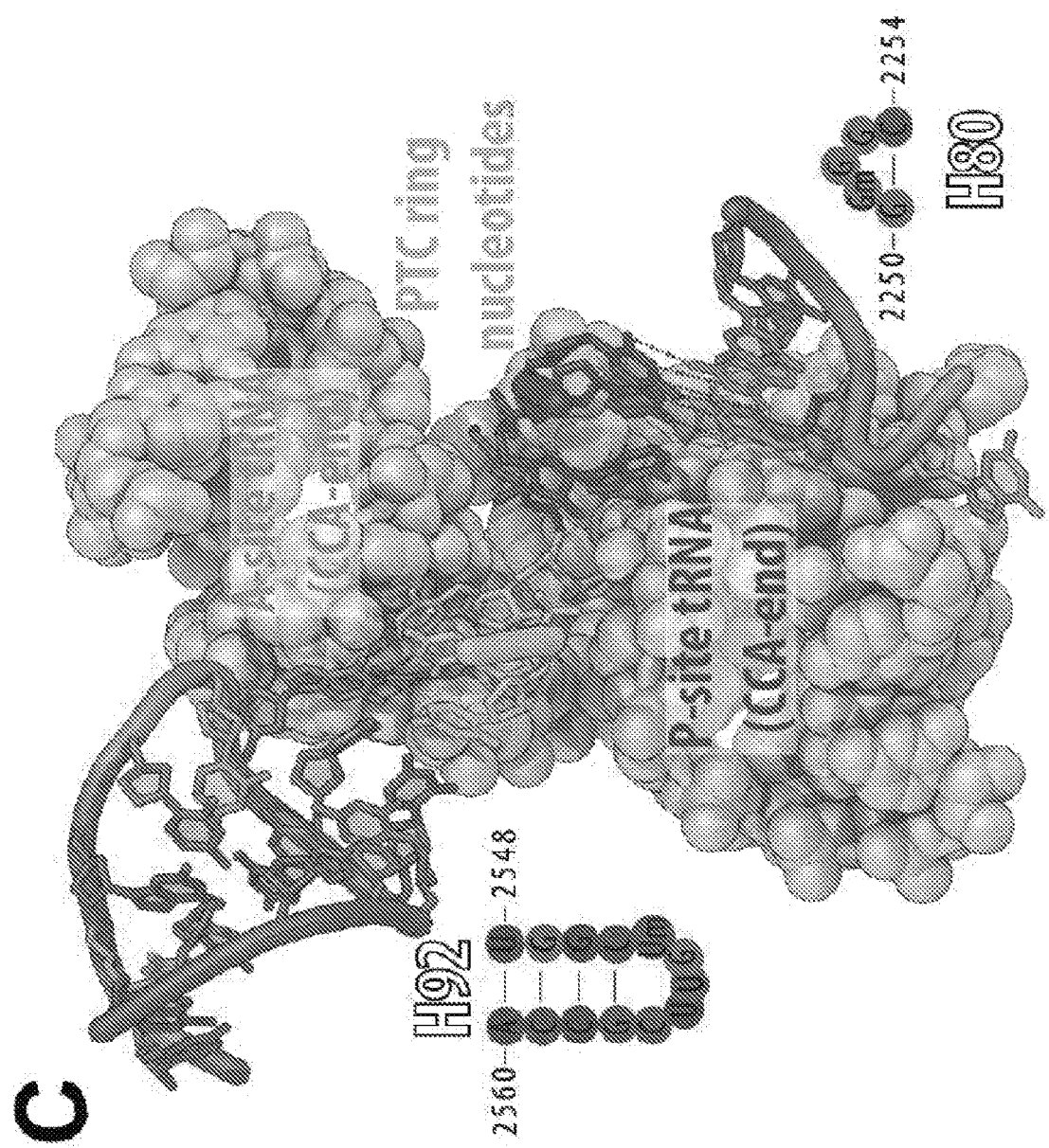
Figure 6:
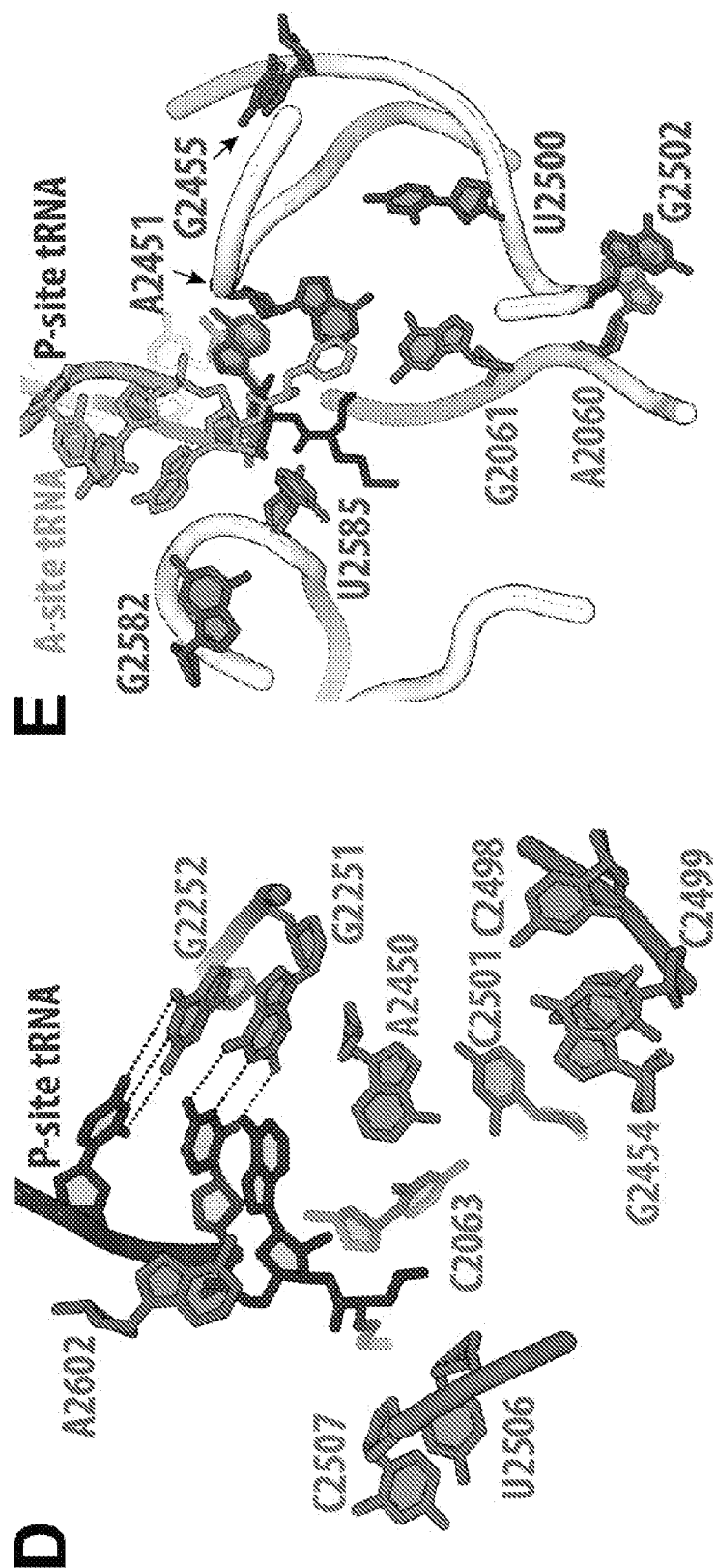
Figure 6:
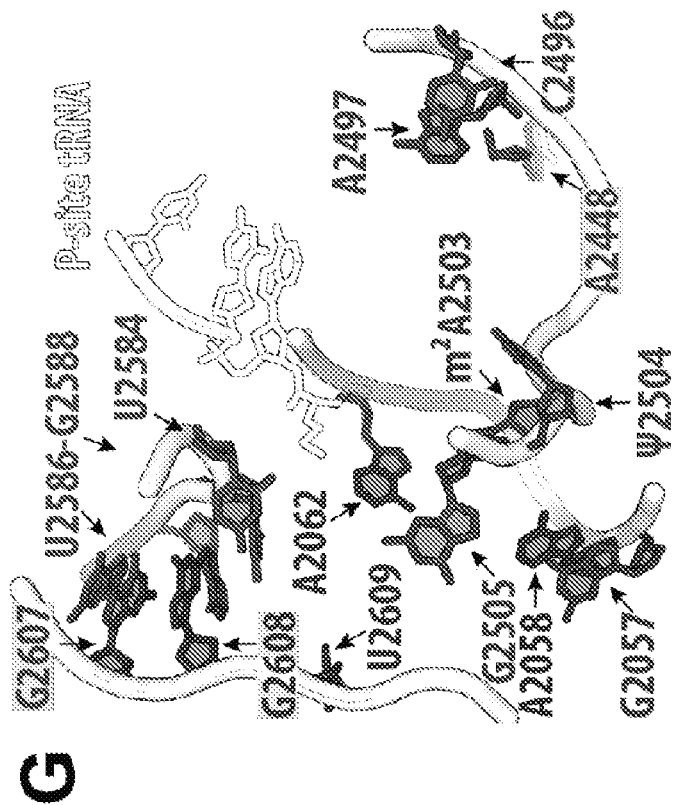
Figure 6:
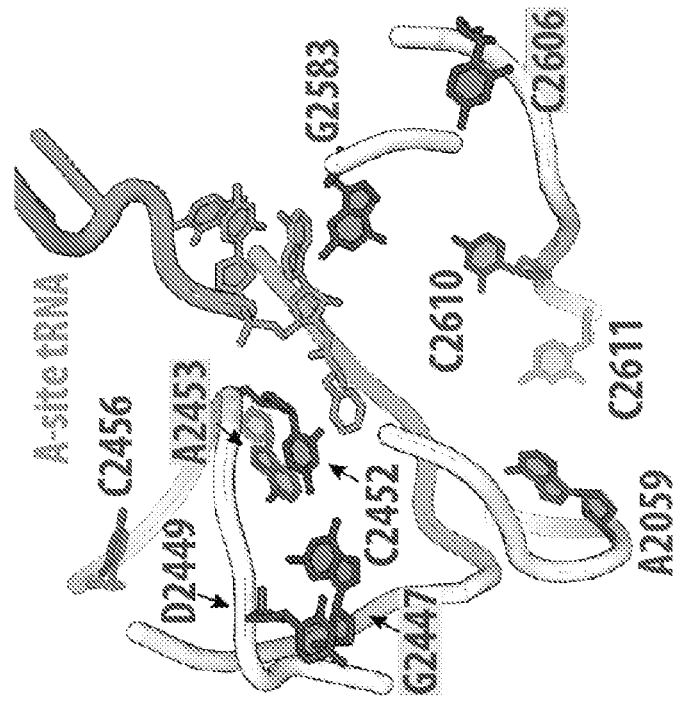
Figure 6:
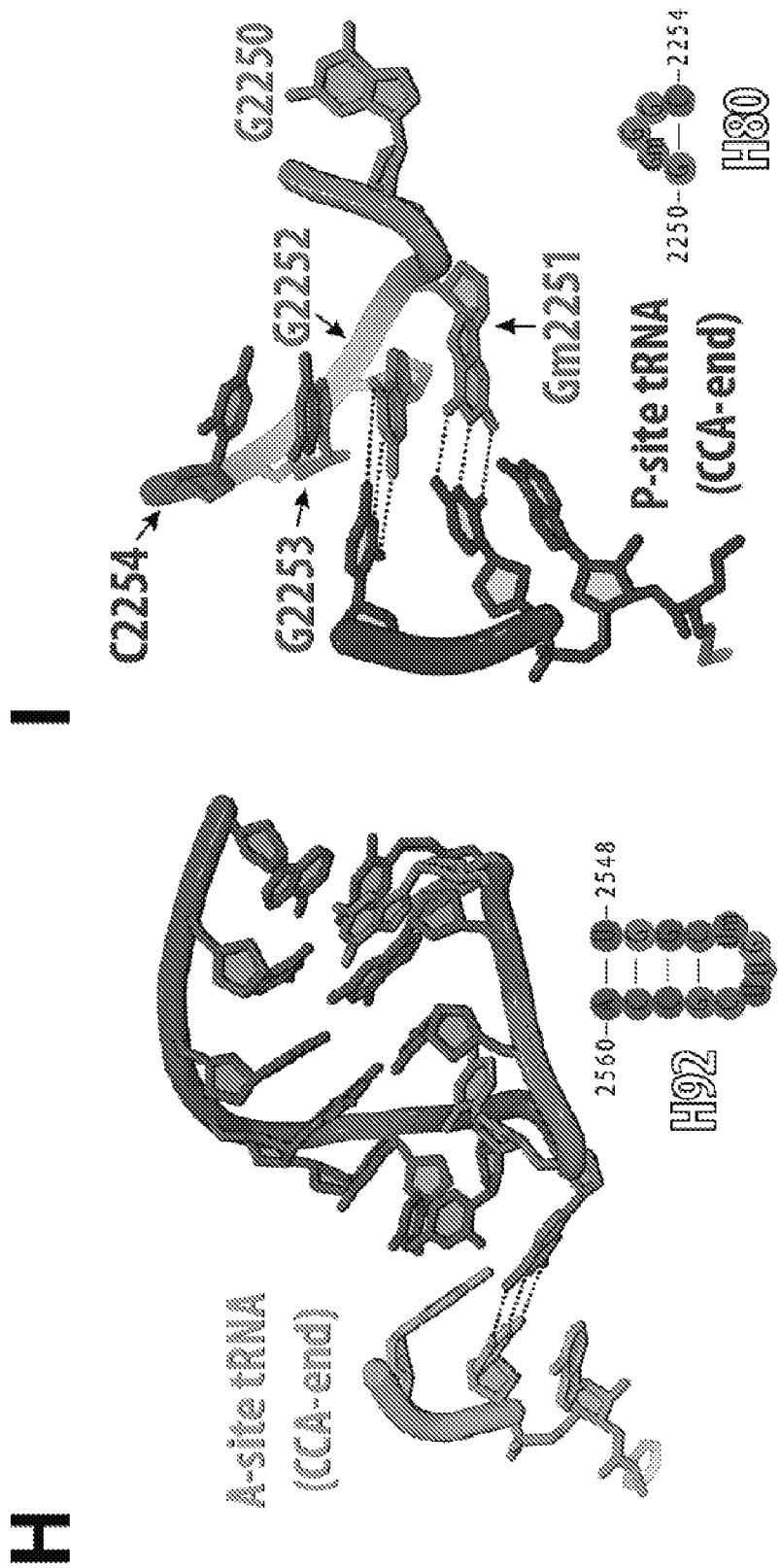
Figure 6:
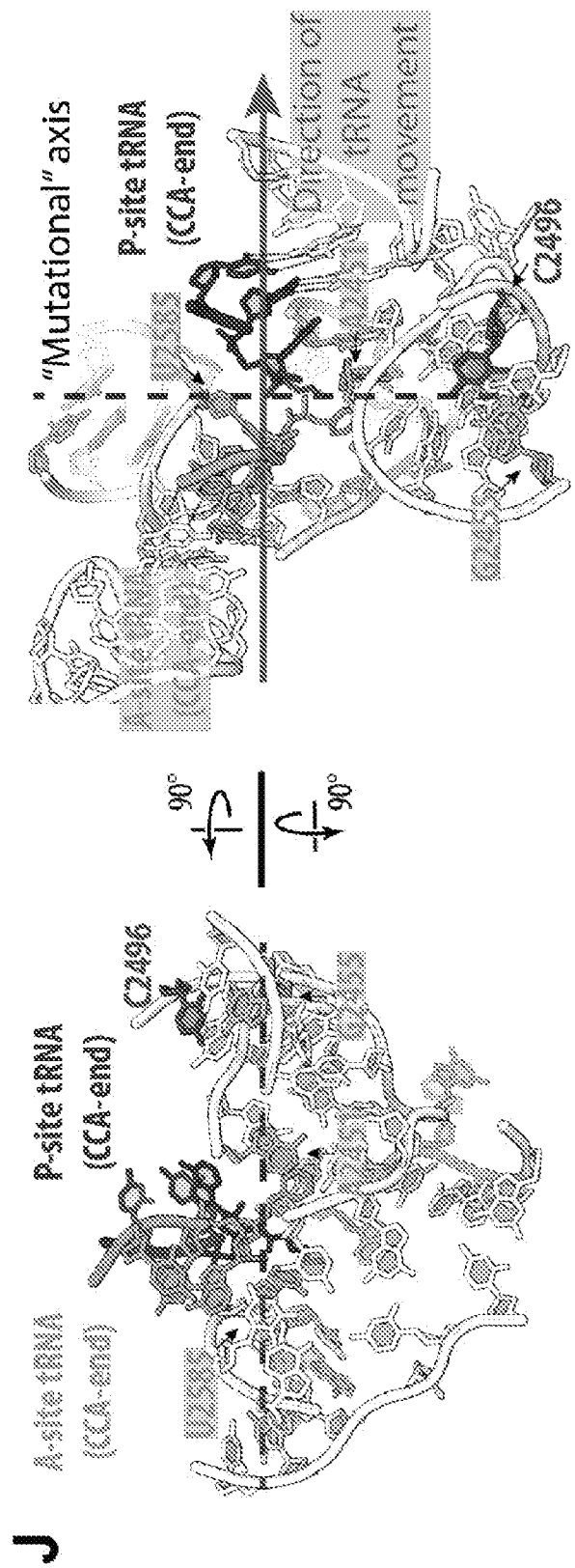
Figure 12:
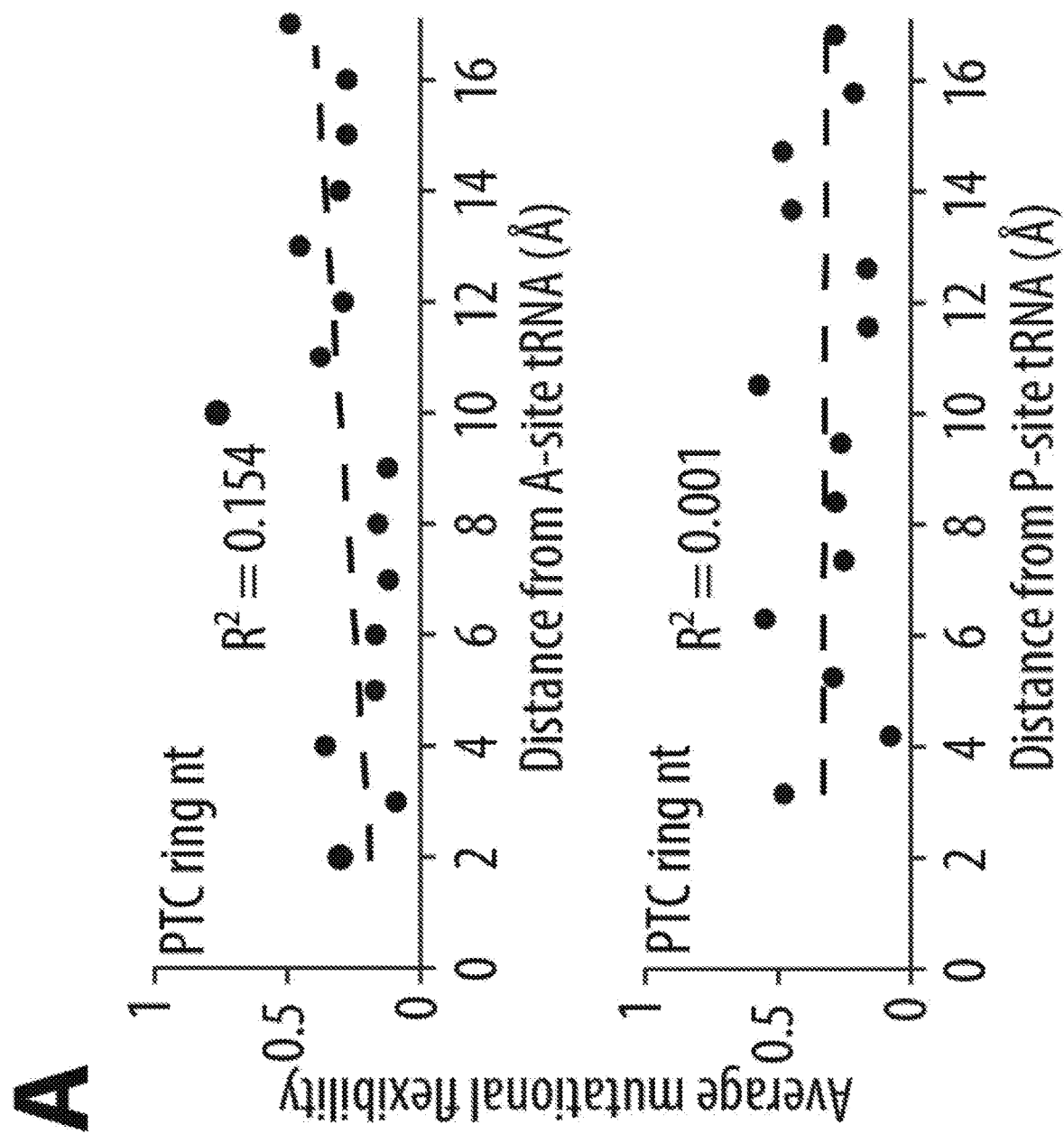
FIG. 12. Regression models of nucleotide distance against mutational flexibility. (A) Regression model of distance from A-site ($R^2$=0.154, p=0.13) and P-site ($R^2$=0.001, p=0.93) tRNA against mutational flexibility of PTC-ring nucleotides suggests a non-significant (p>0.05) and weak (low $R^2$ values) relationship. (B) Regression model of distance from A-site and P-site tRNA against mutational flexibility of A- (red) and P-loop (blue) nucleotides. The regression plots for the A-loop nucleotides possess $R^2$ values of 0.35 (p=0.03) and 0.32 (p=0.04), respectively. The regression plots for the P-loop nucleotides possess $R^2$ values of 0.61 (p=0.12) and 0.43 (p=0.23), respectively. The regressions and p-values for the A-site nucleotides suggests a significant and predictive relationship between mutational flexibility and distance from tRNA molecules; while the P-site nucleotides suggests a predictive relationship, however this relationship is non-significant due to a small sample size.
Figure 12:
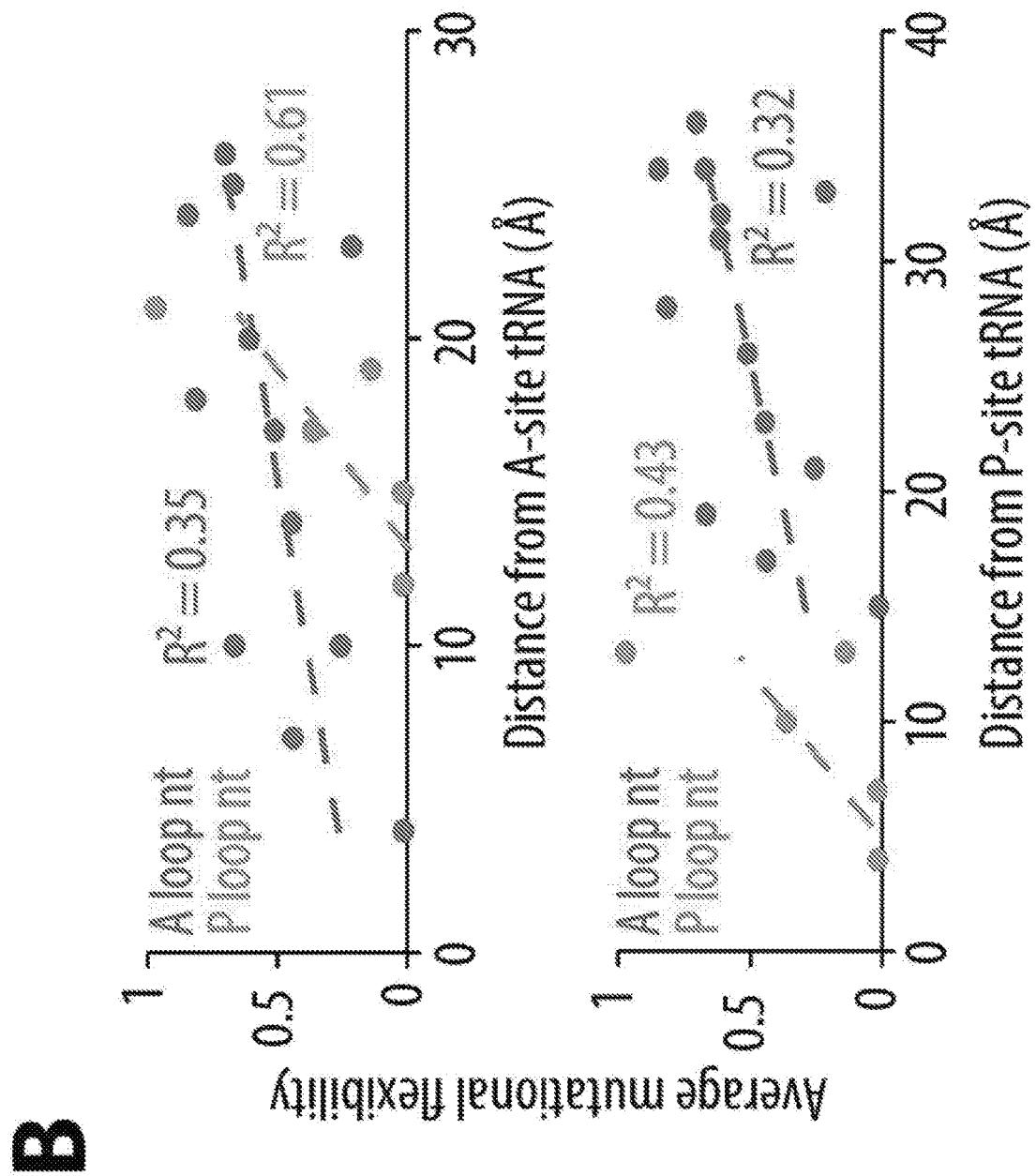

The ribosome's active site is composed of high- and low-flexibility pockets and shells. We next set out to map our analysis of mutational flexibility, translational readthrough, and ribosome assembly to the ribosome's three-dimensional structure, which would facilitate understanding of the PTC active site. Toward this goal we first wanted to gain insight into how proximity to tRNA molecules impacts mutational flexibility. We measured distances from A76 of the A- or P-site tRNAs to the average geometric center of each nucleotide (Table 6 and Table 7). We then organized the nucleotides in order of closest to furthest from the P-site tRNA (and compared to distances from the A-site tRNA). Upon generating a one-dimensional heat map, we find different patterns in the PTC-ring compared to the A- and P-loop (data not shown). Specifically, we found that the PTC-ring possesses pockets of high mutational flexibility and low mutational flexibility regardless of distance from tRNA molecules. Whereas in the A- and P-loops there exists a more evident gradient of flexibility and activity, with the nucleotides residing closest to the P-site tRNA (4 Å) having the least amount of activity upon mutation, and the nucleotides residing furthest from the P-site tRNA (36 Å) having the greatest mutant activity. By mapping our ribosome mutants' activity onto the 3D ribosomal crystal structure, we then generated a mutational flexibility map of the active site (FIG. 6). Upon deconvolution of the map into high-, medium-, and low-mutational flexibility groups, we found mutationally flexible and inflexible shells, pockets, and a gradient of flexibility in the PTC-ring, A-, and P-loops (FIG. 6 and FIG. 12). Furthermore, there were no major trends in maintaining high activity with nitrogenous base identity (purine vs pyrimidine) (data not shown). Within the PTC-ring, the first shell of nucleotides with the lowest mutational flexibility are shaded in red-magenta. Of these nucleotides, A2450, C2063, and C2501 possess the lowest mutational flexibility, and form a functionally critical pocket surrounding the P-site tRNA molecule with P-loop nucleotides G2252 and G2251 (FIG. 6D) (51). In the next shell, nucleotides possessing medium/low mutational flexibility are shaded in red-violet, and on average reside in closer proximity to the P-site tRNA than the A-site tRNA. This nucleotide group includes G2455, which possesses assembly defects when mutated to G2455A, as well as U2585 and A2451, which possess increased translation readthrough when mutated to U2585G and A2451U, respectively (FIG. 6E). The next shell of increasing mutational flexibility is shaded in violet. This shell of nucleotides spans both sides of the tRNA molecules and begins surrounding the exit tunnel (FIG. 6F). Finally, within the shell of highest mutational flexibility (violet-blue), there resides a prominent pocket surrounding the exit tunnel. Of note, this shell houses the nucleotide C2496, which possesses high translation readthrough when mutated to C2496G (FIG. 6G).

Within the A-loop nucleotides, there is a clear gradient of mutational flexibility, with the least flexible nucleotide being G2553 (red) and residing nearest to the A-site tRNA (4 angstroms). Importantly, this nucleotide makes key Watson-Crick interactions with the CCA-end (specifically C75) of the A-site tRNA (9) (FIG. 6H), while nucleotides possessing high mutational flexibility (violet-blue) make minimal contacts with the A-site tRNA molecule (FIGS. 6C and 6H). Much like the A-loop nucleotides, the P-loop nucleotides also possess a gradient of mutational flexibility corresponding with distance from the CCA-end of the P-site tRNA molecule. Importantly, the least mutationally flexible nucleotides, G2252 and G2251, make key Watson-Crick base pairing interactions with C75 and C76, respectively (FIGS. 6C and 6I). Interestingly, when modelled onto the heat map of the PTC-ring nucleotides with the lowest mutational flexibility, there is a clear pocket of translationally critical nucleotides that begin with Watson-Crick base pairing interactions at C75 and stretch down to the attached amino acid (FIG. 6D). Finally, For the A- and P-loops, we also analyzed regression models of distance from A-site and P-site tRNAs against mutational flexibility of A- (red) and P-loop (blue) nucleotides (FIG. 12). The regression plots for the A-loop nucleotides possess $R^2$ values of 0.35 ($p=0.03$) and 0.32 ($p=0.04$), respectively. The regression plots for the P-loop nucleotides possess $R^2$ values of 0.61 ($p=0.12$) and 0.43 ($p=0.23$), respectively. The regressions and p-values for the A-site nucleotides suggests a significant and predictive relationship between mutational flexibility and distance from tRNA molecules; while the P-site nucleotides suggests a predictive relationship, however this relationship is non-significant due to a small sample size.

We next combined our mutational flexibility maps with knowledge from the translation readthrough and assembly experiments. Upon analyzing the PTC-ring nucleotides with translation readthrough defects (C2496, U2585, and A2451), our mutational map highlights their unique positioning along the tRNA path through the ribosome (FIG. 6J). Additionally, G2455, which possesses an assembly defect, resides just behind the A-site tRNA molecule. Finally, the nucleotides with the highest (violet-blue) mutational flexibility and lowest (red-magenta) mutational flexibility, reside in pockets that span opposite sides of the tRNA molecules (FIGS. 6D and 6G). Upon analyzing regressions for the PTC-ring nucleotides' mutational flexibility against distance from each tRNA, we found no significant relationships (Distance from A-site tRNA: $R^2$=0.154, p=0.13; Distance from P-site tRNA: $R^2$=0.001, p=0.93), indicating that nucleotide distance alone does not explain the observed variation in mutational flexibility within this loop (FIG. 12).

Discussion

Here, using the iSAT platform, we designed, built, and characterized 180 single point mutations within the ribosome's active site. Importantly, the iSAT platform allowed us to rapidly produce (in hours) and study homogeneous populations of mutant E. coli ribosomes without contamination of wild type species (34). Upon characterizing these mutations, we discovered that despite the high degree of conservation within the ribosome's active site, many rRNA PTC nucleotides are still flexible to a variety of changes. We then carried out several assays to dissect functional and structural impacts of these mutations in a high-throughput way. We observed low translation readthrough across a subset of A- and P-loop mutants (C2559A, C2551A, U2552G, C2559A, C2551A, and U2552G). These results confirm previous hypotheses that these juxtaposed loops may play a role in tRNA selection by the ribosome. Specifically, upon aminoacyl-tRNA release from elongation factor-Tu, the A-loop may aid in accommodation of aminoacyl-tRNA into the A-site, permitting subsequent peptide-bond formation (52). Thus, binding of tRNA by the A-loop may act as a 50S checkpoint coupled to accommodation in the small subunit's decoding center. Furthermore, the results of our readthrough assay are consistent with the presence of all mutant ribosomes in polysomes (except for G2455A, which is present in polysomes but in very low amounts). These results corroborate previous studies indicating that base changes, such as those at A2451, are still capable of forming functional particles for protein synthesis (14).

Additional comparisons across our results are bolstered in previous publications. For instance, in their 1996 study, Porse and colleagues assayed rRNA mutants for peptidyl transferase activity in vitro using a fragment assay (53). They found that upon mutating U2585 to U2585G, this mutation retained 36% of its peptidyl transferase activity (21% activity in our work) whereas U2585A and U2585C were <6% active (~2% activity in our work). Furthermore, the authors found that G2253A, G2253U, and G2253C carried 19%, 42%, and <5% in vitro activity, respectively (in the same order: 55%, 40%, and 14% activity in our work). Additional mutants in their study possess activities comparable to ours. Furthermore, upon assaying incorporation of the mutated 23S rRNA into ribosomal particles, the authors found that U2585G possessed a 50S/70S incorporation ratio of 1.2 (in this work, the ratio is 1.3) (53).

In separate work conducted by Thompson and colleagues, the authors analyzed mutations at nucleotides A2451 and G2447. The authors found that A2451U assembled into 70S particles and accumulated in polysomes, however, at decreased levels compared to wild type—mirroring our results. Additionally, when probing translation readthrough, the authors demonstrated that A2451C and A2451U increased readthrough of a UGA premature stop codon ~2-fold (14). Similarly, our work shows UGA stop codon readthrough of ~1-fold and ~2-fold for A2451C, and A2451U, respectively. Finally, upon characterizing peptidyl transferase activity, the authors found A2451C decreases the rate of reaction ~3-fold. In our work the protein synthesis activity of A2451C is reduced 2-fold. These published results align well with our iSAT activity results; confirming that our platform is robust and generates assembled E. coli ribosomes with function that closely mimics that of the cell. Lastly, across the literature, there are commonly used antibiotic resistance mutations within the ribosome. A prime example is at positions A2062 and A2058. A2062U and A2058U confer macrolide resistance in E. coli and other bacteria. We would expect that if our results match the mutants' activity in the cell, that these well-studied PTC mutations would have high or almost wild-type activity. Indeed, in our results, we found that A2062U and A2058U possess 94% and 84% of wild-type activity, placing these nucleotides in the shell of "highly mutationally flexible nucleotides" on our map.

In summary, our work has resulted in a comprehensive mutational flexibility and characterization map of the ribosome's active site. This map corroborates previous work for nucleotides that have been studied, extends beyond previous knowledge to fill the gap in our understanding of the PTC, and illustrates a combination of biochemical and structural hypotheses surrounding the PTC. For instance, our map highlights (in red) the essential role of G2553, G2252, and G2251 in positioning tRNA molecules for peptidyl transfer (3,18,54), and the dependence of faithful hydrogen bonding within the triple-base pocket C2501•A2450•G2063 (51) (FIG. 6D). Our map also illustrates the flexibility and the dispensable nature of nucleotides surrounding the exit tunnel, offering new questions regarding the evolution and necessity of these positions (FIG. 6G). Finally, our map also demonstrates the complexity of rRNA loop arrangements within the ribosome. Our results indicate that a nucleotide's mutational flexibility, or dispensability, can be dependent on its position with respect to tRNA molecules (A- and P-loop flexibility gradients), or simply to neighboring nucleotides (PTC-ring mutational pockets and shells) (FIGS. 6A-C and 6J). Taken together, our results show that many active site mutated ribosomes can faithfully carry out protein synthesis, implying that these conserved nucleotides are not strictly indispensable for ribosome-catalyzed peptide bond formation.

Looking forward, we anticipate that our work may open new opportunities to engineer mutant ribosomes for novel purposes (20,55-62). Whether the engineering involves expanding the ribosome's exit tunnel (most mutationally flexible and dispensable) or co-evolving nucleotide pockets that appear to rely on key hydrogen bonding and base-pairing (the most mutationally inflexible nucleotides), our new systems-level understanding could help guide ribosome re-design (63). This in turn will increase our understanding the process of translation to advance new synthetic biology applications.

Tables

TABLE 1

Bulk translation rates of wild-type and representative mutant 70S iSAT ribosomes. Bulk translation rates for iSAT ribosomes were determined from protein synthesis kinetics curves, for reactions after 2 h incubations.

| rRNA Mutation | Bulk translation rate (µM protein/hr) |
|---|---|
| WT | 1.03 ± 0.03 |
| A2062U | 1.02 ± 0.02 |
| G2608C | 0.57 ± 0.03 |
| G2057U | 0.63 ± 0.02 |
| U2449C | 0.52 ± 0.02 |
| C2452A | 0.52 ± 0.02 |
| C2496G | 0.31 ± 0.02 |
| A2451C | 0.15 ± 0.01 |
| U2585G | 0.20 ± 0.01 |
| A2451U | 0.14 ± 0.01 |
| G2455A | 0.13 ± 0.01 |
| C2452G | 0.004 ± 0.01 |

TABLE 2

*E. coli* 23S rRNA PTC nucleotides and their published mutational studies.

| rRNA Nucleotide | Mutational studies | Reference |
|---|---|---|
| G2057 | G2057A confers low-level resistance to erythromycin in *E. coli*<br>G2057C remains unstudied<br>G2057U remains unstudied | Ettayebi, M., Prasad, S. M., and Morgan, E. A. J Bacteriol. 1985. 162(2): 551-557. |
| A2058 | A2058G confers macrolide resistance<br>A2058U confers clindamycin resistance<br>A2058C remains unstudied | Xiong et al. Antimicrob. Agents Chemother. 2005. 49(1): 281-288.<br>Cochella & Green. PNAS. 2004. 101(11): 3786-3791.<br>Prunier, A., et al. Antimicrob Agents Chemother. 2002. 46 (9): 3054-3056.<br>Pfister, P., et al. PNAS. 2005. 102(14) 5180-5. |
| A2059 | A2059G confers macrolide resistance in other bacteria (*E. coli* mutation unstudied)<br>A2059U remains unstudied<br>A2059C remains unstudied | Poehlsgaard, J., et al. Antimicrob Agents Chemother. 2005. 49 (4): 1553-1555. |
| A2060 | A2060G remains unstudied in *E. coli* (*M. bovis* exhibits tiamulin- and valnemulin resistance)<br>A2060U remains unstudied<br>A2060O remains unstudied due to lethality in vivo | Sulyok, K. et al. 2017. Antimicrob Agents Chemother. 61(2): e-01983-16.<br>Vester, B., and Garrett, R. 1988. EMBO Jour. 7(11): 3577-3587. |
| G2061 | G2061A remains unstudied in *E. coli* (antibiotic resistance in other bacteria-Pristinamycin resistant in *T. therophilus*)<br>G2061C remains unstudied in *E. coli*<br>G2061U remains unstudied in *E. coli* (tiamulin and valnemulin resistance in *M. gallisepticum* when in combination with other mutations: and clindamycin resistance in *T. gondii*) | Gregory, S. et al. 2005. J. Bacteriol. 187(14): 4804-4812<br>Li, B., et al. 2010. FEMS Microbiology letters. 308(2): 144-149.<br>Camps, M., et al. Mol. Microbiol. 2002. 43(5): 1309-18. |
| A2062 | A2062G confers clindamycin resistance in *E. coli*. Confers macrolide resistance in other bacteria<br>A2062U confers macrolide resistance in other bacteria<br>A2062C remains unstudied in *E. coli*. Confers 16-memberd macrolide resistance in *S. pneumoniae*. | Cochella & Green. PNAS. 2004. 101(11): 3786-3791.<br>Furneri, P. et al. 2001. Antimicrob Agents Chemother. 2001. 45 (10): 2958-2960.<br>Depardieu, F., and Courvalin, P. 2001. Antimicrob Agents Chemother. 2001, 45(1): 319-323. |
| C2063 | C2063A remains unstudied<br>C2063U only studied in the context of A2450G mutation. The combination of mutations decreases rate of peptide bond formation.<br>C2063G remains unstudied | Hesslein, A. E., et al. NAR. 2004. 32(12): 3760-3770. |
| G2447 | G2447A resistant to oxazolidinones<br>G2447U dominant lethal in vivo<br>G2447C resistant to streptomycin, but slow growth. | Babkova, E. V., et al. JBC. 2003. 278(11): 9802-9807.<br>Thompson, J., et al. PNAS. 2001. 98(16) 9002-9007. |
| A2448 | A2448C remains unstudied<br>A2448G remains unstudied<br>A2448U remains unstudied | |
| U2449 | U2449A strongly dominant lethal in vivo<br>U2449G strongly dominant lethal in vivo<br>U24490 viable with no impact on growth rate | Yassin, A. S. & Mankin, A. S. Journal of Biological Chemistry. 2007. 282 (33): 24329-24342.<br>O'Connor. M., et al. NAR. 2001. 239(3): 710-5. |
| A2450 | A2450G strongly dominant lethal in vivo<br>A2450U remains unstudied<br>A2450C remains unstudied | Yassin, A. S. & Mankin, A. S. Journal of Biological Chemistry. 2007. 282(33). 24329-24342. |
| A2451 | A2451U strongly dominant lethal in vivo<br>A2451G strongly dominant lethal in vivo. Deficient in early assembly steps of large subunit.<br>A2451C peptidyltransferase reaction rate reduced by ~4-fold | Yassin, A. S. & Mankin, A. S. Journal of Biological Chemistry. 2007. 282(33). 24329-24342.<br>Thompson. J., et al. PNAS. 2001. 98(16): 9002-9007. |
| C2452 | C2452A remains unstudied<br>C2452U confers anisomycin resistance in *H. maristmortui* and *S. cerevisiae*<br>C2452G remains unstudied | Blaha. G., et al. J. Mol. Biol. 2008, 379(3): 505-519 |
| A2453 | A2453C confers resistance to anisomycin and to linezolid in *H. halobium*. Decreased growth rate.<br>A2453G strongly dominant lethal in vivo<br>A2453U confers resistance to anisomycin in *H. marismortui*. | Kloss, P., et al. JMB. 1999. 294: 93-101.<br>Yassin, A. S. & Mankin, A. S. Journal of Biological Chemistry. 2007. 282 (33): 24329-24342.<br>Blaha, G., et al. J. Mol. Biol. 2008, 379(3): 505-519 |
| G2454 | G2454A moderately dominant lethal in vivo<br>G2454U remains unstudied<br>G2454C remains unstudied | Yassin, A. S. & Mankin, A. S. Journal of Biological Chemistry. 2007. 282 (33): 24329-24342. |
| G2455 | G2455A remains unstudied<br>G2455U remains unstudied<br>G2455C remains unstudied | |
| C2456 | C2456A remains unstudied<br>C2456U remains unstudied<br>C2456G remains unstudied | |
| C2496 | C2496A remains unstudied<br>C2496U remains unstudied<br>C2496G remains unstudied | |

TABLE 2-continued

E. coli 23S rRNA PTC nucleotides and their published mutational studies.

| rRNA Nucleotide | Mutational studies | Reference |
|---|---|---|
| A2497 | A2497C remains unstudied<br>A2497G strongly defective in peptidyl transferase activity activity<br>A2497U remains unstudied | Porse, B. T., and Garrett, R. A. JMB. 1995. 249, 1-10. |
| C2498 | C2498A remains unstudied<br>C2498U remains unstudied<br>C2498G remains unstudied | |
| C2499 | C2499A alone or when paired with G2032A confers linezolid resistance<br>C2499U strongly dominant lethal in vivo<br>C2499G remains unstudied | Fulle, S., Et al. NAR. 2015 43(16): 7731-7743.<br>Yassin, A. S. & Mankin, A. S. Journal of Biological Chemistry. 2007. 282 (33): 24329-24342. |
| U2500 | U2500A confers anisomycin resistance in H. marismortui<br>U2500G remains unstudied<br>U2500C confers anisomycin resistance in H. marismortui. Confers linezolid resistance in E. coli and H. halobium. | Blaha, G., et al. J. Mol. Biol. 2008. 379(3): 505-519.<br>Xion. L. Q., et al. J. BacteriOl. 2000. 182: 5325-5331. |
| C2501 | C2501A remains unstudied<br>C2501U remains unstudied<br>C2501G remains unstudied | |
| G2502 | G2502A causes a decreasesd growth rate in E. coli.<br>G2502U remains unstudied<br>G2502C remains unstudied | Vester, B. and Garrett, R. A. EMBO J. 1988. 7(11): 3577-3587. |
| A2503 | A2503C leads to increased resistance to proline-rich antimicrobial peptide Onc112 (especially when combined with A2059C).<br>A2503G confers a small susceptibility to linezolid antibiotic in M. smegmatis (E. coli mutation unstudied)<br>A2503U confers resistance to valnemulin, chloramphenicol, florfenical, tylosin, spiramycin, josamycin, and linezolid in M. smegmatis (E. coli mutation unstudied) | Ganon, M. G., et al. NAR. 2016 44: 2439-2450.<br>Long. K. S., et al. Antimicrob Agents Chemother. 2010. 54 (11): 4705-4713.<br>Li, B. B., et al. J. Antimicrob. Chemother. 2011. 66(9): 1983-6. |
| U2504 | U2504A confer chloramphenicol resistance in mitochondrial rRNA (E. coli mutation unstudied).<br>U2504G growth rate increases to 5.4 h. Cross resistance to both chloramphenicol and linezelid in M. smegmatis (E. coli mutation unstudied).<br>U2504C confers linezolid resistance in H. halobium (E. coli mutation unstudied). | Long. K. S., et al. Molecular Microbiology. 2009. 71(5): 1218-1217. |
| G2505 | G2505A confers resistance to oxazolidinone linezolid in Enterococcus faecalis. E. coli mutation studied in vitro shows 14% peptidyl transferase activity. Severe to lethal growth defects in vivo.<br>G2505U shows less than 5% peptidyl transferase activity in vitro. Severe to lethal growth defects in vivo.<br>G2505C shows 17% peptidyl transferase activity in vitro. Severe to lethal growth defects in vivo. When combined with A1067U, mutation is dominant lethal. | Bourgeois-Nicolaos, N. et al. J. Infect. Dis. 2007. 195(10): 1480-8.<br>Saarma, U., and Remme, J. NAR. 1992. 20: 3147-3152.<br>Porse, B. T., et al. JMB. 1996. 264: 472-483. |
| U2506 | U2506A impacts ability to catalyze peptidyltransferase with Puromycin. Retains 5% peptidyl transferase activity in vitro. Lethal in vivo.<br>U2506G displays a cold-sensitive phenotype in which peptide bond formation is efficient at higher temperatures. Retains less than 5% peptidyl transferase activity in vitro. Lethal in vivo. | Youngman, E. M., et al. Cell. 2004. 117(5): 589-599.<br>Porse, B. T., et al. JMB. 1996. 264: 472-483. |
| | U2506C impacts ability to catalyze peptidyltransferase with Puromycin. Retains 20% peptidyl transferase activity in vitro. Lethal in vivo. | |
| C2507 | C2507A remains unstudied<br>C2507U dominant lethal in vivo.<br>C2507G remains unstudied | Spahn, C., et al. JBC. 1996, 271: 32849-32856. |
| G2582 | G2582A decreased total protein synthesis by approximately one-third, but not the RNA synthesis, Additionally, this mutation results in an increase in peptidyl-tRNA drop-off, thereby reducing translational processivity. Shows less than 5% peptidyl transferase activity in vitro. Lethal in vivo.<br>G2582U causes a significant increase in peptidyl-tRNA drop-off from ribosomes. thereby reducing translational processivity. Retains less than 5% peptidyl transferase activity in vitro. Lethal in vivo<br>G2582C retains <5% peptidyl transferase activity in vitro. Lethal in vivo. | Maivali, U., et al. Mol. Biol. (Mosk). 2001. 35 (4): 666-71.<br>Porse, B. T., et al. JMB. 1996, 264: 472-483. |
| G2583 | G2583A readily incorporates into 70S ribosomes and polysomes. When combined with A1067U, mutation is dominant lethal. Alone, mutation is results in very little activity in vitro (less than 5%), growth defects in vivo.<br>G2583U retains less than 5% peptidyl transferase activity in vitro. Lethal in vivo.<br>G2583C decreased total protein synthesis by approximately one-third, but not the RNA synthesis. Additionally, this mutation results in an increase in peptidyl-tRNA drop-off, thereby reducing translational processivity. Other studies show this mutation has <5% or no peptidyl transferase activity in vitro. Lethal in vivo. | Saarma, U., et al. RNA. 1998. 4: 189-194.<br>Saarma, U., and Remme, J. NAR. 1992. 20: 3147-3152.<br>Maivali, U., et al. Mol. Biol. (Mosk). 2001. 35 (4): 666-71.<br>Parse, B. T., et al. JMB. 1996. 264: 472-483. |
| U2584 | U2584A retains 22% peptidyl transferase activity in vitro. Lethal in vivo.<br>U2584G dominant lethal in vivo. Retains 32% peptidyl transferase activity in vitro.<br>U2584C retains 21% peptidyl transferase activity in vitro. Some growth defect in vivo. | Porse, B. T., and Garrett, R. A. JMB, 1995, 249: 1-10.<br>Maivali, U., et al. Mol. Biol. (Mosk). 2001. 35(4): 666-71. |
| U2585 | U2585A lethal in vivo. Causes degradation of both large and small ribosomal subunits in E. coli. Retains 6% peptidyl transferase activity in vitro.<br>U2585G lethal in vivo. Peptidyltransferase rate constant is diminished in vitro by ~7-fold. Retains 36% peptidyl transferase activity in vitro.<br>U2585C lethal in vivo. Peptide release is compromised in vitro. Retains less than 5% peptidyl transferase activity in vitro. | Paier, A., et al. Sci. Rep. 2015. 5: 7712.<br>Youngman, E. M., et al. Cell. 2004. 117: 589-599.<br>Porse, B. T., et al. JMB. 1996. 264: 472-483. |
| U2586 | U2586A does not affect wild-type ErmCL peptide stalling.<br>U2586G does not affect wild-type ErmCL peptide stalling.<br>U2586C does not affect wild-type ErmCL peptide stalling. | Arenz. S., et al. Molecular Cell. 2014. 56: 446-452. |
| A2587 | A2587C remains unstudied.<br>A2587G remains unstudied.<br>A2587U remains unstudied. | |

TABLE 2-continued

E. coli 23S rRNA PTC nucleotides and their published mutational studies.

| rRNA Nucleotide | Mutational studies | Reference |
|---|---|---|
| G2588 | G2588A alters the interaction of protein substrates and the antiprion compound 6-Aminophenanthridine (6AP) with domain V rRNA, and also decreases protein folding activity of the ribosome (PFAR)<br>G2588U remains unstudied.<br>G2588C remains unstudied. | Pang, Y., et al. JBC. 2013. 288(26): 19081-19089. |
| A2602 | A2602C completely eliminates RF1-dependent peptidyl-tRNA hydrolysis.<br>A2602G has diminished peptide release activity.<br>A2602U has diminished peptide release activity. | Polacek, N., et al. Molecular Cell. 2003. 11(1): 103-112. |
| C2606 | C2606A remains unstudied.<br>C2606U remains unstudied.<br>C2606G remains unstudied. | |
| G2607 | G2607A remains unstudied.<br>G2607U remains unstudied.<br>G2607C remains unstudied. | |
| G2608 | G2608A does not confer resistance to oxazolidinone antibiotic.<br>G2608U confers resistance to oxazolidinone antibiotic.<br>G2608C confers strong resistance to oxazolidinone antibiotic. | Xu, J., et al. Biochemical and Biophysical Research Communications. 2005. 328(2): 471-476. |
| U2609 | U2609A results in resistance to klebsazolicin (KLB).<br>U2609G results in resistance to klebsazolicin (KLB).<br>U2609C renders E. coli resistant to ketolides telithromycin and cethromycin | Metelev. M., et al. Nature Chemical Biology. 2017. 13: 1129-1136.<br>Xiong, L., et al. Antimicrob Agents Chemother. 2005. 49 (1): 281-288. |
| C2610 | C2610A remains unstudied.<br>C2610U in S. pneumoniae confers small impacts on the activities of macrolides and clindamycin, but is not categorized as resistance to these antimicrobials.<br>Reduces Erythromycin-dependent ribosome stalling of ErmCL peptide in E. coli.<br>C2610G is associated with linezolid resistance in E. faecalis. Remains unstudied in E. coli. | Canu, A., et al. Antimicrob. Agents. Chemother. 2002. 46 (1): 125-131.<br>Vazquez-Laslop. N. et al. PNAS. 2011. 108: 10496-10501.<br>Boumghar-Bourtchai, L.; et al. Antimicrob. Agents. Chemother. 2009. 53(9): 4007-4009. |
| C2611 | C2611A confers resistance to erythromycin and 14- and 15-membered macrolides in pneumococcal strains.<br>C2611U in S. pneumoniae confers small impacts on the activities of macrolides and clindamycin, but is not categorized as resistance to these antimicrobials. Remains unstudied in E. coli.<br>C2611G confers resistance to erythromycin and 14- and 15-membered macrolides in pneumococcal strains. | Canu, A., et al. Antimicrob. Agents. Chemother. 2002. 46(1): 125-131.<br>Tait-Kamradt, A., et al. Antimicrob. Agents. Chemother. 2000. 44(8): 2118-2125. |

TABLE 3

Bulk translation rates of wild-type and PTC-ring mutant 70S iSAT ribosomes. Bulk translation rates for iSAT ribosomes were determined from protein synthesis kinetics curves, for reactions after 2 h incubations, and normalized to wild-type.

| Mutant | Average μM sfGFP | Bulk translation rate (μM protein/hr) | Std. Dev |
|---|---|---|---|
| wt pT7rrnb | 1.00 | 1.03 | 0.03 |
| G2505U | 0.98 | 0.85 | 0.02 |
| A2062U | 0.94 | 1.02 | 0.02 |
| C2496U | 0.90 | 0.74 | 0.02 |
| G2608A | 0.90 | 0.58 | 0.02 |
| A2058C | 0.89 | 0.69 | 0.03 |
| A2587U | 0.83 | 0.80 | 0.04 |
| A2058U | 0.82 | 0.81 | 0.03 |
| G2583A | 0.82 | 0.53 | 0.02 |
| U2609A | 0.80 | 0.55 | 0.01 |
| A2503U | 0.79 | 0.64 | 0.02 |
| G2608U | 0.78 | 0.67 | 0.02 |
| G2608C | 0.77 | 0.57 | 0.03 |
| G2057U | 0.77 | 0.63 | 0.02 |
| U2609C | 0.74 | 0.47 | 0.02 |
| A2062C | 0.72 | 0.46 | 0.02 |
| U2609G | 0.68 | 0.39 | 0.03 |
| A2497U | 0.67 | 0.48 | 0.01 |
| C2456U | 0.66 | 0.43 | 0.10 |
| U2584A | 0.66 | 0.44 | 0.02 |
| U2449C | 0.64 | 0.52 | 0.02 |
| A2062G | 0.63 | 0.43 | 0.02 |
| C2452A | 0.61 | 0.52 | 0.02 |
| U2504G | 0.60 | 0.40 | 0.01 |
| A2058G | 0.57 | 0.51 | 0.02 |
| G2057C | 0.57 | 0.52 | 0.01 |
| U2586G | 0.57 | 0.52 | 0.01 |
| A2453U | 0.57 | 0.34 | 0.03 |
| G2588U | 0.56 | 0.38 | 0.01 |
| U2584C | 0.56 | 0.38 | 0.02 |
| C2611U | 0.65 | 0.42 | 0.02 |
| G2607C | 0.50 | 0.45 | 0.02 |
| A2448C | 0.49 | 0.30 | 0.04 |
| A2448U | 0.48 | 0.21 | 0.02 |
| U2586A | 0.47 | 0.36 | 0.00 |
| G2057A | 0.47 | 0.33 | 0.02 |
| G2588C | 0.47 | 0.49 | 0.02 |
| G2607U | 0.47 | 0.09 | 0.01 |
| U2586C | 0.44 | 0.31 | 0.04 |
| G2447A | 0.44 | 0.20 | 0.01 |
| C2606U | 0.42 | 0.30 | 0.01 |
| C2610G | 0.41 | 0.49 | 0.02 |
| A2059G | 0.40 | 0.26 | 0.01 |
| C2496G | 0.38 | 0.31 | 0.02 |
| A2448G | 0.37 | 0.28 | 0.04 |
| U2500A | 0.36 | 0.30 | 0.03 |
| A2451C | 0.36 | 0.15 | 0.01 |
| U2504A | 0.35 | 0.19 | 0.00 |
| G2588A | 0.35 | 0.28 | 0.01 |
| G2582U | 0.34 | 0.37 | 0.03 |
| C2610U | 0.33 | 0.25 | 0.02 |
| G2502U | 0.29 | 0.19 | 0.01 |
| A2503G | 0.28 | 0.34 | 0.02 |
| G2455U | 0.27 | 0.16 | 0.01 |
| A2060G | 0.27 | 0.17 | 0.01 |
| A2497G | 0.26 | 0.12 | 0.01 |
| U2584G | 0.25 | 0.11 | 0.02 |
| G2447C | 0.25 | 0.17 | 0.01 |
| G2061A | 0.23 | 0.35 | 0.02 |
| A2059U | 0.22 | 0.33 | 0.02 |
| U2585G | 0.21 | 0.20 | 0.01 |
| U2504C | 0.21 | 0.16 | 0.01 |
| C2606A | 0.20 | 0.15 | 0.01 |
| A2587G | 0.20 | 0.02 | 0.01 |
| G2607A | 0.20 | 0.15 | 0.01 |
| A2059C | 0.18 | 0.09 | 0.01 |
| C2496A | 0.16 | 0.11 | 0.01 |
| C2606G | 0.15 | 0.05 | 0.02 |
| C2507U | 0.15 | 0.05 | 0.01 |
| A2453C | 0.15 | 0.05 | 0.02 |
| G2454A | 0.13 | 0.09 | 0.02 |
| U2449A | 0.12 | 0.02 | 0.00 |

TABLE 3-continued

Bulk translation rates of wild-type and PTC-ring mutant 70S iSAT ribosomes. Bulk translation rates for iSAT ribosomes were determined from protein synthesis kinetics curves, for reactions after 2 h incubations, and normalized to wild-type.

| Mutant | Average μM sfGFP | Bulk translation rate (μM protein/hr) | Std. Dev |
|---|---|---|---|
| C2611A | 0.11 | 0.03 | 0.01 |
| G2505A | 0.10 | 0.00 | 0.00 |
| A2451U | 0.10 | 0.14 | 0.01 |
| A2497C | 0.10 | 0.13 | 0.01 |
| A2587C | 0.09 | 0.04 | 0.01 |
| C2456G | 0.09 | 0.06 | 0.00 |
| C2456A | 0.08 | 0.06 | 0.00 |
| G2583U | 0.07 | 0.03 | 0.00 |
| C2498U | 0.06 | 0.00 | 0.00 |
| G2455A | 0.06 | 0.13 | 0.01 |
| G2061C | 0.06 | 0.02 | 0.01 |
| G2454U | 0.04 | 0.01 | 0.00 |
| C2499G | 0.04 | 0.03 | 0.01 |
| G2502C | 0.04 | 0.02 | 0.01 |
| C2610A | 0.04 | 0.00 | 0.00 |
| C2501U | 0.03 | 0.02 | 0.01 |
| U2506G | 0.03 | 0.02 | 0.02 |
| C2452G | 0.03 | 0.00 | 0.01 |
| C2611G | 0.03 | 0.00 | 0.00 |
| A2602U | 0.03 | 0.02 | 0.00 |
| C2452U | 0.02 | 0.02 | 0.02 |
| U2585A | 0.02 | 0.02 | 0.03 |
| A2602G | 0.02 | 0.01 | 0.01 |
| G2455C | 0.02 | 0.02 | 0.00 |
| U2506C | 0.02 | 0.01 | 0.01 |
| U2506A | 0.02 | 0.02 | 0.01 |
| U2585C | 0.02 | 0.01 | 0.01 |
| A2451G | 0.02 | 0.00 | 0.00 |
| G2582A | 0.02 | 0.00 | 0.00 |
| G2502A | 0.02 | 0.01 | 0.00 |
| A2602C | 0.02 | 0.01 | 0.00 |
| A2450G | 0.02 | 0.00 | 0.00 |
| U2449G | 0.02 | 0.01 | 0.01 |
| C2499U | 0.01 | 0.00 | 0.00 |
| G2447U | 0.01 | 0.00 | 0.00 |
| G2505C | 0.01 | 0.49 | 0.10 |
| A2503C | 0.01 | 0.31 | 0.02 |
| C2499A | 0.01 | 0.03 | 0.00 |
| G2583C | 0.01 | 0.00 | 0.00 |
| A2060U | 0.00 | 0.00 | 0.01 |
| U2500G | 0.00 | 0.01 | 0.00 |
| A2453G | 0.00 | 0.01 | 0.00 |
| C2501G | 0.00 | 0.00 | 0.00 |
| C2063U | 0.00 | 0.00 | 0.00 |
| G2061U | 0.00 | 0.02 | 0.00 |
| C2507A | 0.00 | 0.00 | 0.00 |
| A2450U | 0.00 | 0.00 | 0.00 |
| C2501A | 0.00 | 0.00 | 0.00 |
| C2063G | 0.00 | 0.00 | 0.00 |
| A2060C | 0.00 | 0.02 | 0.00 |
| C2063A | 0.00 | 0.00 | 0.00 |
| A2450C | 0.00 | 0.00 | 0.00 |
| G2454C | 0.00 | 0.00 | 0.00 |
| C2498A | 0.00 | 0.00 | 0.01 |
| C2498G | 0.00 | 0.00 | 0.02 |
| U2500C | 0.00 | 0.06 | 0.02 |
| C2507G | 0.00 | 0.01 | 0.00 |
| G2582C | 0.00 | 0.00 | 0.00 |

TABLE 4

Equations and examples scores for relative activity calculations, and overall mutational flexibility scores.

| Value/Score | Equation used | Example calculations | |
|---|---|---|---|
| | | Protein synthesis yields | Relative activity |
| Relative activity | $R = \dfrac{1}{WT} *$ (Mutant activity) | WT: 9.6 μM<br>A2062U: 9.0 μM<br>A2062C: 6.9 μM<br>A2062G: 6.0 μM | WT: 1<br>A2062U: 0.94<br>A2062C: 0.72<br>A2062G: 0.63 |
| | | Relative activity | Mutational flexibility |
| Mutational flexibility | R1 + R2 + R3 | A2062U: 0.94<br>A2062C: 0.72<br>A2062G: 0.63 | A2062: 2.3 |

Relative activity was calculated to compare performance of each mutant by normalizing wild-type protein synthesis yields to one and mutant yields to the normalized wild-type yields.
An overall mutational flexibility score was then determined for each nucleotide position by adding the relative activities of every possible point mutation.
The highest mutational flexibility score of three indicates that all three nucleotide changes possess wild-type activity, while the lowest mutational flexibility score of zero indicates that all three nucleotide changes preclude any protein synthesis.

TABLE 5

Sucrose gradient fractionation profiles of rRNA PTC mutants. Representative nucleotide mutations were chosen for sucrose gradient fractionation based on their activity. iSAT reactions were separated through sucrose gradients, and fractions were collected. The relative average abundance of rRNA in each fraction was quantified by calculating the area under each curve. Nucleotides shaded in grey represent representative A- and P-loop nucleotide traces.

| Ribosomes | 30S | 50S | 70S | Polysomes | Relative Subunits: 70S + Polysomes | Relative 70S: Polysomes |
|---|---|---|---|---|---|---|
| WT | 48% | 21% | 26% | 5% | 2.23 | 5.2 |
| A2062U | 44% | 21% | 27% | 9% | 1.81 | 3.0 |
| G2057U | 48% | 23% | 24% | 5% | 2.45 | 4.8 |
| C2496G | 53% | 18% | 28% | 2% | 2.37 | 13.8 |
| A2451C | 44% | 26% | 27% | 3% | 2.33 | 9.0 |
| U2585G | 26% | 38% | 29% | 7% | 1.77 | 3.9 |
| A2451U | 26% | 38% | 32% | 4% | 1.80 | 8.4 |
| G2455A | 50% | 29% | 16% | 4% | 3.95 | 4.0 |
| C2452G | 52% | 19% | 28% | 1% | 2.45 | 28.0 |

TABLE 5-continued

Sucrose gradient fractionation profiles of rRNA PTC mutants. Representative nucleotide mutations were chosen for sucrose gradient fractionation based on their activity. iSAT reactions were separated through sucrose gradients, and fractions were collected. The relative average abundance of rRNA in each fraction was quantified by calculating the area under each curve. Nucleotides shaded in grey represent representative A-and P-loop nucleotide traces.

| Ribosomes | 30S | 50S | 70S | Polysomes | Relative Subunits: 70S + Polysomes | Relative 70S: Polysomes |
|---|---|---|---|---|---|---|
| WT | 28% | 20% | 39% | 13% | 0.92 | 3 |
| C2559A | 30% | 23% | 32% | 15% | 1.12 | 2.1 |
| C2551A | 30% | 23% | 31% | 16% | 1.12 | 1.9 |

TABLE 6

PTC-ring nucleotide distances calculated in PyMol. PTC nucleotide distances were calculated from either the A-site or P-site tRNAs. Using the E. coli ribosome structure (PDB-4YBB), we measured the distance between A76 of the A-site and P-site tRNAs and within one angstrom of the geometric center of each PTC nucleotide.

| A site (A76 of A-site tRNA + AA) | | P site (A76 of P-site tRNA + AA) | |
|---|---|---|---|
| Distance | Nucleotides | Distance | Nucleotides |
| 2 Å or less | 2583 | 3 Å or less | 2062, 2585 |
| 3 Å or less | 2506, 2451, 2585 | 4 Å or less | 2061, 2063, 2450, 2451 |
| 4 Å or less | 2584, 2452 | | |
| 5 Å or less | 2061, 2505, 2507 | 5 Å or less | 2586, 2602 |
| 6 Å or less | 2063, 2504, 2582 | 6 Å or less | 2584 |
| 7 Å or less | 2447, 2450 | 7 Å or less | 2452 |
| 8 Å or less | 2501, 2503, 2453, 2602 | 8 Å or less | 2503, 2505, 2506 |
| 9 Å or less | 2500 | 9 Å or less | 2447, 2501, 2504, 2583, |
| 10 Å or less | 2062 | 10 Å or less | 2497, 2587, 2608 |
| 11 Å or less | 2586, 2610 | 11 Å or less | 2059, 2449 |
| 12 Å or less | 2059, 2454, 2499, 2608 | 12 Å or less | 2453, 2507 |
| 13 Å or less | 2058, 2449, 2497 | 13 Å or less | 2496, 2500, 2609, 2610 |
| 14 Å or less | 2502, 2496, 2607, 2611 | 14 Å or less | 2058, 2502, 2588, 2607 |
| 15 Å or less | 2057, 2455, 2498, 2587, 2606 | 15 Å or less | 2060, 2499, 2582, 2606, 2611 |
| 16 Å or less | 2060, 2588 | 16 Å or less | 2057, 2448, 2454, 2455, 2498 |
| 17 Å or less | 2448, 2456, 2609 | | |

TABLE 7

A- and P-loop nucleotide distances calculated in PyMol. Distances were calculated from either the A-site or P-site tRNAs. Using the E. coli ribosome structure (PDB-4YBB), we measured the distance between A76 of the A-site and P-site tRNAs and within one angstrom of the geometric center of each PTC nucleotide.

| A site (A76 of A-site tRNA + AA) | | P site (A76 of P-site tRNA + AA) | |
|---|---|---|---|
| Distance | Nucleotides | Distance | Nucleotides |
| 4 Å or less | 2553 | 4 Å or less | 2251 |
| 7 Å or less | 2554 | 7 Å or less | 2252 |
| 10 Å or less | 2552, 2555 | 10 Å or less | 2253 |
| 12 Å or less | 2251 | 13 Å or less | 2250, 2254 |
| 14 Å or less | 2556 | 15 Å or less | 2553 |
| 15 Å or less | 2252 | 17 Å or less | 2554 |
| 17 Å or less | 2253, 2557 | 19 Å or less | 2555 |
| 18 Å or less | 2551 | 21 Å or less | 2552 |
| 19 Å or less | 2250 | 23 Å or less | 2556 |
| 20 Å or less | 2550, 2558 | 26 Å or less | 2557 |
| 21 Å or less | 2254 | 28 Å or less | 2551 |
| 23 Å or less | 2549 | 31 Å or less | 2558 |
| 24 Å or less | 2559 | 32 Å or less | 2550 |

TABLE 7-continued

A- and P-loop nucleotide distances calculated in PyMol. Distances were calculated from either the A-site or P-site tRNAs. Using the E. coli ribosome structure (PDB-4YBB), we measured the distance between A76 of the A-site and P-site tRNAs and within one angstrom of the geometric center of each PTC nucleotide.

| A site (A76 of A-site tRNA + AA) | | P site (A76 of P-site tRNA + AA) | |
|---|---|---|---|
| Distance | Nucleotides | Distance | Nucleotides |
| 25 Å or less | 2548 | 33 Å or less | 2549 |
| 26 Å or less | 2560 | 34 Å or less | 2559, 2548 |
| | | 36 Å or less | 2560 |

REFERENCES

1. Nissen, P., Hansen, J., Ban, N., Moore, P. B. and Steitz, T. A. (2000) The Structural Basis of Ribosome Activity in Peptide Bond Synthesis. Science, 289, 920-930.
2. Polacek, N. and Mankin, A. S. (2005) The ribosomal peptidyl transferase center: structure, function, evolution, inhibition. Crit Rev Biochem Mol Biol, 40, 285-311.
3. Kim, D. F. and Green, R. (1999) Base-pairing between 23S rRNA and tRNA in the ribosomal A site. Mol Cell, 4, 859-864.
4. Samaha, R. R., Green, R. and Noller, H. F. (1995) A base pair between tRNA and 23S rRNA in the peptidyl transferase centre of the ribosome. Nature, 377, 309-314.
5. Marks, J., Kannan, K., Roncase, E. J., Klepacki, D., Kefi, A., Orelle, C., Vázquez-Laslop, N. and Mankin, A. S. (2016) Context-specific inhibition of translation by ribosomal antibiotics targeting the peptidyl transferase center. Proceedings of the National Academy of Sciences, 113, 12150-12155.
6. Beringer, M. and Rodnina, M. V. (2007) The Ribosomal Peptidyl Transferase. Molecular Cell, 26, 311-321.
7. Arenz, S., Ramu, H., Gupta, P., Berninghausen, O., Beckmann, R., Vazquez-Laslop, N., Mankin, A. S. and Wilson, D. N. (2014) Molecular basis for erythromycin-dependent ribosome stalling during translation of the ErmBL leader peptide. Nat Commun, 5, 3501.
8. Gumbart, J., Schreiner, E., Wilson, Daniel N., Beckmann, R. and Schulten, K. (2012) Mechanisms of SecM-Mediated Stalling in the Ribosome. Biophysical Journal, 103, 331-341.
9. Brunelle, J. L., Youngman, E. M., Sharma, D. and Green, R. (2006) The interaction between C75 of tRNA and the A loop of the ribosome stimulates peptidyl transferase activity. RNA, 12, 33-39.

10. Green, R., Switzer, C. and Noller, H. F. (1998) Ribosome-catalyzed peptide-bond formation with an A-site substrate covalently linked to 23S ribosomal RNA. Science, 280, 286-289.
11. Beringer, M. and Rodnina, M. V. (2007) Importance of tRNA interactions with 23S rRNA for peptide bond formation on the ribosome: studies with substrate analogs. Biol Chem, 388, 687-691.
12. Kaczanowska, M. and Rydén-Aulin, M. (2007) Ribosome biogenesis and the translation process in *Escherichia coli*. Microbiology and Molecular Biology Reviews, 71, 477-494.
13. Ogle, J. M., Carter, A. P. and Ramakrishnan, V. (2003) Insights into the decoding mechanism from recent ribosome structures. Trends Biochem Sci, 28, 259-266.
14. Thompson, J., Kim, D. F., O'Connor, M., Lieberman, K. R., Bayfield, M. A., Gregory, S. T., Green, R., Noller, H. F. and Dahlberg, A. E. (2001) Analysis of mutations at residues A2451 and G2447 of 23S rRNA in the peptidyltransferase active site of the 50S ribosomal subunit. Proceedings of the National Academy of Sciences of the United States of America, 98, 9002-9007.
15. Youngman, E. M., Brunelle, J. L., Kochaniak, A. B. and Green, R. The Active Site of the Ribosome Is Composed of Two Layers of Conserved Nucleotides with Distinct Roles in Peptide Bond Formation and Peptide Release. Cell, 117, 589-599.
16. Yassin, A. and Mankin, A. S. (2007) Potential new antibiotic sites in the ribosome revealed by deleterious mutations in RNA of the large ribosomal subunit. J Biol Chem, 282, 24329-24342.
17. Lieberman, K. R. and Dahlberg, A. E. (1994) The importance of conserved nucleotides of 23 S ribosomal RNA and transfer RNA in ribosome catalyzed peptide bond formation. J Biol Chem, 269, 16163-16169.
18. Green, R., Samaha, R. R. and Noller, H. F. (1997) Mutations at nucleotides G2251 and U2585 of 23 S rRNA perturb the peptidyl transferase center of the ribosome 1 1 Edited by P. E. Wright. Journal of Molecular Biology, 266, 40-50.
19. d'Aquino, A. E., Kim, D. S. and Jewett, M. C. (2018) Engineered Ribosomes for Basic Science and Synthetic Biology. Annual Review of Chemical and Biomolecular Engineering, 9, 311-340.
20. Orelle, C., Carlson, E. D., Szal, T., Florin, T., Jewett, M. C. and Mankin, A. S. (2015) Protein synthesis by ribosomes with tethered subunits. Nature, 524, 119-124.
21. Liu, Y., Kim, D. S. and Jewett, M. C. (2017) Repurposing ribosomes for synthetic biology. Current Opinion in Chemical Biology, 40, 87-94.
22. Carlson, E. D., Gan, R., Hodgman, C. E. and Jewett, M. C. (2012) Cell-free protein synthesis: Applications come of age. Biotechnology Advances, 30, 1185-1194.
23. Martin, R. W., Des Soye, B. J., Kwon, Y. C., Kay, J., Davis, R. G., Thomas, P. M., Majewska, N. I., Chen, C. X., Marcum, R. D., Weiss, M. G. et al. (2018) Cell-free protein synthesis from genomically recoded bacteria enables multisite incorporation of noncanonical amino acids. Nat Commun, 9, 1203.
24. Huang, A., Nguyen, P. Q., Stark, J. C., Takahashi, M. K., Donghia, N., Ferrante, T., Dy, A. J., Hsu, K. J., Dubner, R. S., Pardee, K. et al. (2018) BioBits™ Explorer: A modular synthetic biology education kit. Science Advances, 4, eaat5105.
25. Stark, J. C., Huang, A., Nguyen, P. Q., Dubner, R. S., Hsu, K. J., Ferrante, T. C., Anderson, M., Kanapskyte, A., Mucha, Q., Packett, J. S. et al. (2018) BioBits™ Bright: A fluorescent synthetic biology education kit. Science Advances, 4, eaat5107.
26. Kightlinger, W., Lin, L., Rosztoczy, M., Li, W., DeLisa, M. P., Mrksich, M. and Jewett, M. C. (2018) Design of glycosylation sites by rapid synthesis and analysis of glycosyltransferases. Nat Chem Biol, 14, 627-635.
27. Jaroentomeechai, T., Stark, J. C., Natarajan, A., Glasscock, C. J., Yates, L. E., Hsu, K. J., Mrksich, M., Jewett, M. C. and DeLisa, M. P. (2018) Single-pot glycoprotein biosynthesis using a cell-free transcription-translation system enriched with glycosylation machinery. Nat Commun, 9, 2686.
28. Polacek, N. (2011) The ribosome meets synthetic biology. Chembiochem, 12, 2122-2124.
29. Clementi, N., Chirkova, A., Puffer, B., Micura, R. and Polacek, N. (2010) Atomic mutagenesis reveals A2660 of 23S ribosomal RNA as key to EF-G GTPase activation. Nat Chem Biol, 6, 344-351.
30. Erlacher, M. D., Chirkova, A., Voegele, P. and Polacek, N. (2011) Generation of chemically engineered ribosomes for atomic mutagenesis studies on protein biosynthesis. Nat. Protocols, 6, 580-592.
31. Willi, J., Kupfer, P., Evequoz, D., Fernandez, G., Katz, A., Leumann, C. and Polacek, N. (2018) Oxidative stress damages rRNA inside the ribosome and differentially affects the catalytic center. Nucleic Acids Res, 46, 1945-1957.
32. Fritz, B. R., Jamil, O. K. and Jewett, M. C. (2015) Implications of macromolecular crowding and reducing conditions for in vitro ribosome construction. Nucleic Acids Res.
33. Fritz, B. R. and Jewett, M. C. (2014) The impact of transcriptional tuning on in vitro integrated rRNA transcription and ribosome construction. Nucleic Acids Res, 42, 6774-6785.
34. Jewett, M. C., Fritz, B. R., Timmerman, L. E. and Church, G. M. (2013) In vitro integration of ribosomal RNA synthesis, ribosome assembly, and translation. Mol Syst Biol, 9, 678.
35. Liu, Y., Fritz, B. R., Anderson, M. J., Schoborg, J. A. and Jewett, M. C. (2014) Characterizing and Alleviating Substrate Limitations for Improved in vitro Ribosome Construction. ACS Synth Biol.
36. Nierhaus, K. H. and Dohme, F. (1974) Total Reconstitution of Functionally Active 50S Ribosomal Subunits from *Escherichia coli*. Proceedings of the National Academy of Sciences of the United States of America, 71, 4713-4717.
37. Semrad, K. and Green, R. (2002) Osmolytes stimulate the reconstitution of functional 50S ribosomes from in vitro transcripts of *Escherichia coli* 23S rRNA. Rna, 8, 401-411.
38. Maki, J. A. and Culver, G. M. (2005) Recent developments in factor-facilitated ribosome assembly. Methods, 36, 313-320.
39. Green, R. and Noller, H. F. (1999) Reconstitution of Functional 50S Ribosomes from in vitro Transcripts of *Bacillus stearothermophilus* 23S rRNA. Biochemistry, 38, 1772-1779.
40. O'Connor, M., Thomas, C. L., Zimmermann, R. A. and Dahlberg, A. E. (1997) Decoding fidelity at the ribosomal A and P sites: influence of mutations in three different regions of the decoding domain in 16S rRNA. Nucleic Acids Research, 25, 1185-1193.

41. Moine, H. and Dahlberg, A. E. (1994) Mutations in helix 34 of *Escherichia coli* 16 S ribosomal RNA have multiple effects on ribosome function and synthesis. J Mol Biol, 243, 402-412.
42. O'Connor, M. and Dahlberg, A. E. (1993) Mutations at U2555, a tRNA-protected base in 23 S rRNA, affect translational fidelity. Proceedings of the National Academy of Sciences, 90, 9214-9218.
43. Yarza, P., Ludwig, W., Euzéby, J., Amann, R., Schleifer, K.-H., Glöckner, F. O. and Rosselló-Móra, R. (2010) Update of the All-Species Living Tree Project based on 16S and 23S rRNA sequence analyses. Systematic and Applied Microbiology, 33, 291-299.
44. Nierhaus, K. H. (1990) In Spedding, G. (ed.), Ribosomes and Protein Synthesis: A Practical Approach. IRL Press, Oxford, pp. 161-189.
45. Swartz, J. R., Jewett, M. C. and Woodrow, K. A. (2004) Cell-free protein synthesis with prokaryotic combined transcription-translation. Methods Mol Biol, 267, 169-182.
46. Polikanov, Y. S., Steitz, T. A. and Innis, C. A. (2014) A proton wire to couple aminoacyl-tRNA accommodation and peptide-bond formation on the ribosome. Nature structural & molecular biology, 21, 787-793.
47. Polacek, N., Gaynor, M., Yassin, A. and Mankin, A. S. (2001) Ribosomal peptidyl transferase can withstand mutations at the putative catalytic nucleotide. Nature, 411, 498-501.
48. Gregory, S. T., Lieberman, K. R. and Dahlberg, A. E. (1994) Mutations in the peptidyl transferase region of *E. coli* 23S rRNA affecting translational accuracy. Nucleic Acids Research, 22, 279-284.
49. O'Connor, M., Lee, W.-C. M., Mankad, A., Squires, C. L. and Dahlberg, A. E. (2001) Mutagenesis of the peptidyltransferase center of 23S rRNA: the invariant U2449 is dispensable. Nucleic Acids Research, 29, 710-715.
50. O'Connor, M., Willis, N. M., Bossi, L., Gesteland, R. F. and Atkins, J. F. (1993) Functional tRNAs with altered 3' ends. Embo j, 12, 2559-2566.
51. Hesslein, A. E., Katunin, V. I., Beringer, M., Kosek, A. B., Rodnina, M. V. and Strobel, S. A. (2004) Exploration of the conserved A+C wobble pair within the ribosomal peptidyl transferase center using affinity purified mutant ribosomes. Nucleic Acids Research, 32, 3760-3770.
52. Pape, T., Wintermeyer, W. and Rodnina, M. V. (1998) Complete kinetic mechanism of elongation factor Tu-dependent binding of aminoacyl-tRNA to the A site of the <em>E. coli</em> ribosome. The EMBO Journal, 17, 7490-7497.
53. Porse, B. T., Thi-Ngoc, H. P. and Garrett, R. A. (1996) The Donor Substrate Site within the Peptidyl Transferase Loop of 23 S rRNA and its Putative Interactions with the CCA-end of N-blocked Aminoacyl-tRNAPhe. Journal of Molecular Biology, 264, 472-483.
54. Bocchetta, M., Xiong, L. and Mankin, A. S. (1998) 23S rRNA positions essential for tRNA binding in ribosomal functional sites. Proceedings of the National Academy of Sciences, 95, 3525.
55. Dedkova, L. M., Fahmi, N. E., Paul, R., del Rosario, M., Zhang, L., Chen, S., Feder, G. and Hecht, S. M. (2012) beta-Puromycin selection of modified ribosomes for in vitro incorporation of beta-amino acids. Biochemistry, 51, 401-415.
56. Maini, R., Chowdhury, S. R., Dedkova, L. M., Roy, B., Daskalova, S. M., Paul, R., Chen, S. and Hecht, S. M. (2015) Protein Synthesis with Ribosomes Selected for the Incorporation of β-Amino Acids. Biochemistry.
57. Maini, R., Nguyen, D. T., Chen, S., Dedkova, L. M., Chowdhury, S. R., Alcala-Torano, R. and Hecht, S. M. (2013) Incorporation of beta-amino acids into dihydrofolate reductase by ribosomes having modifications in the peptidyltransferase center. Bioorg Med Chem, 21, 1088-1096.
58. Melo Czekster, C., Robertson, W. E., Walker, A. S., Söll, D. and Schepartz, A. (2016) In Vivo Biosynthesis of a β-Amino Acid-Containing Protein. Journal of the American Chemical Society, 138, 5194-5197.
59. Aleksashin, N. A., Leppik, M., Hockenberry, A. J., Klepacki, D., Vazquez-Laslop, N., Jewett, M. C., Remme, J. and Mankin, A. S. (2019) Assembly and functionality of the ribosome with tethered subunits. Nat Commun, 10, 930.
60. Fried, S. D., Schmied, W. H., Uttamapinant, C. and Chin, J. W. (2015) Ribosome Subunit Stapling for Orthogonal Translation in *E. coli*. Angewandte Chemie (International Ed. In English), 54, 12791-12794.
61. Schmied, W. H., Tnimov, Z., Uttamapinant, C., Rae, C. D., Fried, S. D. and Chin, J. W. (2018) Controlling orthogonal ribosome subunit interactions enables evolution of new function. Nature, 564, 444-448.
62. Dedkova, L. M. and Hecht, S. M. (2019) Expanding the Scope of Protein Synthesis Using Modified Ribosomes. Journal of the American Chemical Society, 141, 6430-6447.
63. Liu, C. C., Jewett, M. C., Chin, J. W. and Voigt, C. A. (2018) Toward an orthogonal central dogma. Nature Chemical Biology, 14, 103.
64. Noeske, J., Wasserman, M. R., Terry, D. S., Altman, R. B., Blanchard, S. C. and Cate, J. H. (2015) High-resolution structure of the *Escherichia coli* ribosome. Nat Struct Mol Biol, 22, 336-341.
65. Osterman, I. A., Khabibullina, N. F., Komarova, E. S., Kasatsky, P., Kartsev, V. G., Bogdanov, A. A., Dontsova, O. A., Konevega, A. L., Sergiev, P. V. and Polikanov, Y. S. (2017) Madumycin II inhibits peptide bond formation by forcing the peptidyl transferase center into an inactive state. Nucleic Acids Res.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An engineered *Escherichia coli* ribosome comprising one or more engineered mutations in ribosomal RNA of the ribosome, wherein at least one of the one or more engineered mutations is selected from the group consisting of A2448C, A2448U, A2448G, A2453U, A2453C, C2456U, C2456G, C2456A, C2496U, C2496G, C2496A, A2497U, A2497C, C2498U, C2499G, U2500A, U2500G, A2567C, G2588U, G2588C, C2606U, C2606A, C2606G, G2607U, and G2607A, wherein the positions are defined relative to a wild-type *Escherichia coli* 23 S rRNA encoded by SEQ ID NO: 1.

2. The engineered ribosome of claim 1, further comprising one or more additional engineered mutations in the peptidyl transferase center (PTC) of 23S rRNA.

3. The engineered ribosome of claim 1, further comprising one or more additional engineered mutations in the central PTC-ring of 23S rRNA, defined as G2057-C2063, G2447-C2456, C2496-C2507, G2582-G2588, A2602, and C2606-C2611.

4. The engineered ribosome of claim 1, further comprising one or more additional engineered mutations in the A-loop of the PTC, defined as U2548-A2560.

5. The engineered ribosome of claim 1, further comprising one or more additional engineered mutations in the P-loop of the PTC, defined as G2250-C2254.

6. A method of synthesizing a sequence-defined polymer encoded by a messenger RNA (mRNA), the method comprising translating the mRNA using the engineered ribosome of claim 1.

7. The method of claim 6, wherein the method is performed in vitro in a cell-free system.

8. The method of claim 6, wherein the method is performed in vivo in a cell.

* * * * *

```
                         SEQUENCE LISTING

<160> NUMBER OF SEQ ID NOS: 1

<210> SEQ ID NO 1
<211> LENGTH: 2904
<212> TYPE: DNA
<213> ORGANISM: Escherichia coli

<400> SEQUENCE: 1
ggttaagcga ctaagcgtac acggtggatg ccctggcagt cagaggcgat gaaggacgtg      60
ctaatctgcg ataagcgtcg gtaaggtgat atgaaccgtt ataaccggcg atttccgaat     120
ggggaaaccc agtgtgtttc gacacactat cattaactga atccataggt taatgaggcg     180
aaccggggga actgaaacat ctaagtaccc cgaggaaaag aaatcaaccg agattccccc     240
agtagcggcg agcgaacggg gagcagccca gagcctgaat cagtgtgtgt gttagtggaa     300
gcgtctggaa aggcgcgcga tacagggtga cagccccgta cacaaaaatg cacatgctgt     360
gagctcgatg agtaggcgg gacacgtggt atcctgtctg aatatggggg gaccatcctc     420
caaggctaaa tactcctgac tgaccgatag tgaaccagta ccgtgaggga aaggcgaaaa     480
gaaccccggc gaggggagtg aaaaagaacc tgaaaccgtg tacgtacaag cagtgggagc     540
acgcttaggc gtgtgactgc gtaccttttg tataatgggt cagcgactta tattctgtag     600
caaggttaac cgaataggggg agccgaaggg aaaccgagtc ttaactgggc gttaagttgc     660
agggtataga cccgaaaccc ggtgatctag ccatgggcag gttgaaggtt gggtaacact     720
aactggagga ccgaaccgac taatgttgaa aaattagcgg atgacttgtg gctggggggtg     780 aaaggccaat caaaccggga gatagctggt tctccccgaa agctatttag gtagcgcctc     840
gtgaattcat ctccggggt agagcactgt ttcggcaagg gggtcatccc gacttaccaa     900
cccgatgcaa actgcgaata ccggagaatg ttatcacggg agacacacgg cgggtgctaa     960
cgtccgtcgt gaagagggaa acaacccaga ccgccagcta aggtcccaaa gtcatggtta    1020
agtgggaaac gatgtgggaa ggcccagaca gccaggatgt tggcttagaa gcagccatca    1080
tttaaagaaa gcgtaatagc tcactggtcg agtcggcctg cgcggaagat gtaacggggc    1140
taaaccatgc accgaagctg cggcagcgac gcttatgcgt tgttgggtag gggagcgttc    1200
tgtaagcctg cgaaggtgtg ctgtgaggca tgctggaggt atcagaagtg cgaatgctga    1260
cataagtaac gataaagcgg gtgaaaagcc cgctcgccgg aagaccaagg gttcctgtcc    1320
aacgttaatc ggggcagggt gagtcgaccc ctaaggcgag gccgaaaggc gtagtcgatg    1380
ggaaacaggt taatattcct gtacttggtg ttactgcgaa gggggggacgg agaaggctat    1440 gttggccggg cgacggttgt cccggtttaa gcgtgtaggc tggttttcca ggcaaatccg    1500
gaaaatcaag gctgaggcgt gatgacgagg cactacggtc ctgaagcaac aaatgccctg    1560
cttccaggaa aagcctctaa gcatcaggta acatcaaatc gtaccccaaa ccgacacagg    1620
tggtcaggta gagaatacca aggcgcttga gagaactcgg gtgaaggaac taggcaaaat    1680
ggtgccgtaa cttcgggaga aggcacgctg atatgtaggt gaggtccctc gcggatggag    1740
ctgaaatcag tcgaagatac cagctggctg caactgttta ttaaaaacac agcactgtgc    1800
aaacacgaaa gtggacgtat acggtgtgac gcctgcccgg tgccggaagg ttaattgatg    1860
```

```
gggttagcgc aagcgaagct cttgatcgaa gccccggtaa acggcggccg taactataac    1920
ggtcctaagg tagcgaaatt ccttgtcggg taagttccga cctgcacgaa tggcgtaatg    1980
atggccaggc tgtctccacc cgagactcag tgaaattgaa ctcgctgtga agatgcagtg    2040
tacccgcggc aagacggaaa gaccccgtga acctttacta tagcttgaca ctgaacattg    2100
agccttgatg tgtaggatag gtgggaggct ttgaagtgtg gacgccagtc tgcatggagc    2160
cgaccttgaa ataccaccct ttaatgtttg atgttctaac gttgacccgt aatccgggtt    2220
gcggacagtg tctggtgggt agtttgactg gggcggtctc ctcctaaaga gtaacggagg    2280
agcacgaagg ttggctaatc ctggtcggac atcaggaggt tagtgcaatg gcataagcca    2340
gcttgactgc gagcgtgacg gcgcgagcag gtgcgaaagc aggtcatagt gatccggtgg    2400
ttctgaatgg aagggccatc gctcaacgga taaaaggtac tccggggata acaggctgat    2460
accgcccaag agttcatatc gacggcggtg tttggcacct cgatgtcggc tcatcacatc    2520 ctgggctga agtaggtccc aagggtatgg ctgttcgcca tttaaagtgg tacgcgagct    2580
gggtttagaa cgtcgtgaga cagttcggtc cctatctgcc gtgggcgctg gagaactgag    2640
gggggctgct cctagtacga gaggaccgga gtggacgcat cactggtgtt cgggttgtca    2700
tgccaatggc actgcccggt agctaaatgc ggaagagata agtgctgaaa gcatctaagc    2760
acgaaacttg ccccgagatg agttctccct gaccctttaa gggtcctgaa ggaacgttga    2820
agacgacgac gttgataggc cgggtgtgta agcgcagcga tgcgttgagc taaccggtac    2880
taatgaaccg tgaggcttaa cctt                                           2904
```